(12) United States Patent
Heo et al.

(10) Patent No.: US 11,653,564 B2
(45) Date of Patent: May 16, 2023

(54) COMPOUND AND ORGANIC LIGHT-EMITTING DEVICE COMPRISING SAME

(71) Applicant: LG CHEM, LTD., Seoul (KR)

(72) Inventors: Dong Uk Heo, Daejeon (KR); Dong Hoon Lee, Daejeon (KR); Jungoh Huh, Daejeon (KR); Boonjae Jang, Daejeon (KR); Minyoung Kang, Daejeon (KR); Miyeon Han, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 480 days.

(21) Appl. No.: 16/322,065

(22) PCT Filed: Aug. 9, 2017

(86) PCT No.: PCT/KR2017/008621
§ 371 (c)(1),
(2) Date: Jan. 30, 2019

(87) PCT Pub. No.: WO2018/030786
PCT Pub. Date: Feb. 15, 2018

(65) Prior Publication Data
US 2019/0189929 A1    Jun. 20, 2019

(30) Foreign Application Priority Data

Aug. 9, 2016 (KR) .................. 10-2016-0101362

(51) Int. Cl.
*C07D 405/14* (2006.01)
*C07D 405/10* (2006.01)
(Continued)

(52) U.S. Cl.
CPC ......... *H10K 85/654* (2023.02); *C07D 311/80* (2013.01); *C07D 405/10* (2013.01);
(Continued)

(58) Field of Classification Search
CPC ..... H01L 51/0067; H01L 51/50; H01L 51/00; H01L 51/0072; H01L 51/0073;
(Continued)

(56) References Cited

U.S. PATENT DOCUMENTS

2011/0227054 A1    10/2011   Pampuch et al.
2011/0240983 A1*   10/2011   Sekiguchi ........... H01L 51/0067
                                                    257/40
(Continued)

FOREIGN PATENT DOCUMENTS

CN   106478610 A    3/2017
CN   106478611      3/2017
(Continued)

OTHER PUBLICATIONS

'Reactions of 9-Phenylxanthylium Salts with Organometallic Reagents. I', Chemical and Pharmaceutical Bulletin, 1973, vol. 21, No. 6, p. 1318-1326.
(Continued)

*Primary Examiner* — Michael Y Sun
(74) *Attorney, Agent, or Firm* — Dentons US LLP

(57) ABSTRACT

The present specification provides a compound of Chemical Formula 1 and an organic light emitting device including the same. The compound of Chemical Formula 1 used in an organic material layer of the organic light emitting device provides improved driving voltage and light efficiency, and increased service lifetime.

7 Claims, 4 Drawing Sheets

(51) Int. Cl.
  *C07D 311/80* (2006.01)
  *C07D 471/04* (2006.01)
(52) U.S. Cl.
  CPC ......... *C07D 405/14* (2013.01); *C07D 471/04* (2013.01); *H10K 50/00* (2023.02); *H10K 85/6572* (2023.02); *H10K 85/6574* (2023.02); *H10K 99/00* (2023.02); *H10K 50/16* (2023.02); *H10K 50/171* (2023.02)
(58) Field of Classification Search
  CPC ............ H01L 51/5072; H01L 51/5092; C07D 311/80; C07D 471/04; C07D 405/14; C07D 405/10
  See application file for complete search history.

(56) References Cited

U.S. PATENT DOCUMENTS

| | | |
|---|---|---|
| 2012/0228554 A1 | 9/2012 | Franz et al. |
| 2015/0115241 A1 | 4/2015 | Zoellner et al. |
| 2015/0295181 A1 | 10/2015 | Mujica-Fernaud et al. |
| 2015/0333277 A1 | 11/2015 | Kim et al. |
| 2016/0096809 A1* | 4/2016 | Franz ................... C07D 409/14 252/500 |
| 2016/0118599 A1 | 4/2016 | Jeong et al. |
| 2017/0217992 A1 | 8/2017 | Jun et al. |

FOREIGN PATENT DOCUMENTS

| | | |
|---|---|---|
| CN | 107056763 A | 8/2017 |
| JP | 2013510889 A | 3/2013 |
| KR | 20110102371 A | 9/2011 |
| KR | 20140108778 A | 9/2014 |
| KR | 20140135117 A | 11/2014 |
| KR | 20150002740 A | 1/2015 |
| KR | 20150077263 A | 7/2015 |
| KR | 20150083917 A | 7/2015 |
| KR | 20160018406 A | 2/2016 |
| KR | 20160047670 A | 5/2016 |
| WO | 2016096851 A1 | 6/2016 |

OTHER PUBLICATIONS

Supplementary Search Report of European Patent Office in Appl'n No. EP17839804, dated May 20, 2019.

* cited by examiner

COMPOUND AND ORGANIC LIGHT-EMITTING DEVICE COMPRISING SAME

CROSS-REFERENCE TO RELATED APPLICATIONS

This application is a National Stage Application of International Application No. PCT/KR2017/008621, filed Aug. 9, 2017, and claims the benefit of Korean Patent Application No. 10-2016-0101362, filed Aug. 9, 2016, the contents of which are incorporated herein by reference in their entirety for all purposes as if fully set forth below.

BACKGROUND ART

An organic light emitting device has a structure in which an organic thin film is disposed between two electrodes. When a voltage is applied to an organic light emitting device having the structure, electrons and holes injected from the two electrodes are bonded to each other in an organic thin film to make a pair, and then emit light while being extinguished. The organic thin film may be composed of a single layer or multi layers, if necessary.

A material for the organic thin film may have a light emitting function, if necessary. For example, as a material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, service life, or efficiency of the organic light emitting device, there is a continuous need for developing a material for an organic thin film.

DETAILED DESCRIPTION OF THE INVENTION

Technical Problem

The present specification provides a compound and an organic light emitting device including the same.

Technical Solution

An exemplary embodiment of the present specification provides a compound represented by the following Chemical Formula 1.

[Chemical Formula 1]

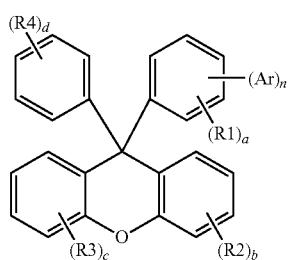

In Chemical Formula 1,

Ar's are the same as or different from each other, and are each independently -L-Ar1, R1 to R4 are the same as or different from each other, and are each independently hydrogen or deuterium, a, b, and c are an integer from 0 to 4, n is an integer from 1 to 4, d is an integer from 0 to 5, n+a is 5 or less, and when n and a to d are 2 or more, substituents in the parenthesis are the same as or different from each other, L is a direct bond; or a substituted or unsubstituted arylene group, Ar1 is selected from the following structural formulae,

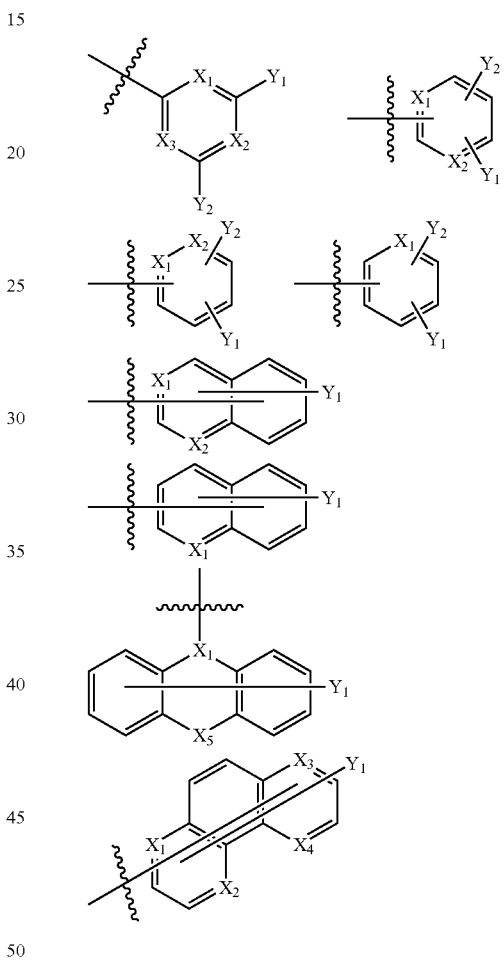

in the structural formulae, $X_1$ to $X_4$ are the same as or different from each other, and are each independently N or CH, and $X_5$ is S or O, and $Y_1$ and $Y_2$ are the same as or different from each other, and are each independently hydrogen; deuterium; a nitrile group; a substituted or unsubstituted alkyl group; a substituted or unsubstituted aryl group; a substituted or unsubstituted heteroaryl group; or a substituted or unsubstituted fused polycyclic group.

Further, the present application provides an organic light emitting device including: a first electrode; a second electrode disposed to face the first electrode; and an organic material layer having one or more layers disposed between the first electrode and the second electrode, in which one or more layers of the organic material layer include the above-described compound.

Advantageous Effects

The compound according to an exemplary embodiment of the present application is used for an organic light emitting device and thus may lower the driving voltage of the organic light emitting device, and improve the light efficiency, and service life characteristics of the device by thermal stability of the compound.

EXPLANATION OF REFERENCE NUMERALS AND SYMBOLS

Figure 1:
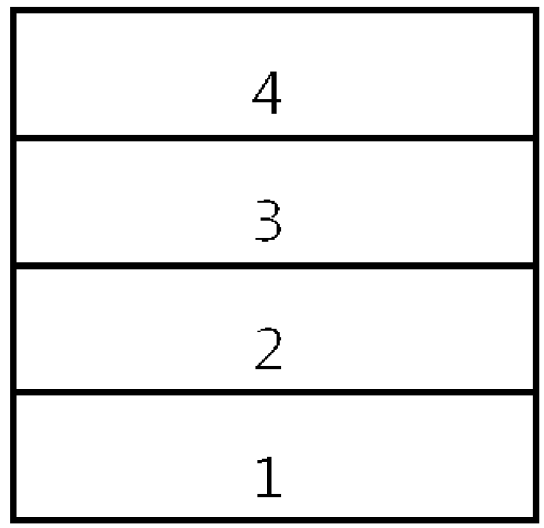
FIG. 1 illustrates an example of an organic light emitting device in which a substrate 1, a positive electrode 2, a light emitting layer 3, and a negative electrode 4 are sequentially stacked.

1: Substrate
2: Positive electrode
3: Light emitting layer
4: Negative electrode
5: Hole injection layer
6: Hole transporting layer
7: Electron transporting layer

BEST MODE

Hereinafter, the present specification will be described in more detail.

The present specification provides the compound represented by Chemical Formula 1.

Examples of the substituents in the present specification will be described below, but are not limited thereto.

In the present specification,

and a dotted line mean a site bonded to another substituent or a binding portion.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group; a hydroxy group; an alkyl group; a cycloalkyl group; an alkenyl group; an alkoxy group; a substituted or unsubstituted phosphine oxide group; an aryl group; and a heteroaryl group, being substituted with a substituent to which two or more substituents among the exemplified substituents are linked, or having no substituent. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, the alkyl group may be straight or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a phosphine oxide group include a diphenylphosphine oxide group, dinaphthylphosphine oxide group, and the like, but are not limited thereto.

In the present specification, when the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the group may be

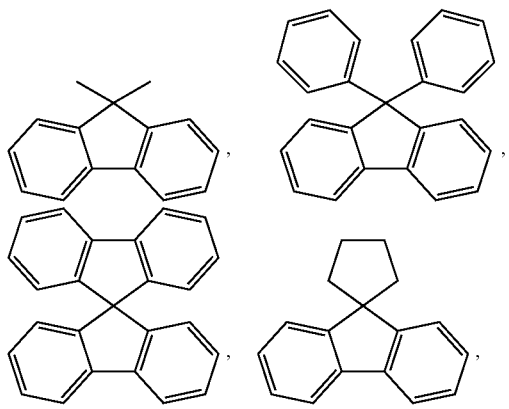

and the like, but is not limited thereto.

In the present specification, a heteroaryl group includes one or more atoms other than carbon, that is, one or more heteroatoms, and specifically, the heteroatom may include one or more atoms selected from the group consisting of O, N, Se, and S, and the like. The number of carbon atoms of the heteroaryl group is not particularly limited, but is preferably 2 to 60 or 2 to 30. Examples of the heteroaryl group include a thiophenyl group, a furanyl group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a hydroacridyl group (for example,

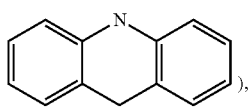 [SMILES: c1ccc2c(c1)Cc1ccccc1N2]), a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzothiazolyl group, a benzocarbazolyl group, a dibenzocarbazolyl group, a benzothiophenyl group, a dibenzothiophenyl group, a benzofuranyl group, a dibenzofuranyl group; a benzosilole group; a dibenzosilole group; a phenanthrolinyl group, a thiazolyl group, an isoxazolyl group, an oxadiazolyl group, a thiadiazolyl group, a benzothiazolyl group, a phenothiazinyl group, a phenoxazinyl group, and fused structures thereof, and the like, but are not limited thereto. In addition, examples of the heterocyclic group include a heterocyclic structure including a sulfonyl group, for example,

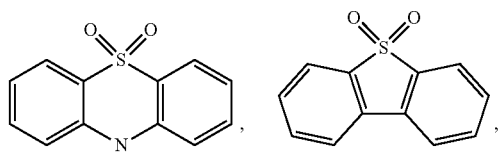

and the like.

In the present specification, a fused heterocyclic group may be a fused ring of an aromatic ring and an aliphatic ring, and may be selected from the examples of the heteroaryl group.

In the present specification, the above-described description on the aryl group may be applied to an arylene except for a divalent arylene group.

In the present specification, the above-described description on the heteroaryl group may be applied to a heteroarylene except for a divalent heteroarylene group. In an exemplary embodiment of the present specification, n is 1.

In an exemplary embodiment of the present specification, Chemical Formula 1 is represented by any one of the following Chemical Formulae 2 to 4.

[Chemical Formula 2]

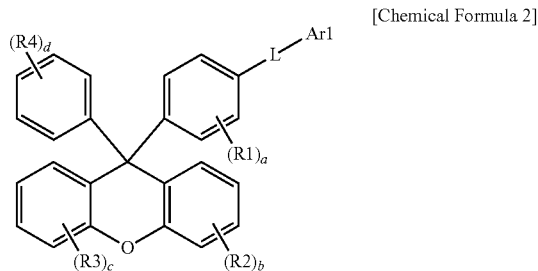

[Chemical Formula 3]

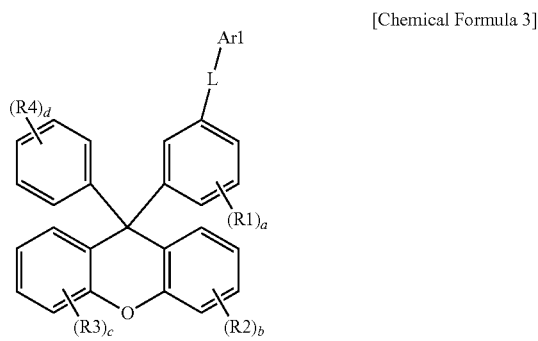

-continued

[Chemical Formula 4]

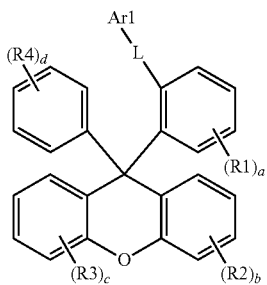

In Chemical Formulae 2 to 4, R1 to R4, a to d, L, and Ar1 are the same as the definitions in Chemical Formula 1.

In an exemplary embodiment of the present specification, L is a direct bond.

In an exemplary embodiment of the present specification, L is an arylene group.

According to an exemplary embodiment of the present specification, L is an arylene group having 6 to 30 carbon atoms.

In an exemplary embodiment of the present specification, L is a monocyclic arylene group.

In an exemplary embodiment of the present specification, L is a direct bond; a phenylene group; a biphenylylene group; or a terphenylylene group.

In an exemplary embodiment of the present specification, L is a direct bond; a phenylene group; or a biphenylylene group.

In an exemplary embodiment of the present specification, L is selected from a direct bond or the following structural formulae.

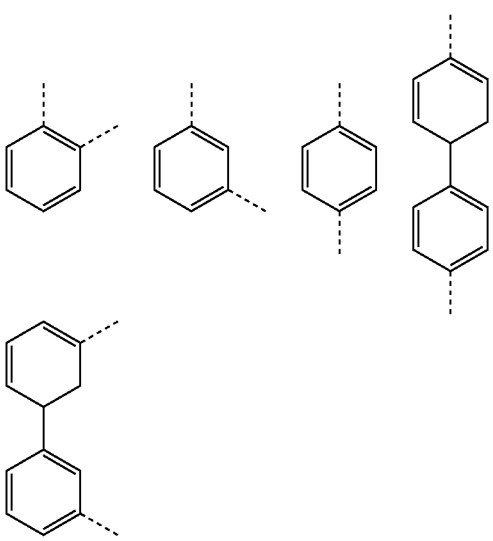

In the structural formulae, a dotted line means a bonding position in which Chemical Formula 1 is bonded to Ar1.

In an exemplary embodiment of the present specification, R1 to R4 are hydrogen.

In an exemplary embodiment of the present specification, Ar1 is selected from the following structural formulae.

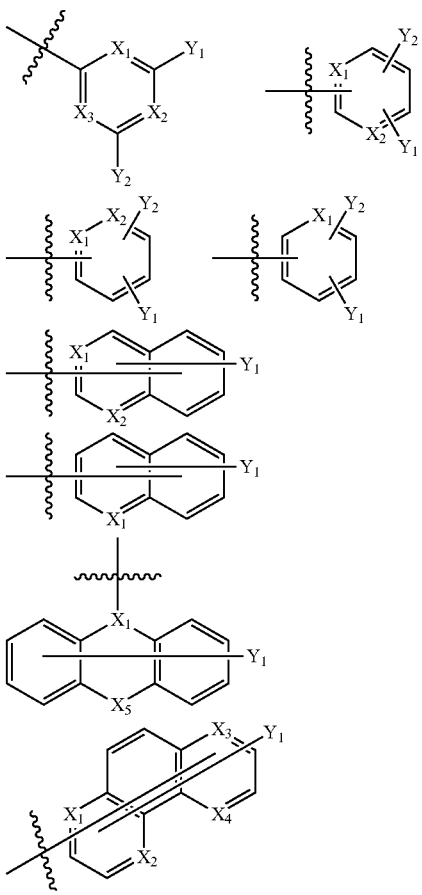

In the structural formulae, $X_1$ to $X_4$ are the same as or different from each other, and are each independently N or CH, and $X_5$ is S or O, and $Y_1$ and $Y_2$ are the same as or different from each other, and are each independently hydrogen; deuterium; a nitrile group; a substituted or unsubstituted alkyl group; a substituted or unsubstituted aryl group; a substituted or unsubstituted heteroaryl group; or a substituted or unsubstituted fused polycyclic group.

In the structural formulae, a wavy line means a position which is bonded to L.

In an exemplary embodiment of the present specification, Ar1 includes at least one N, or has a nitrile group as a substituent.

In an exemplary embodiment of the present specification, at least one of X1 to X4 of Ar1 is N, and when X1 to X4 are all CH, Y1 or Y2 is a nitrile group. When Ar1 is the substituent, there is an excellent effect by forming HOMO and LUMO levels at low levels to smoothly transport electrons and block holes.

In an exemplary embodiment of the present specification, $Y_1$ and $Y_2$ are the same as or different from each other, and are each independently hydrogen; deuterium; a nitrile group; a substituted or unsubstituted aryl group; or a substituted or unsubstituted heteroaryl group.

In an exemplary embodiment of the present specification, $Y_1$ and $Y_2$ are the same as or different from each other, and are each independently hydrogen; deuterium; a nitrile group; a substituted or unsubstituted aryl group having 6 to 30 carbon atoms; or a substituted or unsubstituted heteroaryl group having 2 to 30 carbon atoms.

In an exemplary embodiment of the present specification, $Y_1$ and $Y_2$ are the same as or different from each other, and are each independently hydrogen; deuterium; a nitrile group; a substituted or unsubstituted phenyl group; a substituted or unsubstituted biphenyl group; a substituted or unsubstituted naphthyl group; a substituted or unsubstituted phenanthryl group; a substituted or unsubstituted pyridine group; or a substituted or unsubstituted dibenzofuranyl group.

In an exemplary embodiment of the present specification, $Y_1$ and $Y_2$ are the same as or different from each other, and are each independently hydrogen; deuterium; a nitrile group; a phenyl group; a biphenyl group; a naphthyl group; a phenanthryl group; a pyridine group; or a dibenzofuranyl group.

In an exemplary embodiment of the present specification, Ar1 is selected from the following structural formulae.

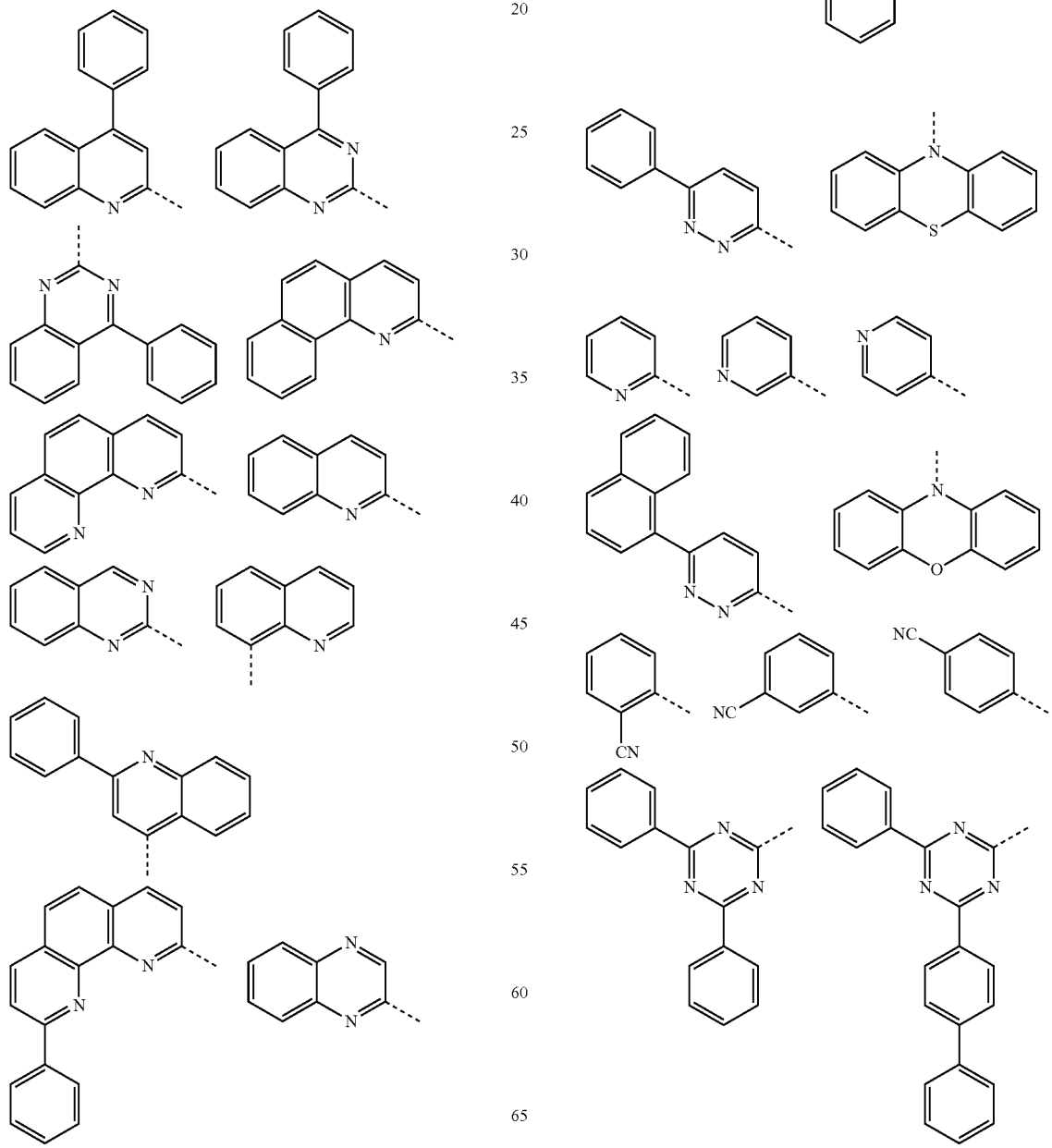

-continued
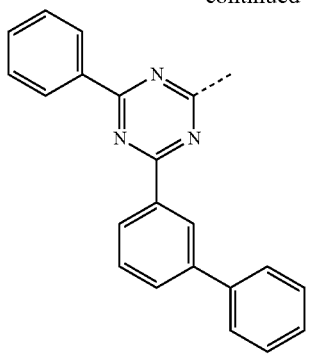
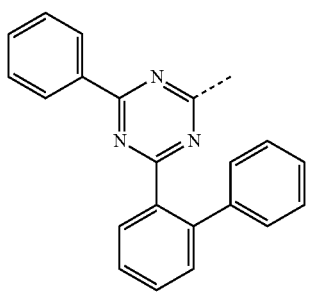
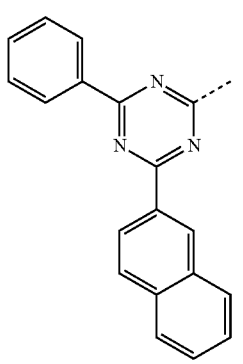
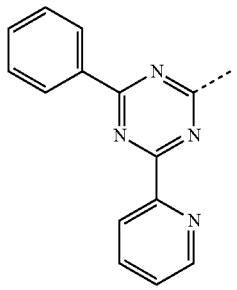
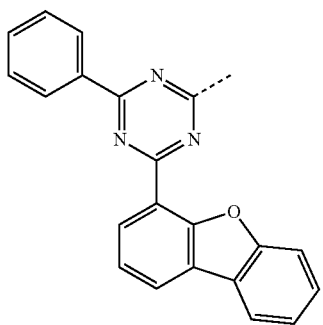
-continued
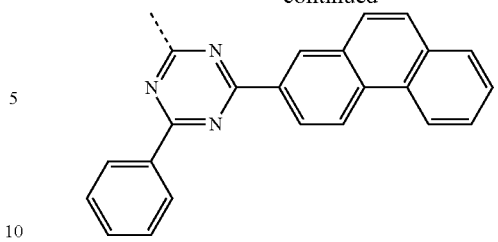
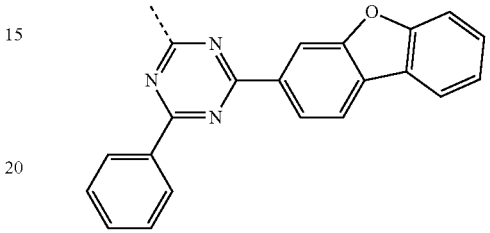
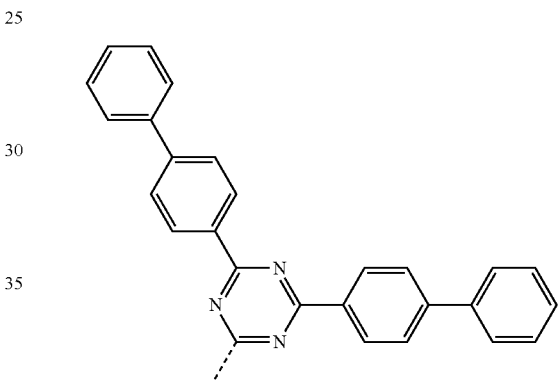
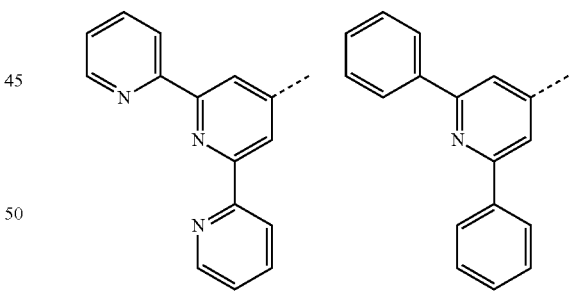

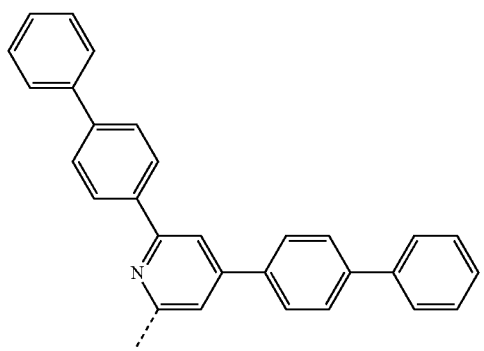
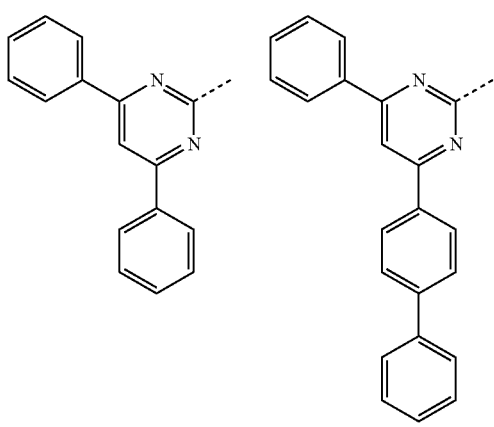
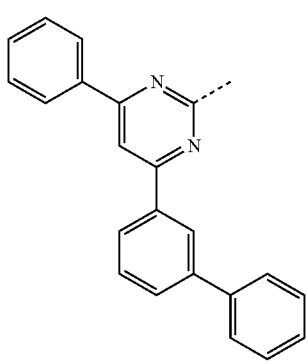
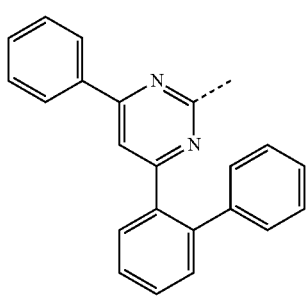
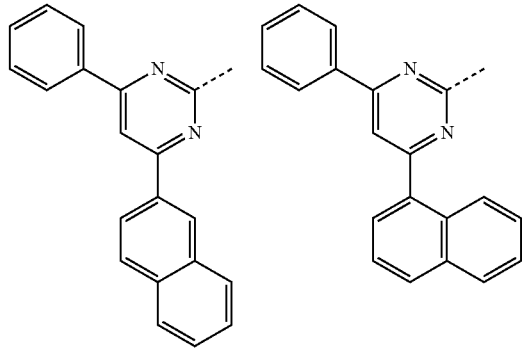
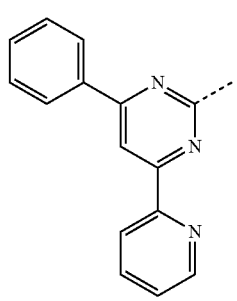
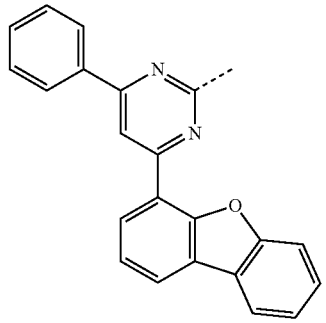
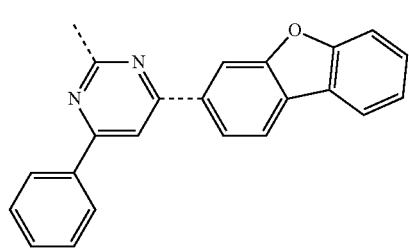

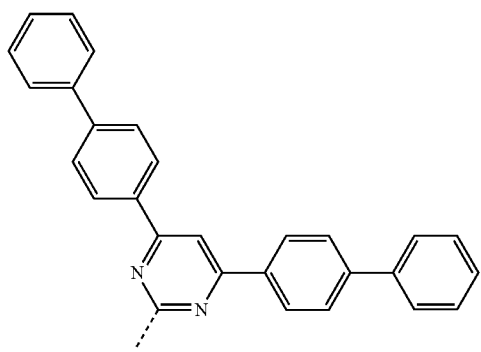
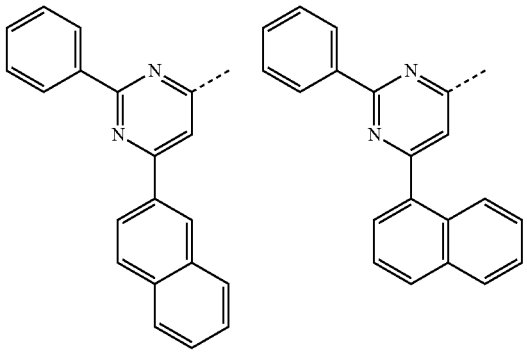
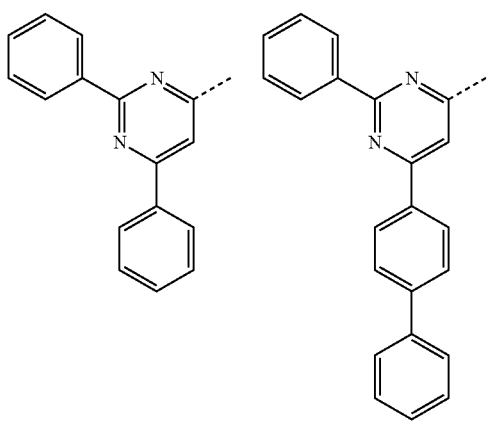
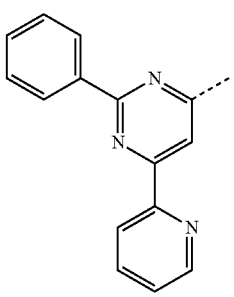
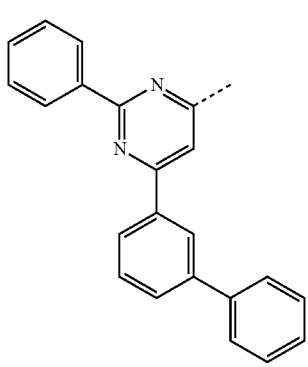
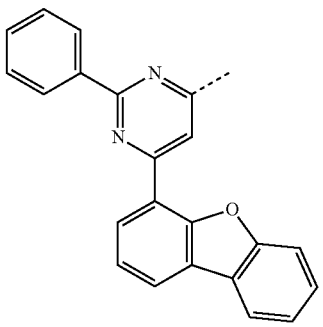
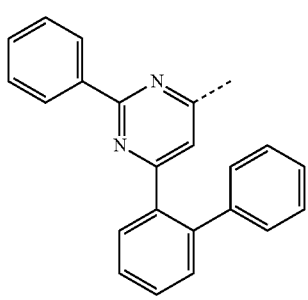
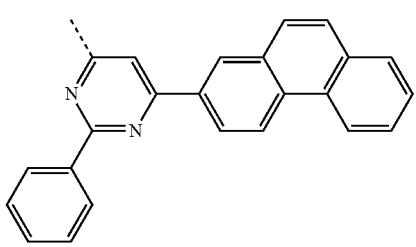
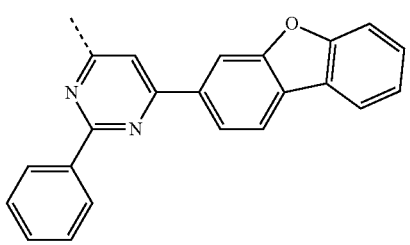

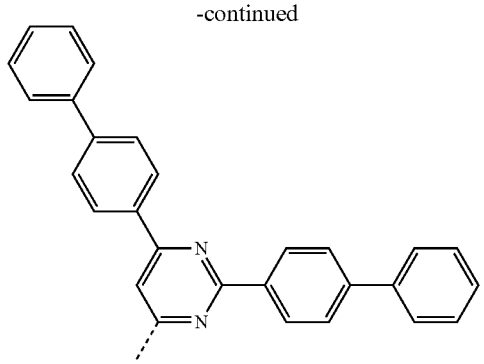
In the structural formulae, a dotted line means a position which is bonded to L.
In an exemplary embodiment of the present specification, the compound represented by Chemical Formula 1 is any one selected from the following structural formulae.
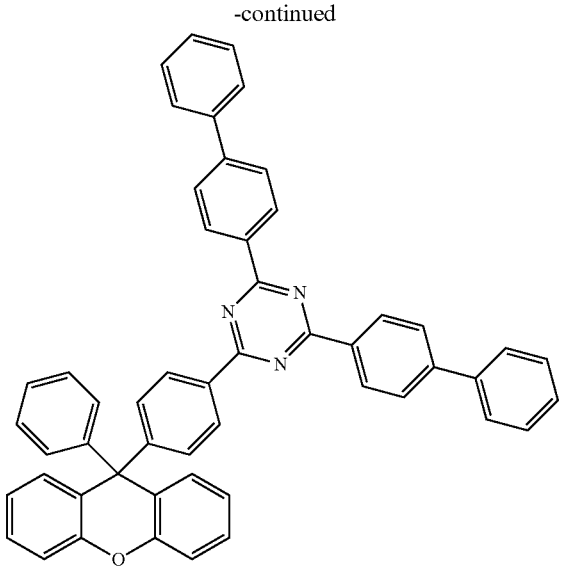
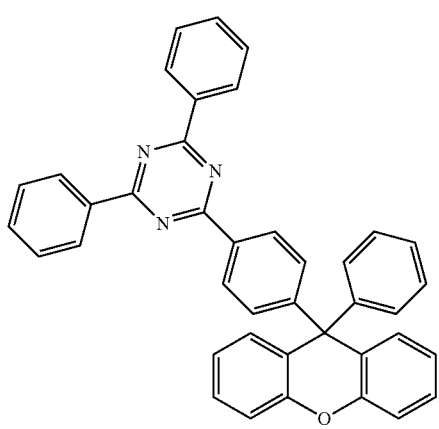
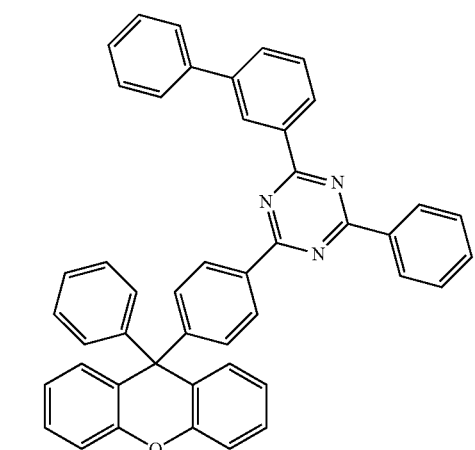
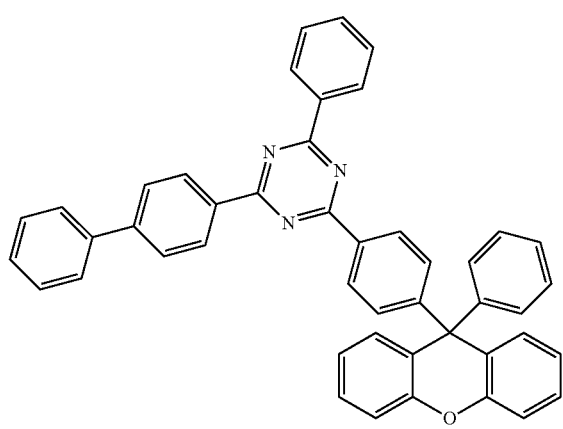
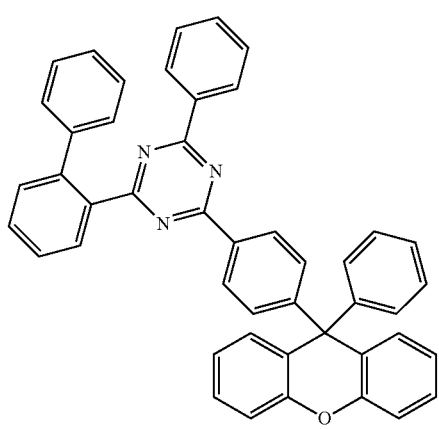

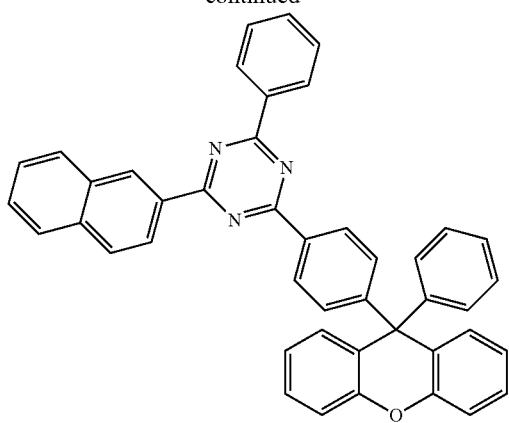
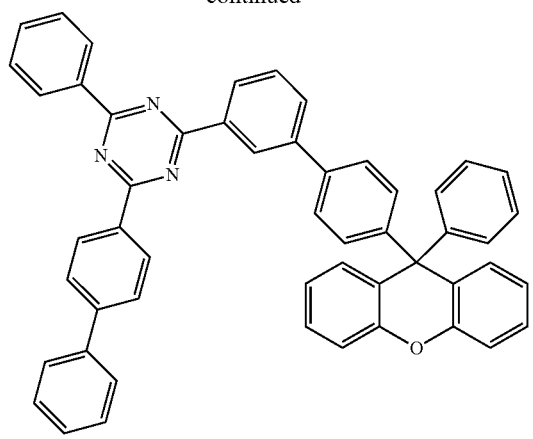
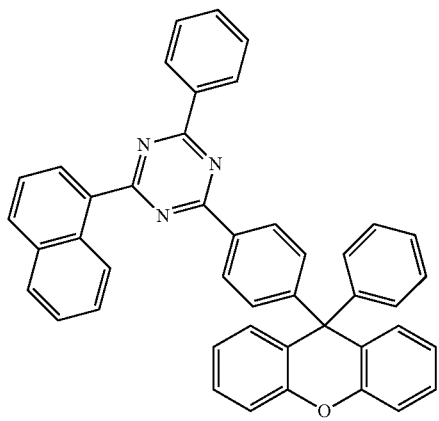
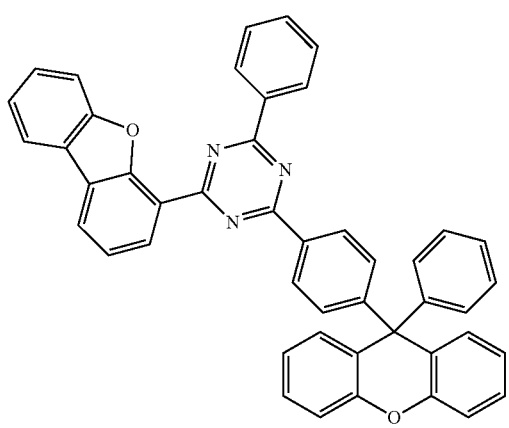
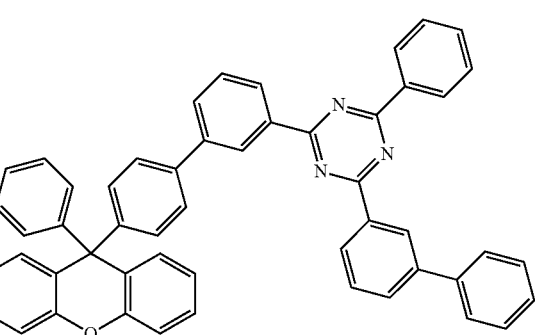
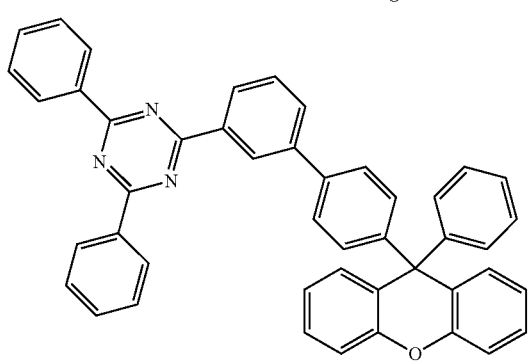

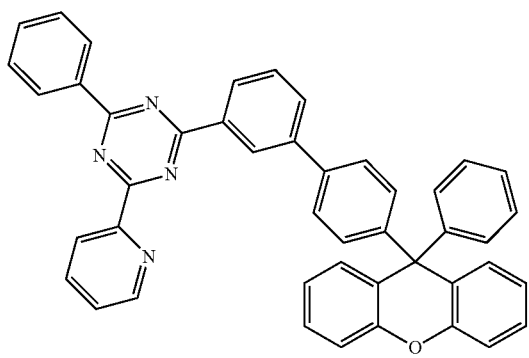
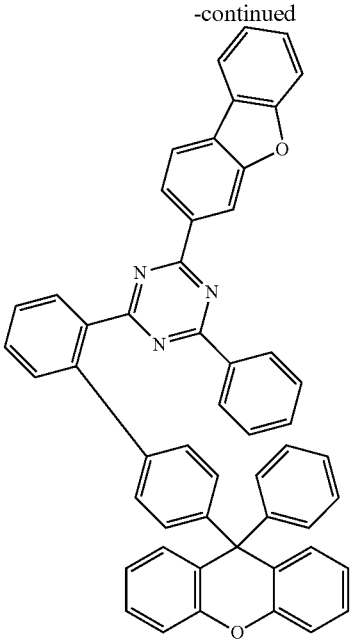
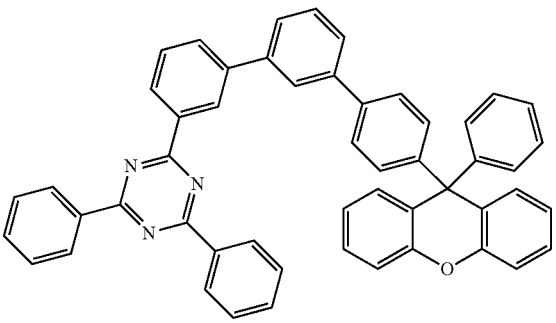

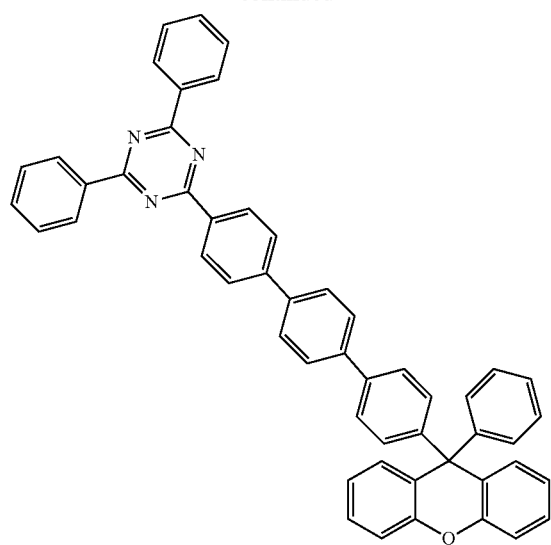 [SMILES: c1ccc(-c2nc(-c3ccccc3)nc(-c3ccc(-c4ccc(-c5ccc(C6(c7ccccc7)c7ccccc7Oc7ccccc76)cc5)cc4)cc3)n2)cc1]
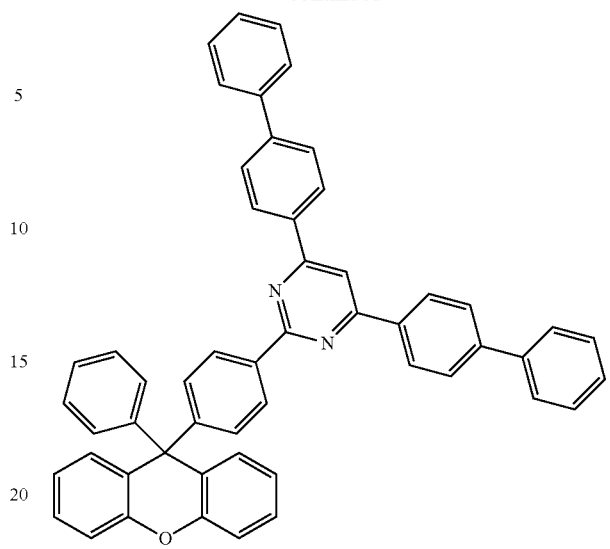
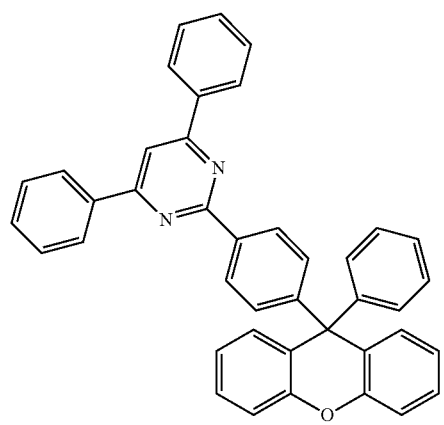
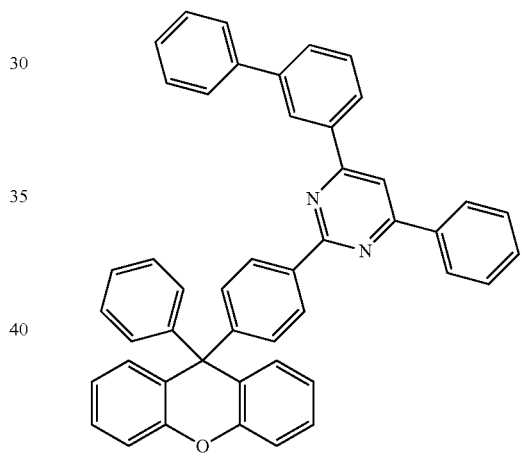
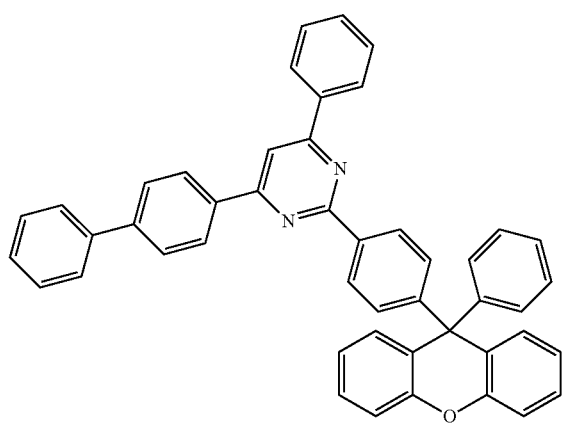
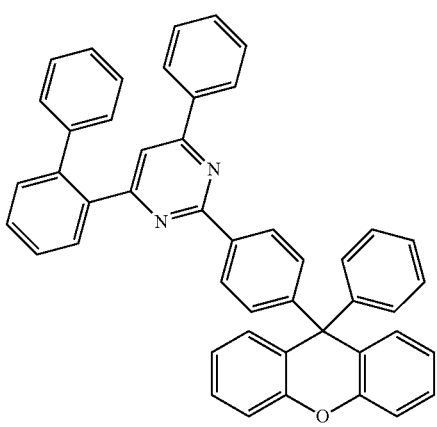

-continued
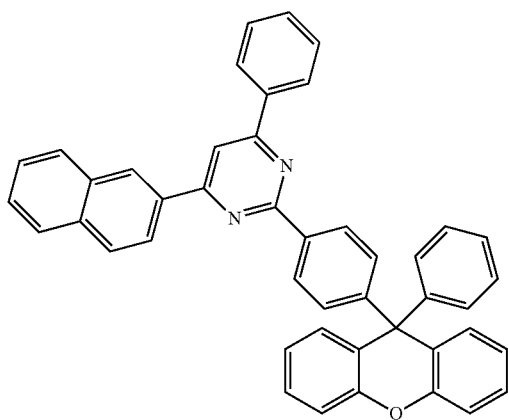
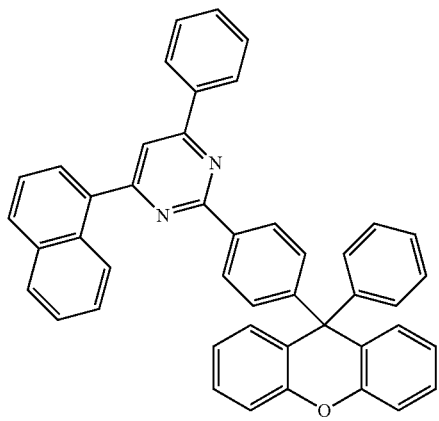
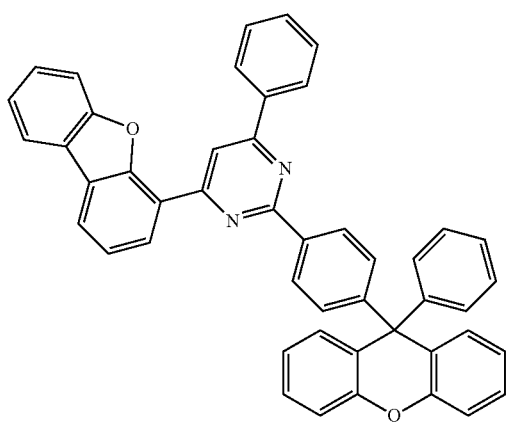
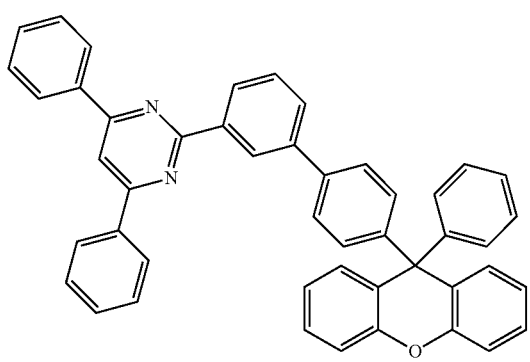
-continued
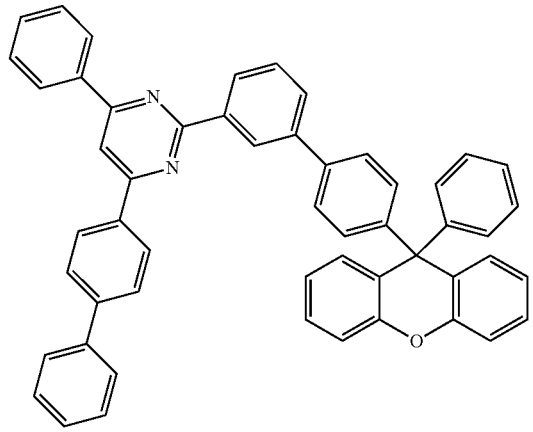
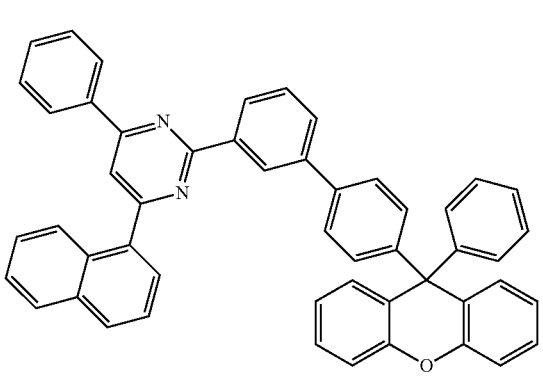
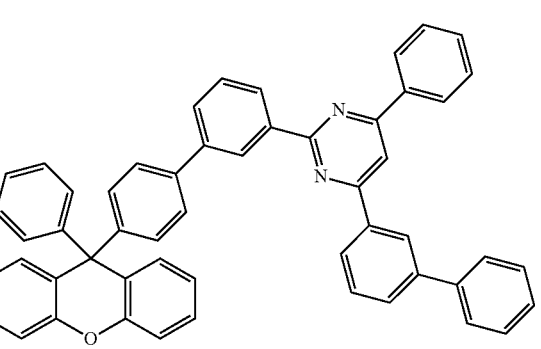
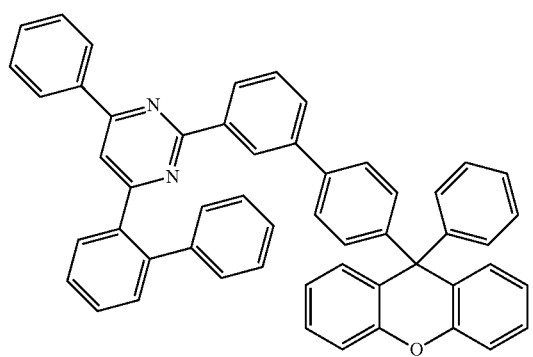

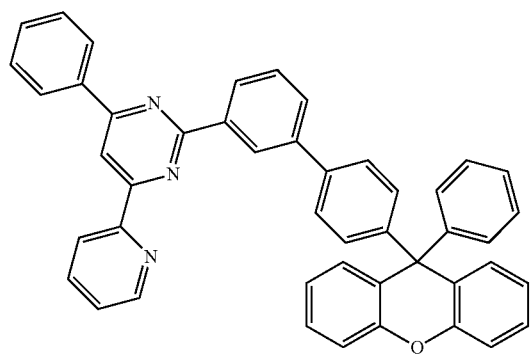
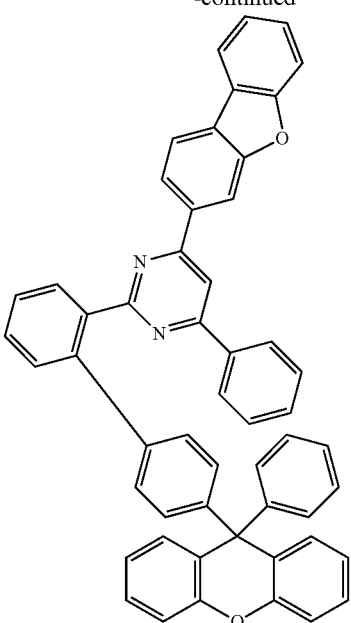
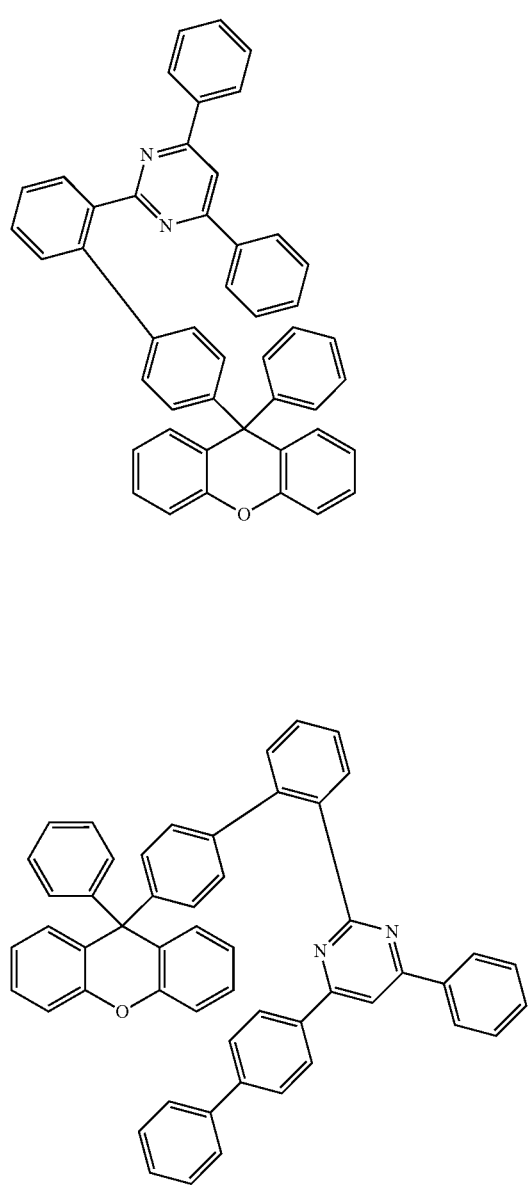
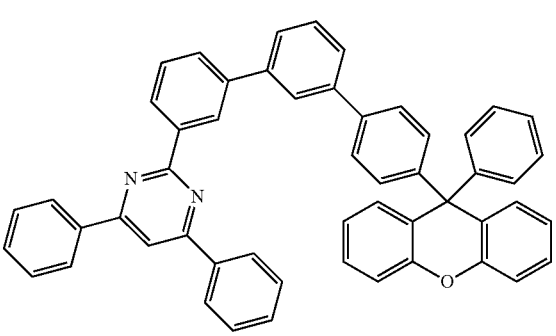

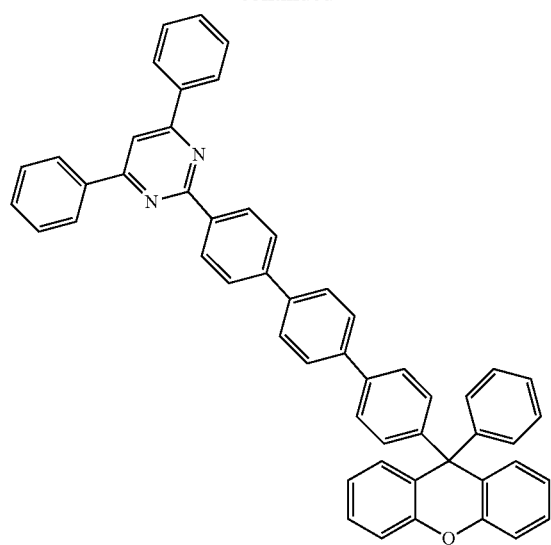 [SMILES: c1ccc(-c2cc(-c3ccccc3)nc(-c3ccc(-c4ccc(-c5ccc(C6(c7ccccc7)c7ccccc7Oc7ccccc76)cc5)cc4)cc3)n2)cc1]
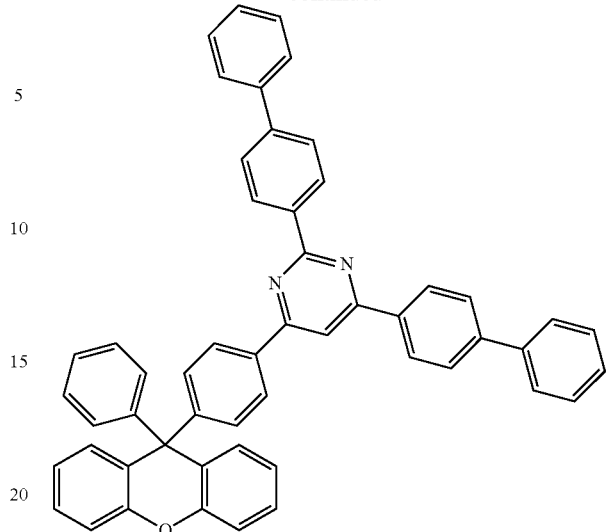
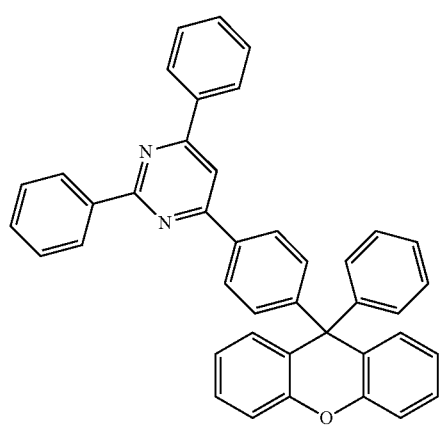
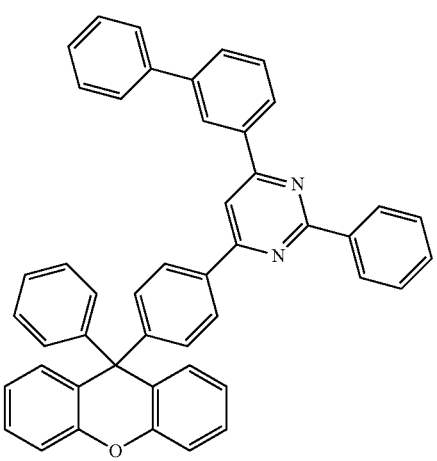
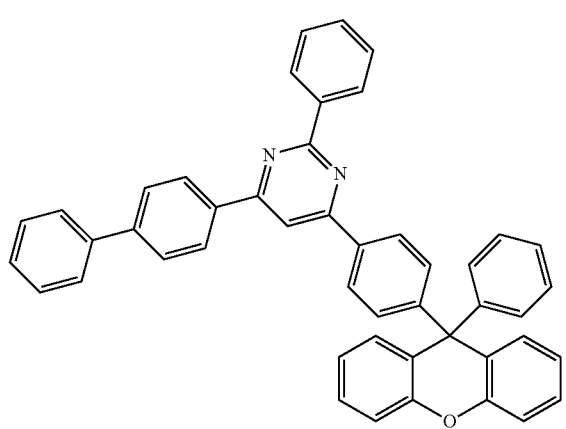
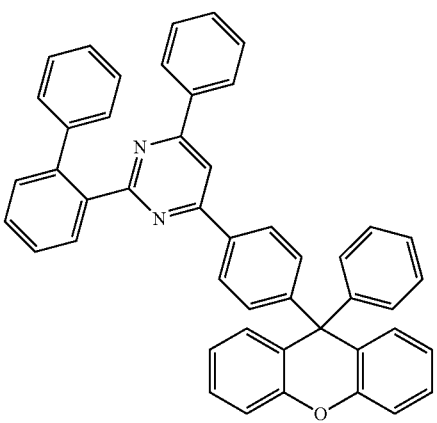

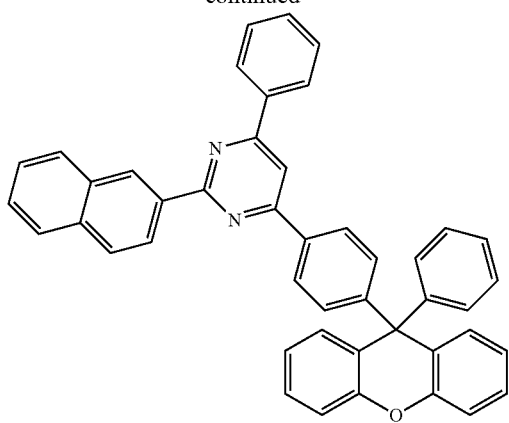
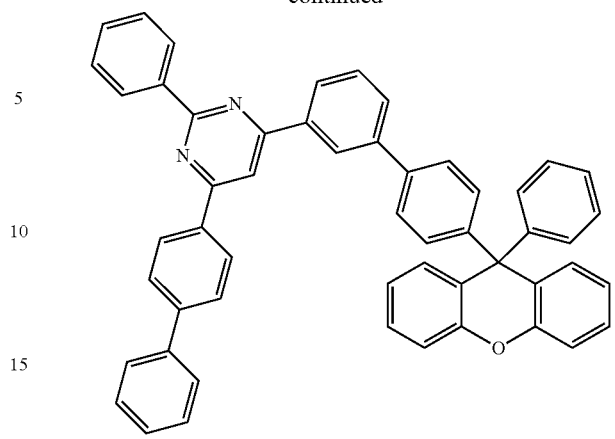

33
-continued
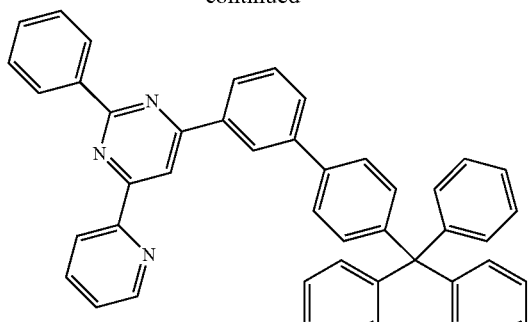
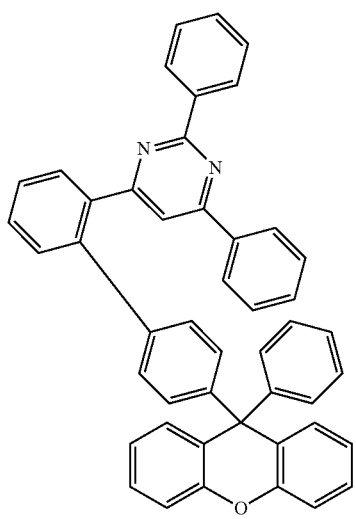
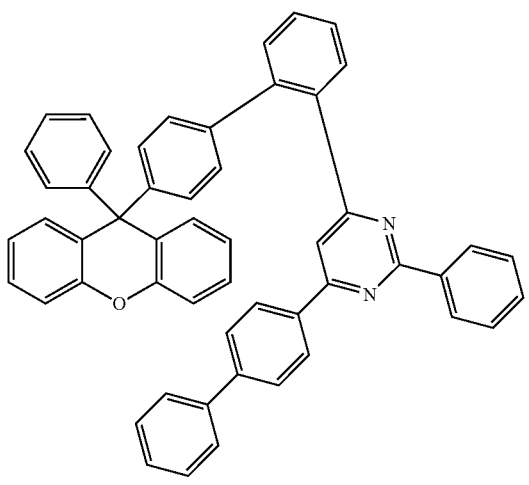
34
-continued
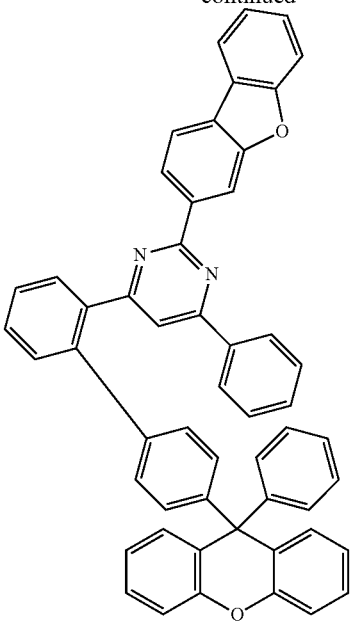
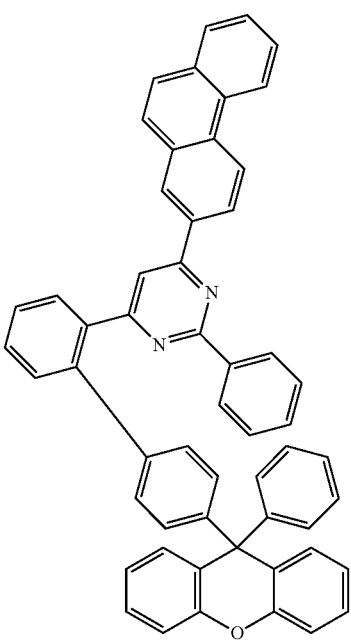
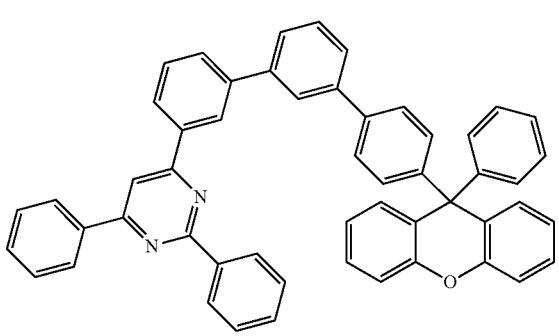

35
-continued
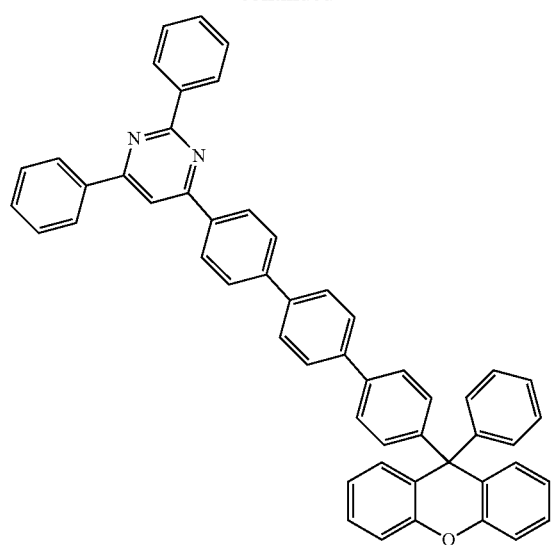 [SMILES: c1ccc(-c2cc(-c3ccc(-c4ccc(-c5ccc(C6(c7ccccc7)c7ccccc7Oc7ccccc76)cc5)cc4)cc3)nc(-c3ccccc3)n2)cc1]
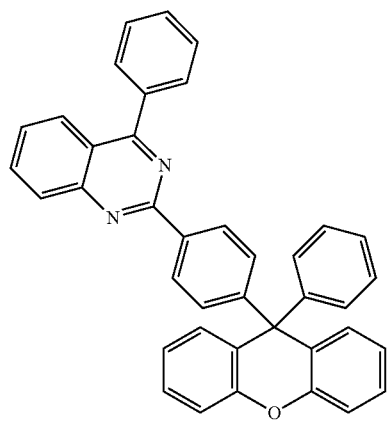
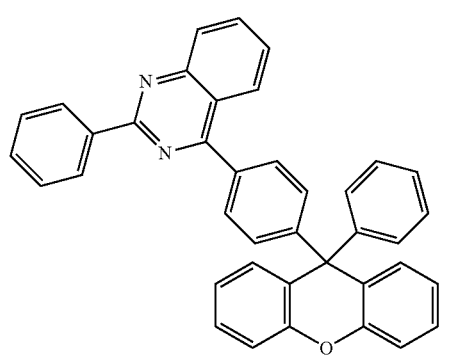
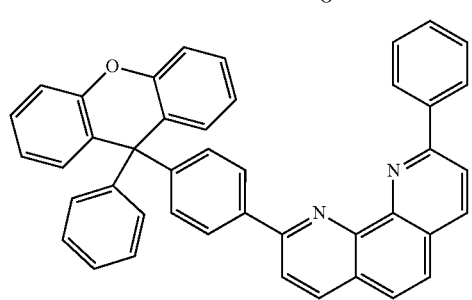
36
-continued
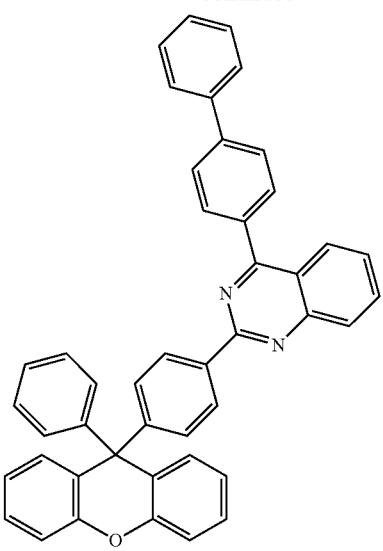
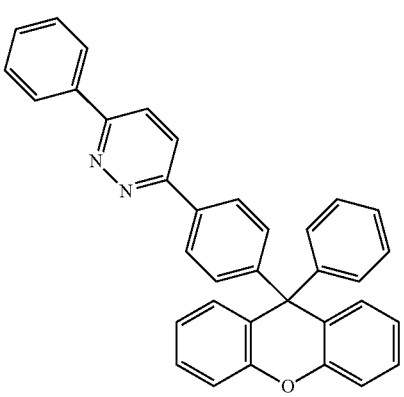
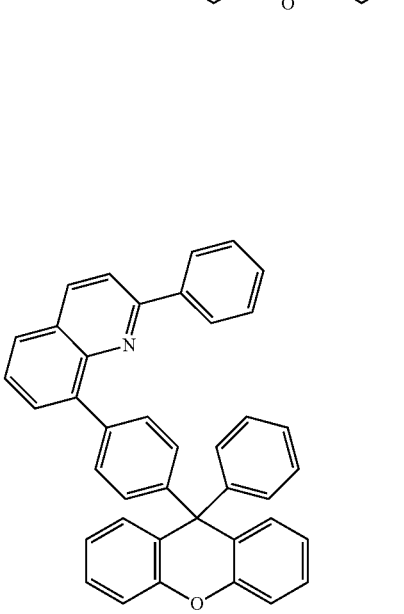

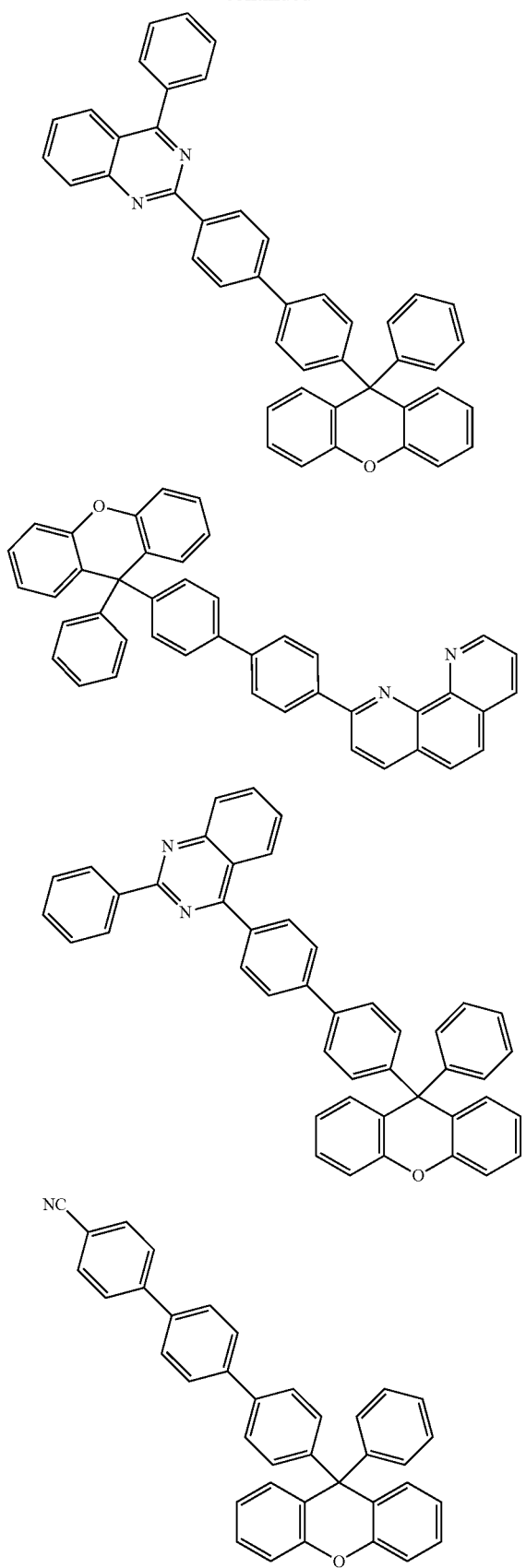
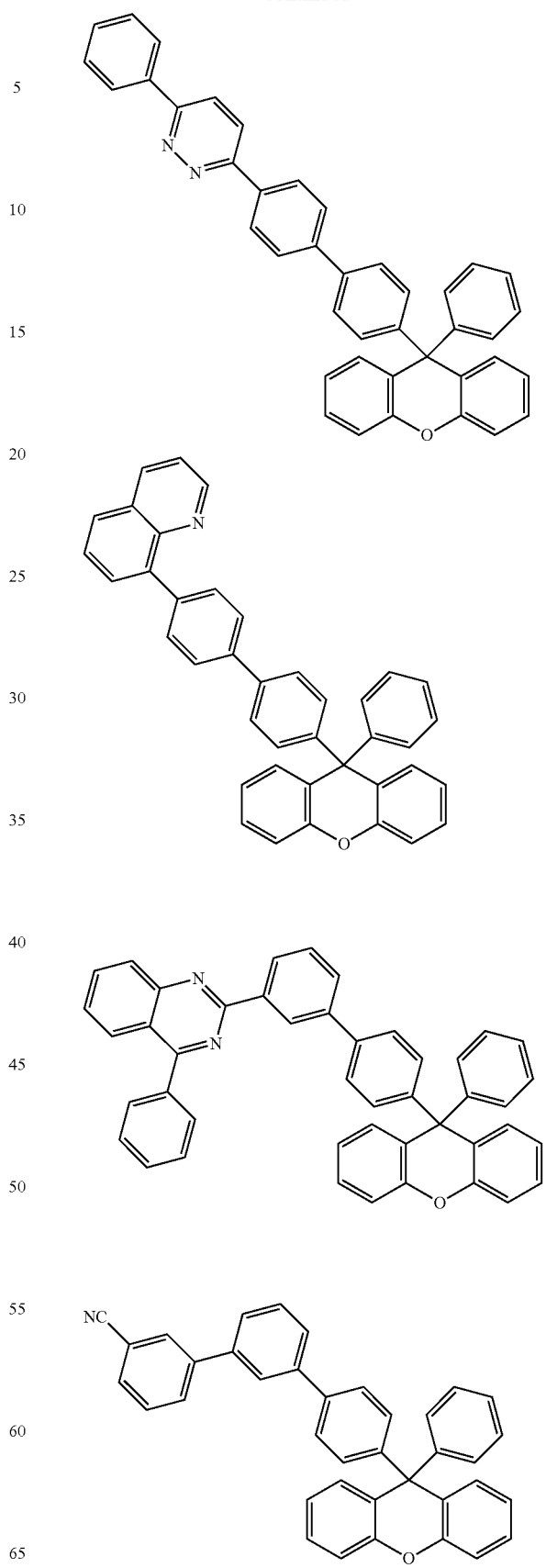

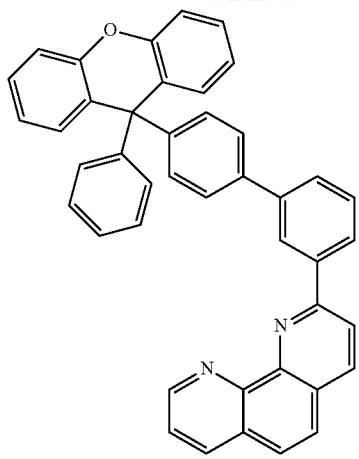
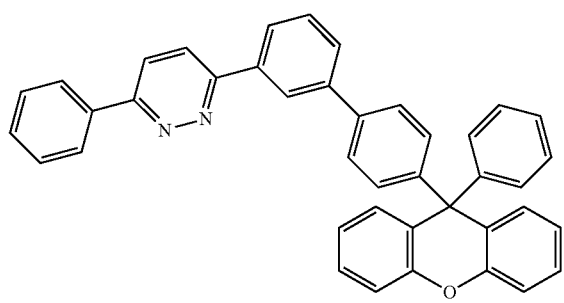
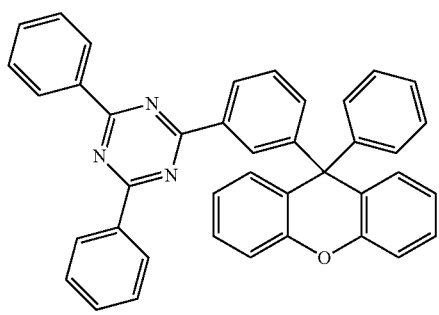
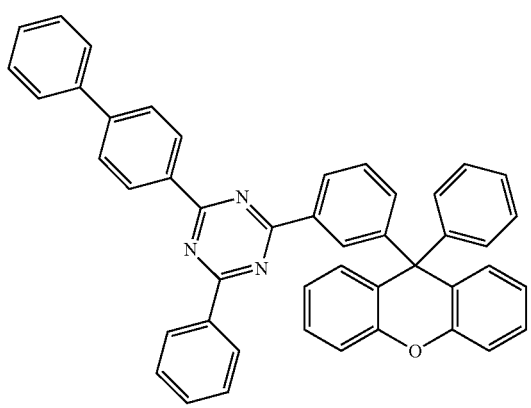
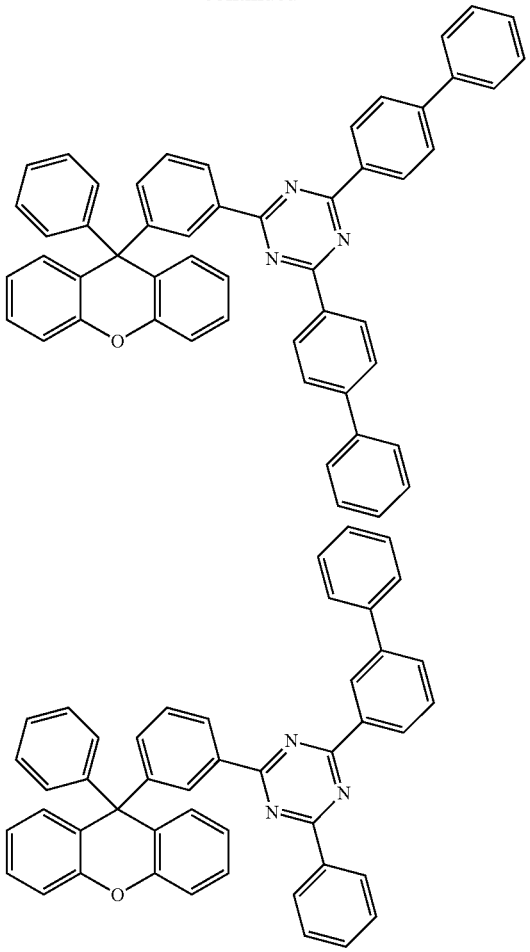
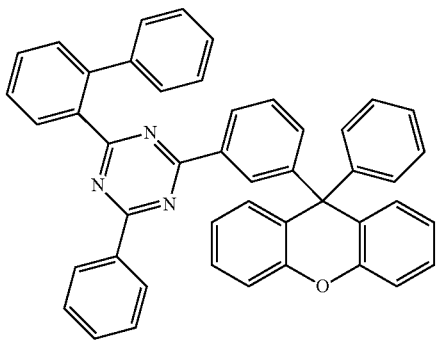
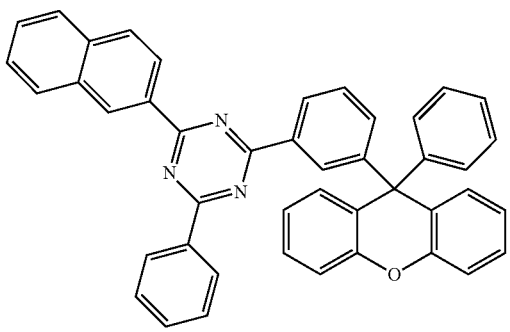

41
-continued
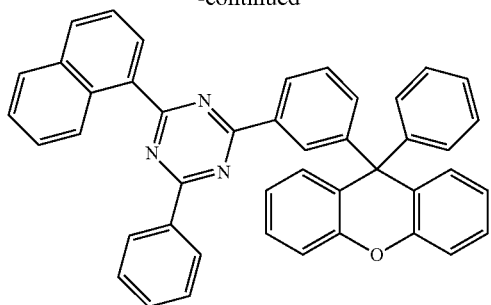
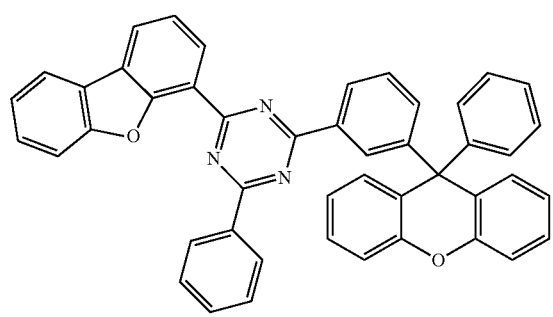
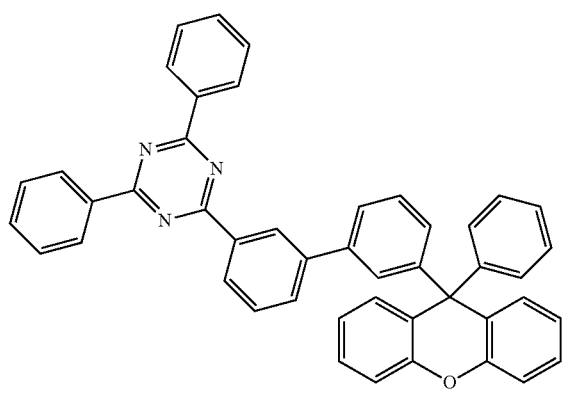
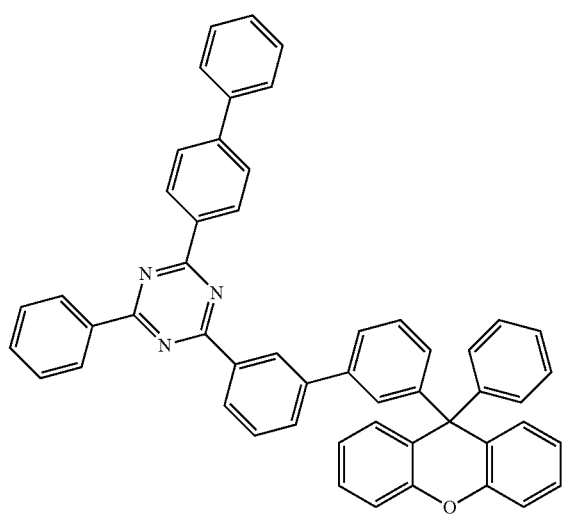
42
-continued
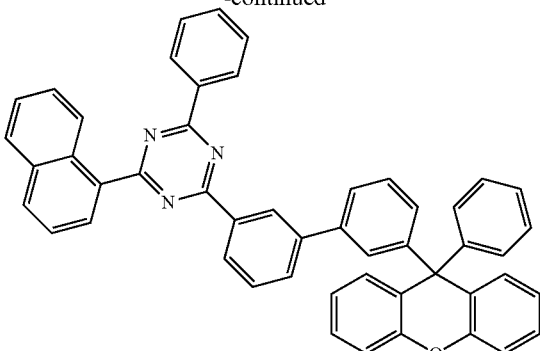
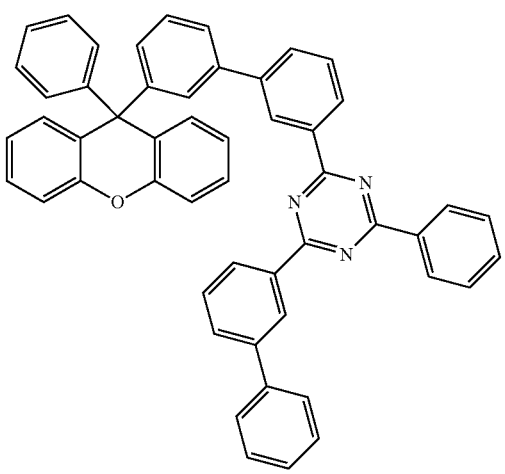
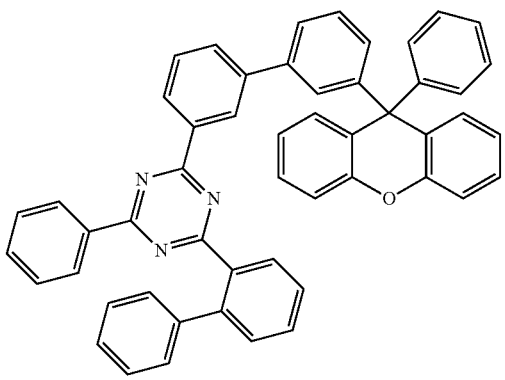
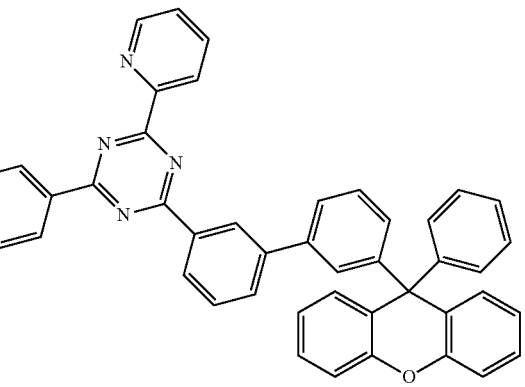

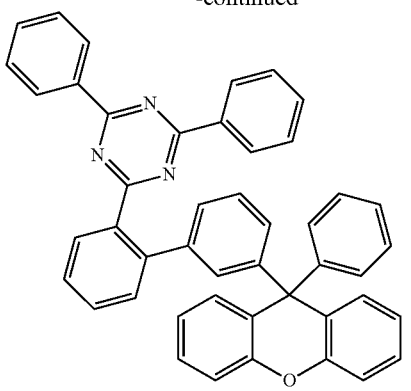
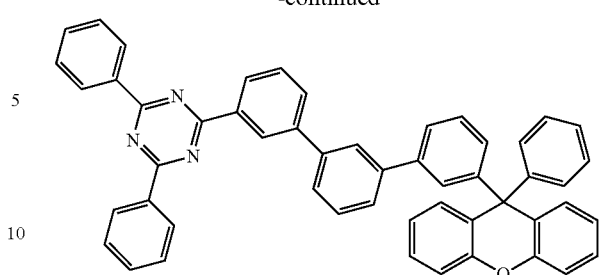
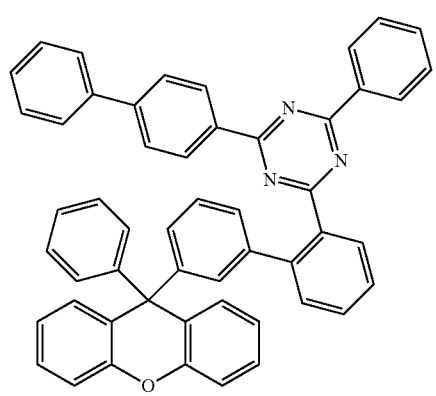
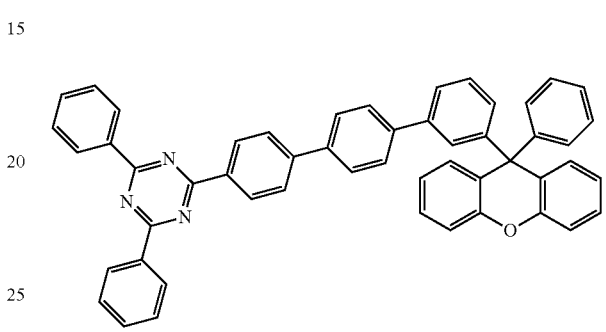
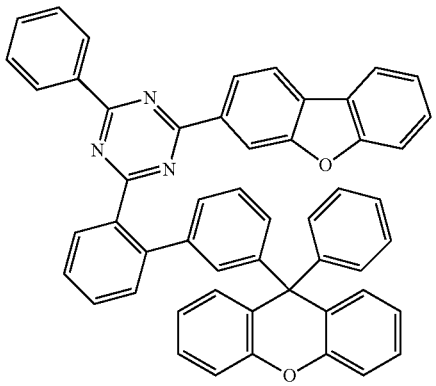
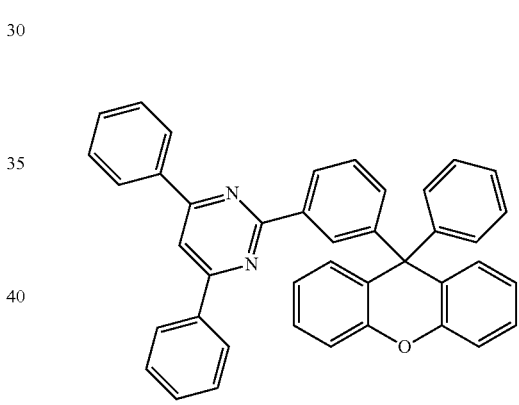
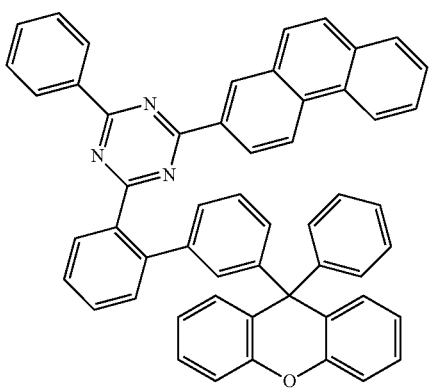
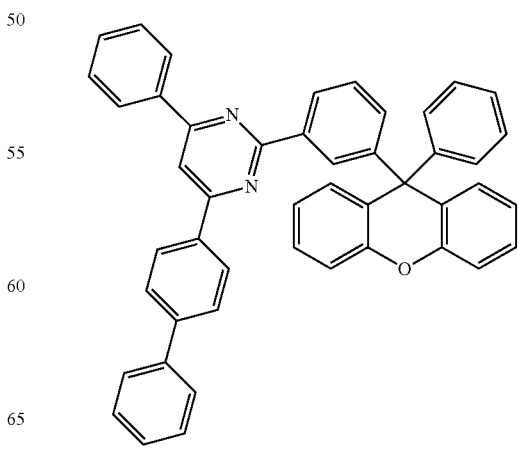

-continued
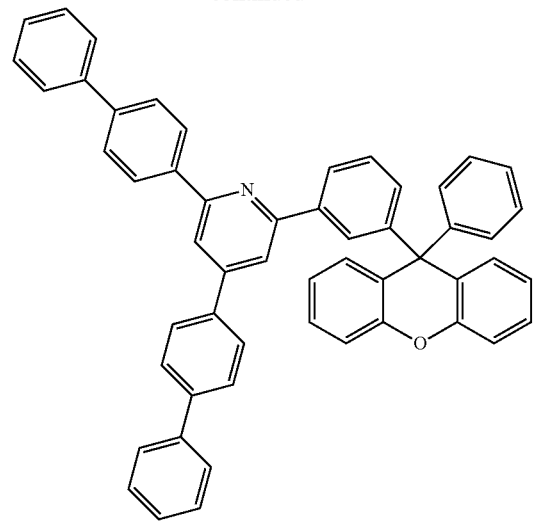
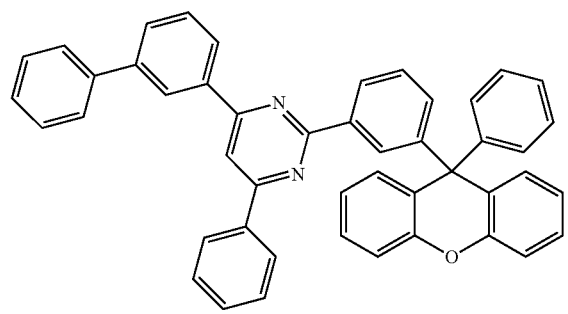
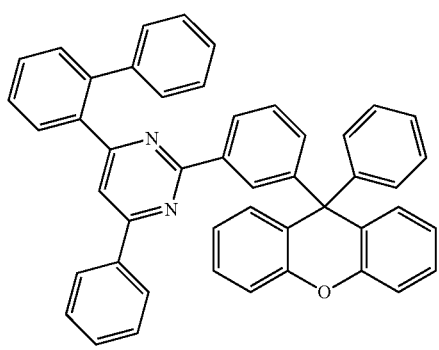
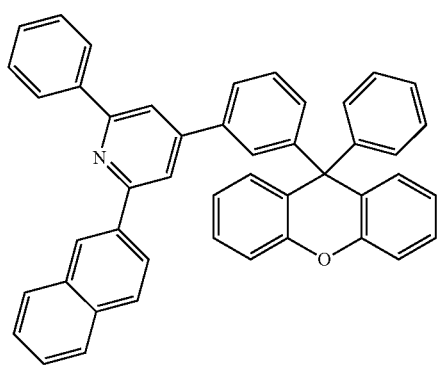
-continued
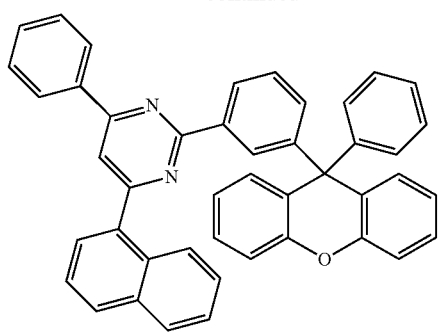
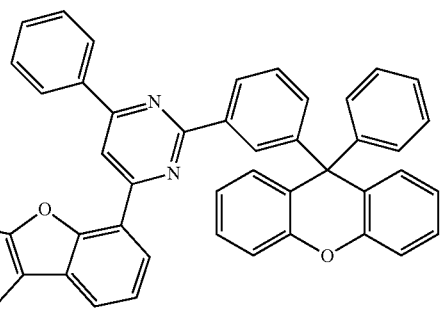
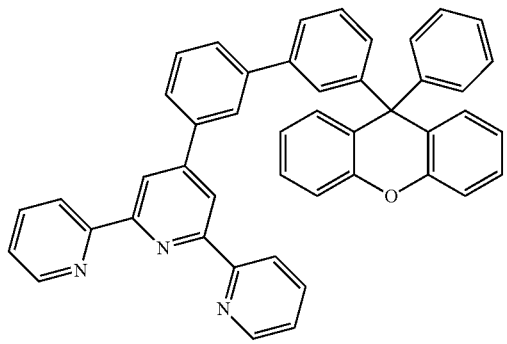
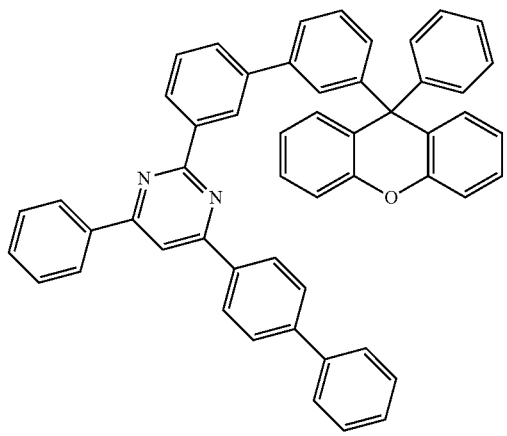

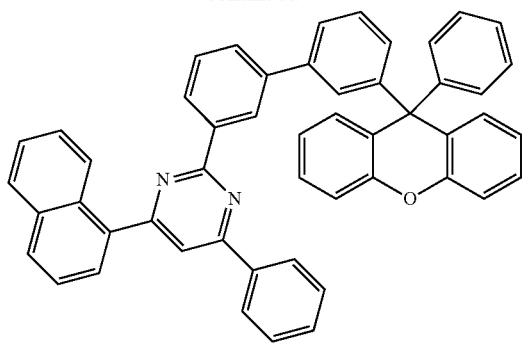
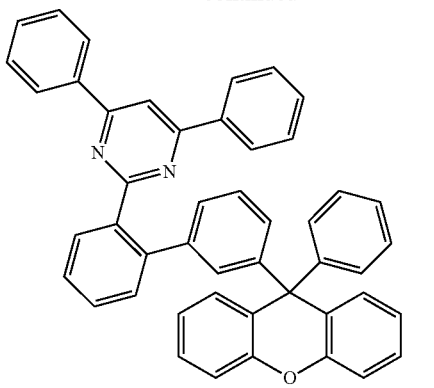
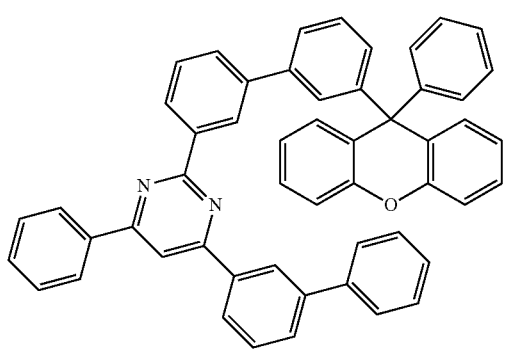
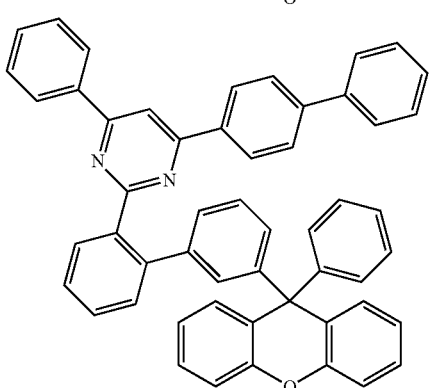
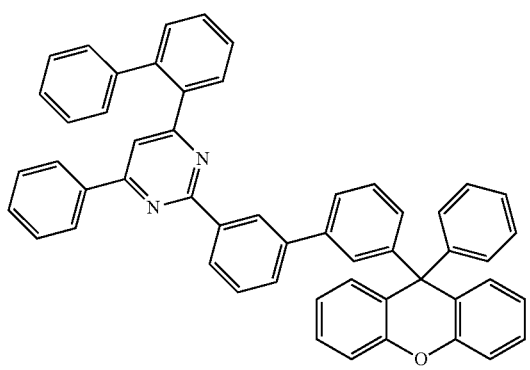
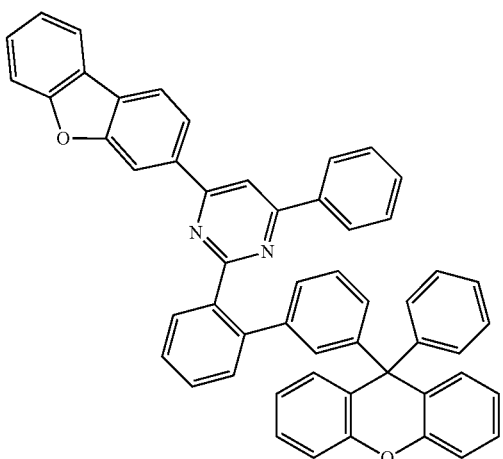
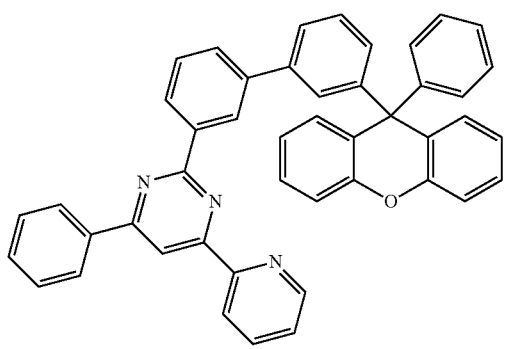
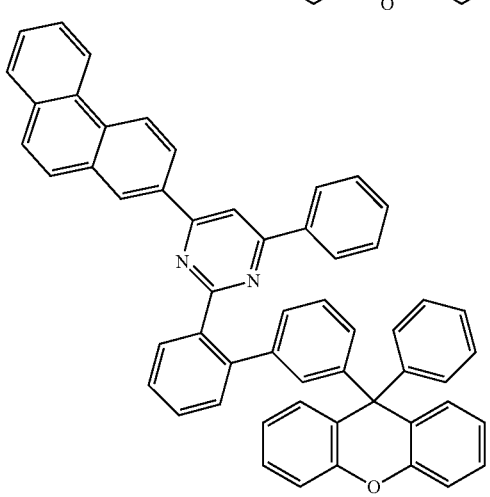

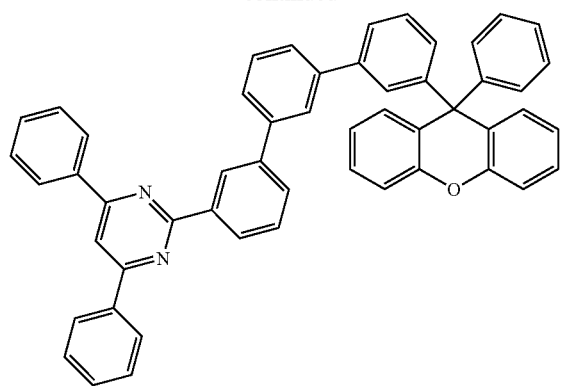
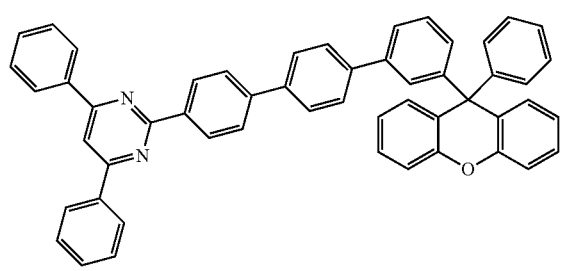
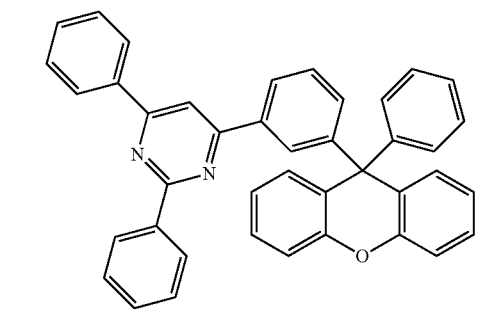
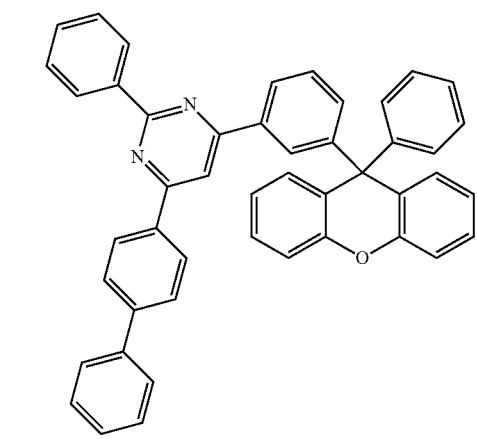
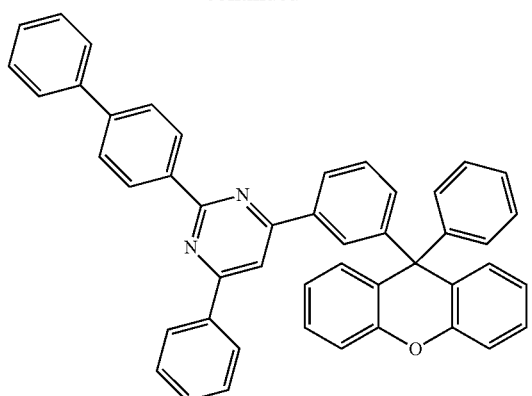
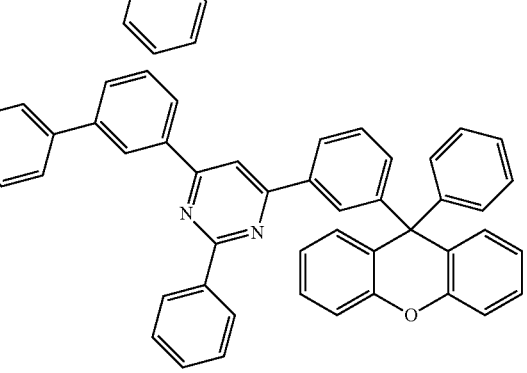
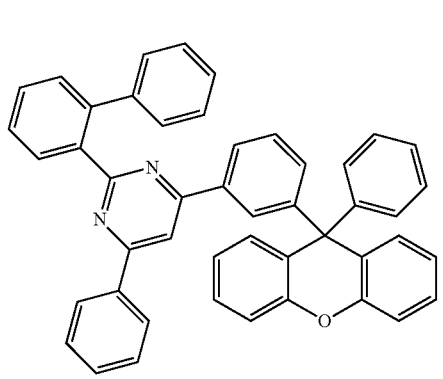
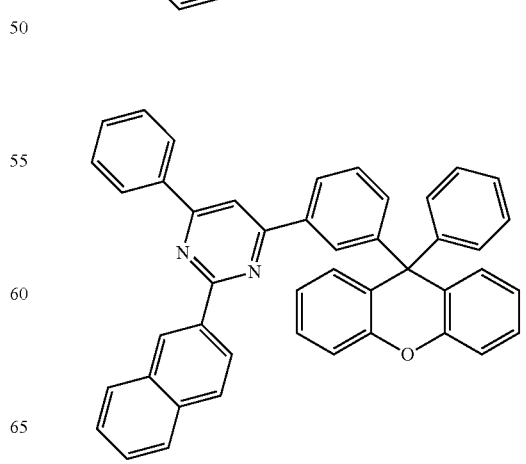

51
-continued
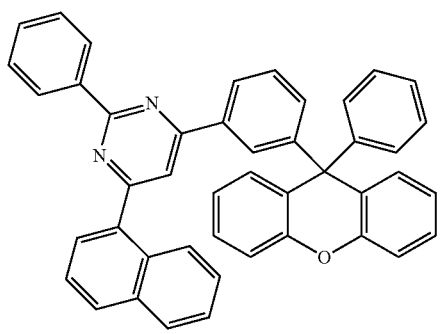
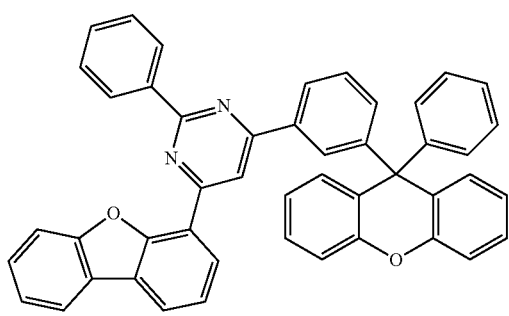
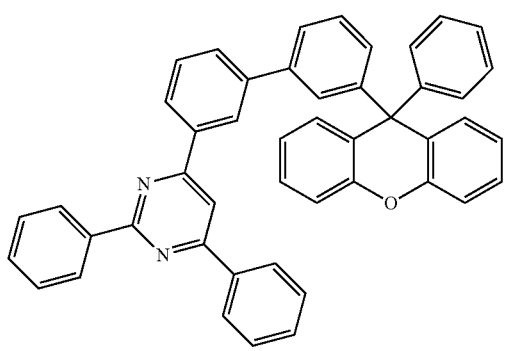
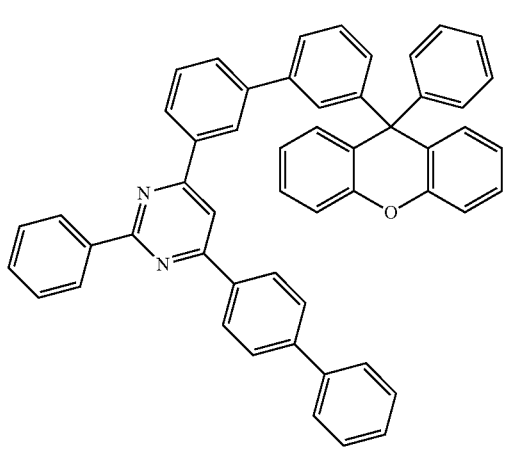
52
-continued
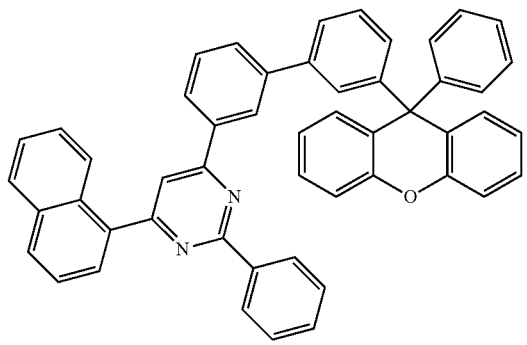
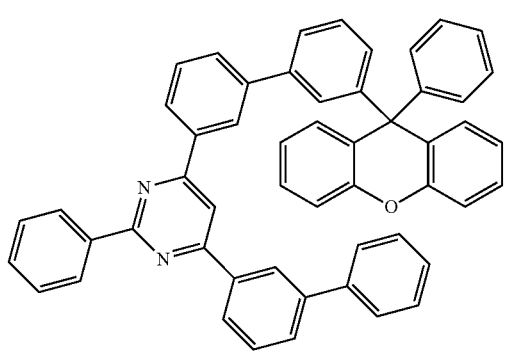
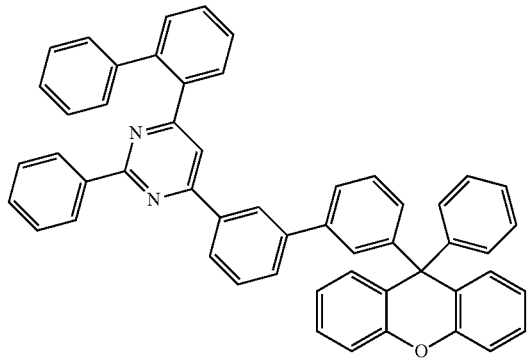
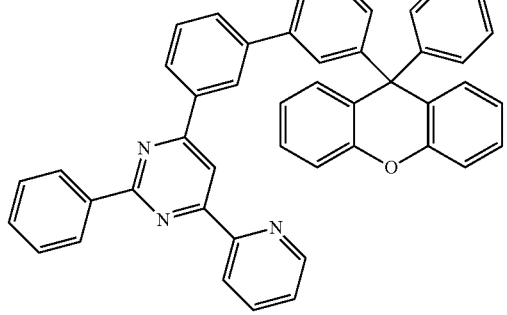

53
-continued
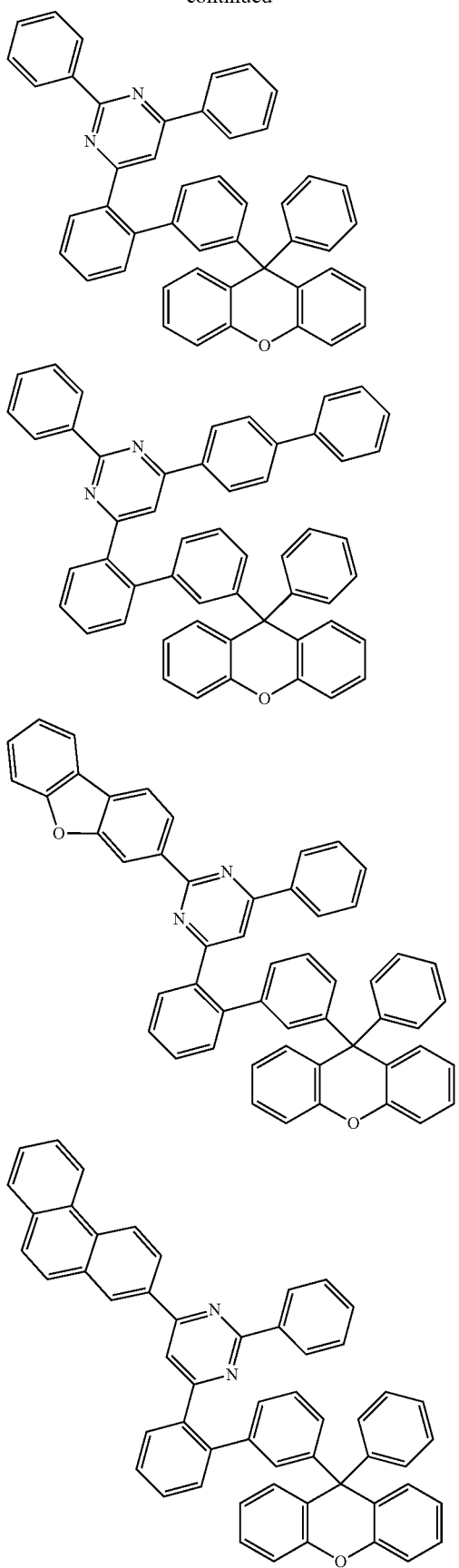
54
-continued
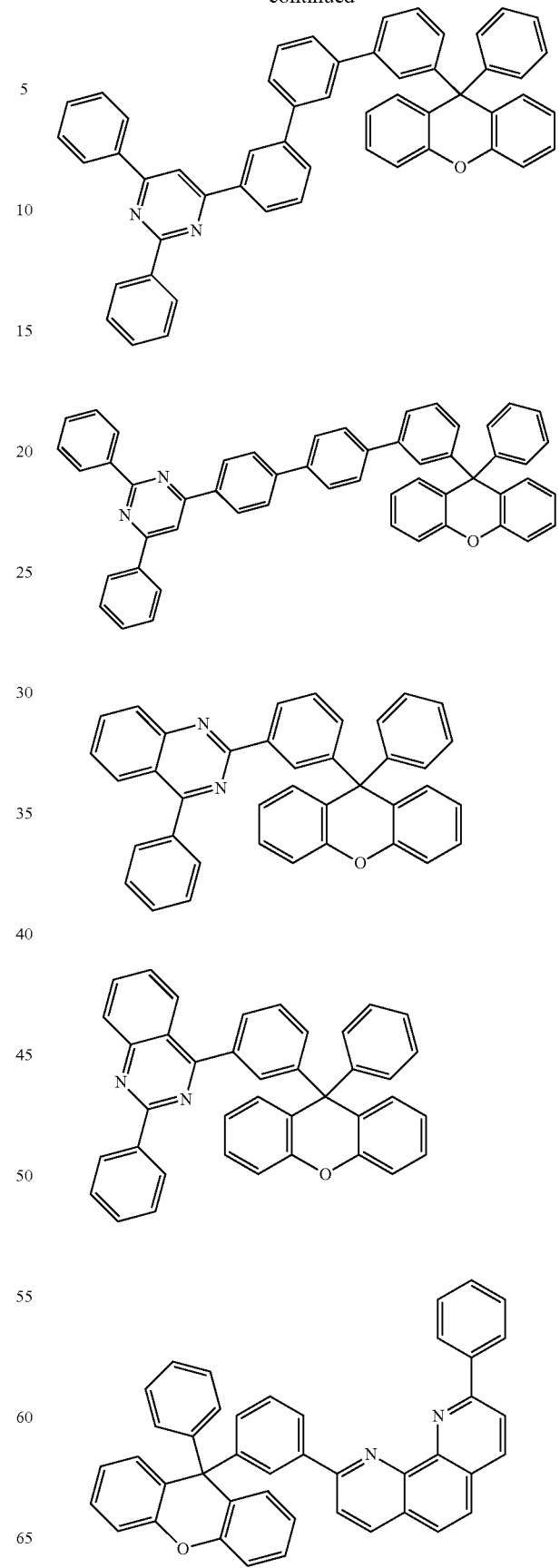

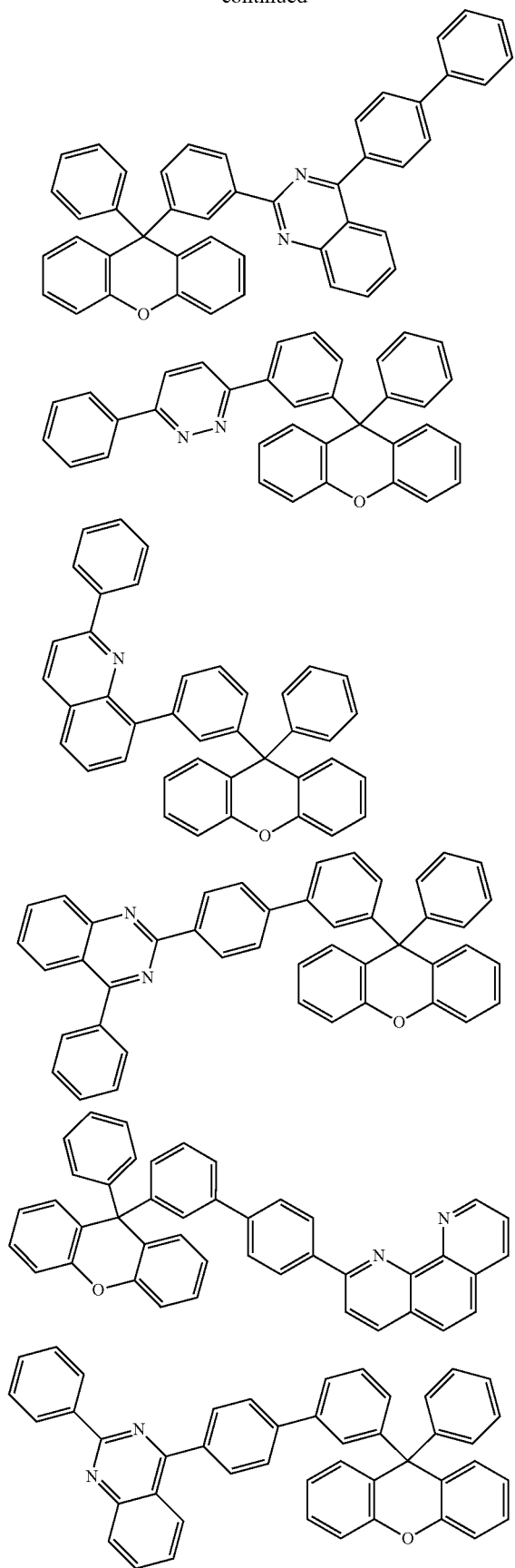
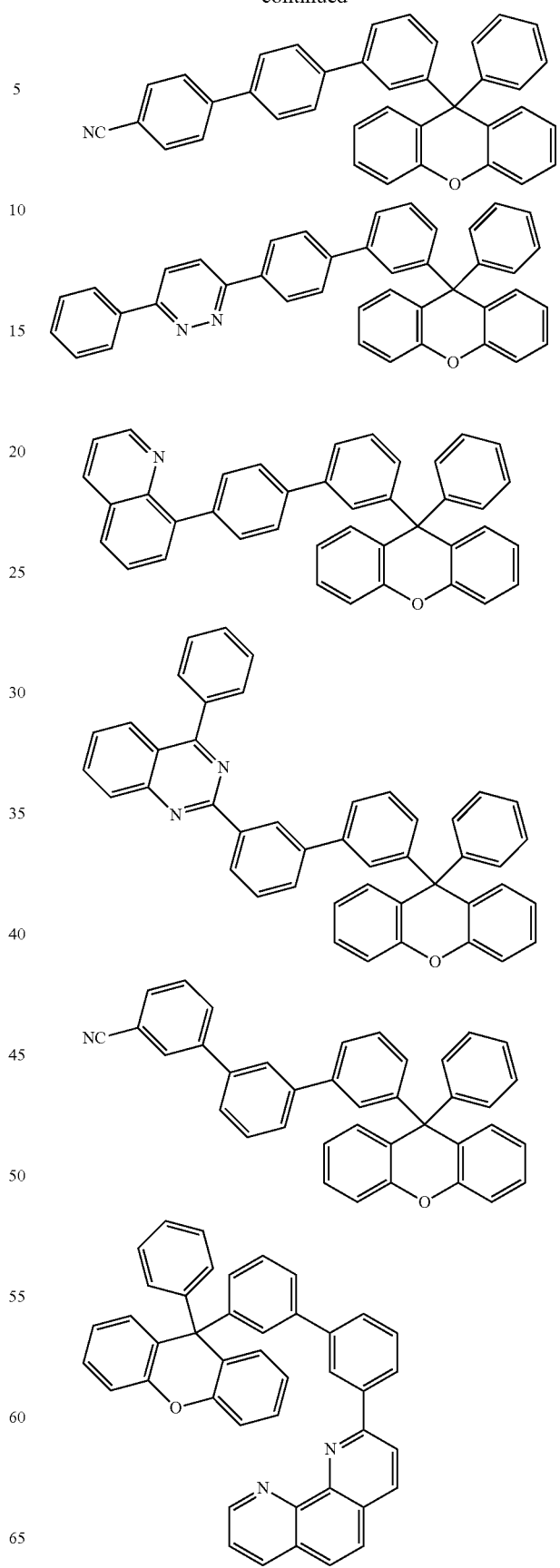

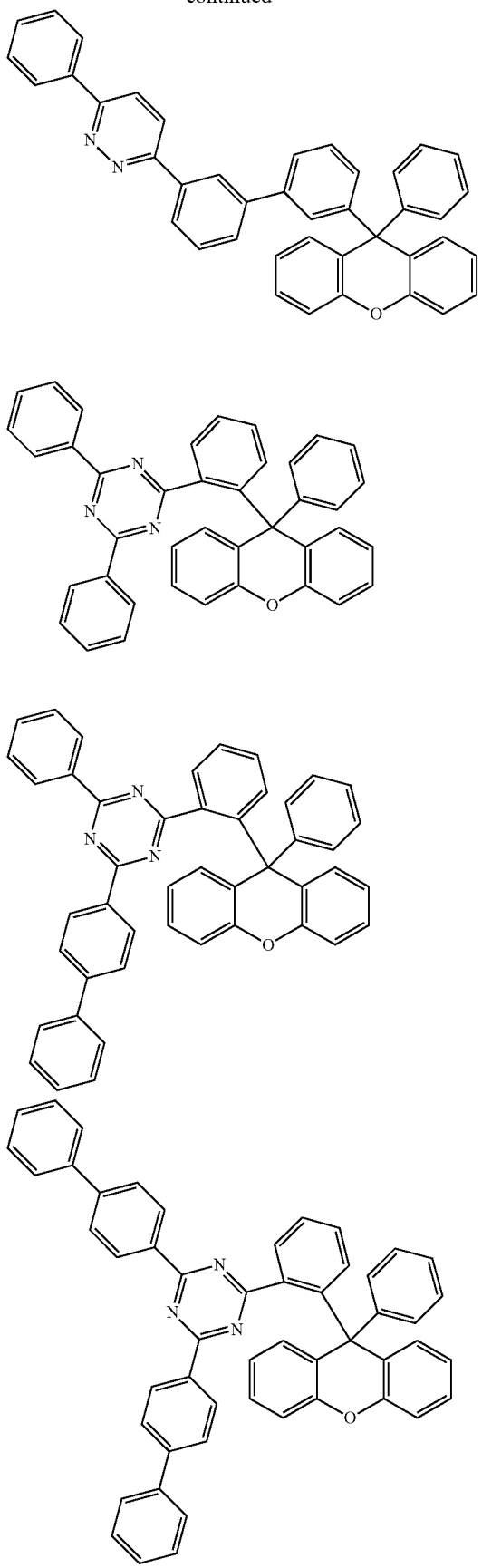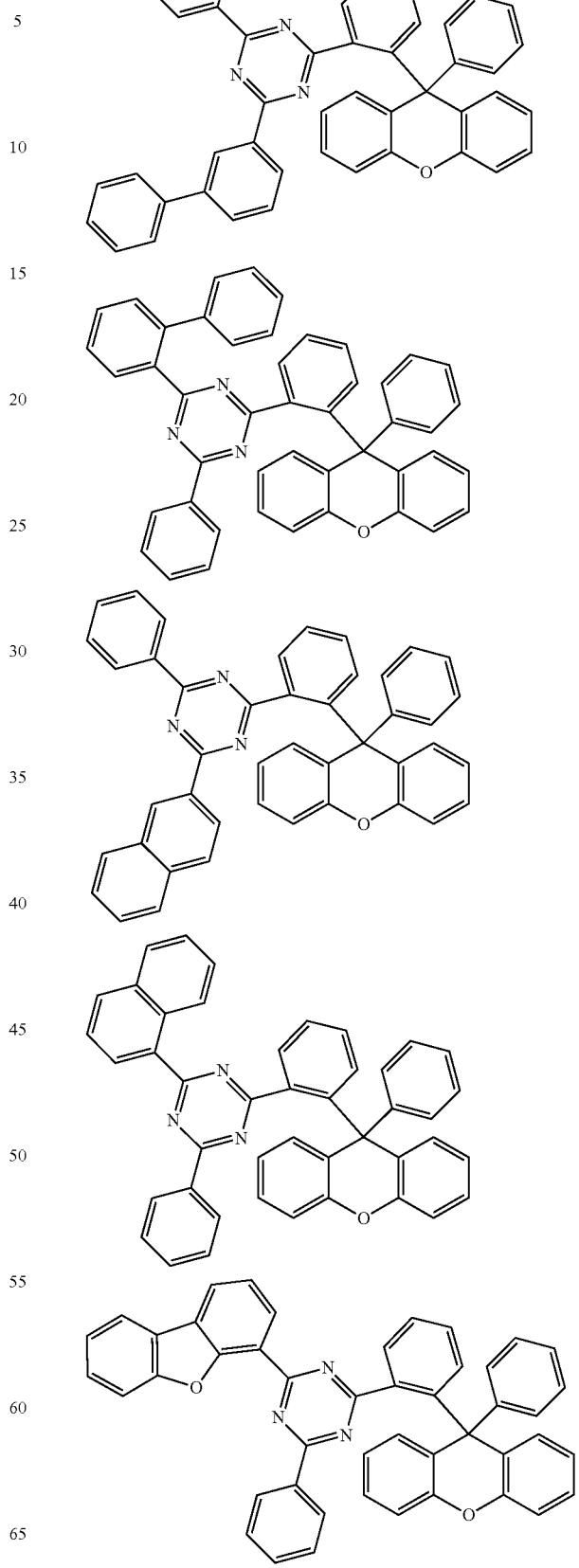

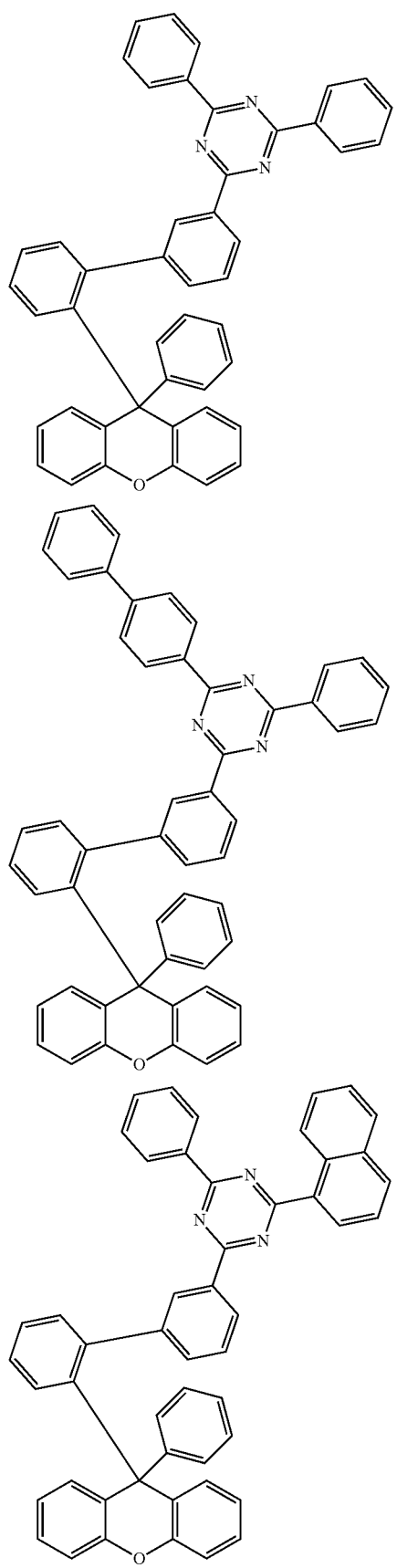
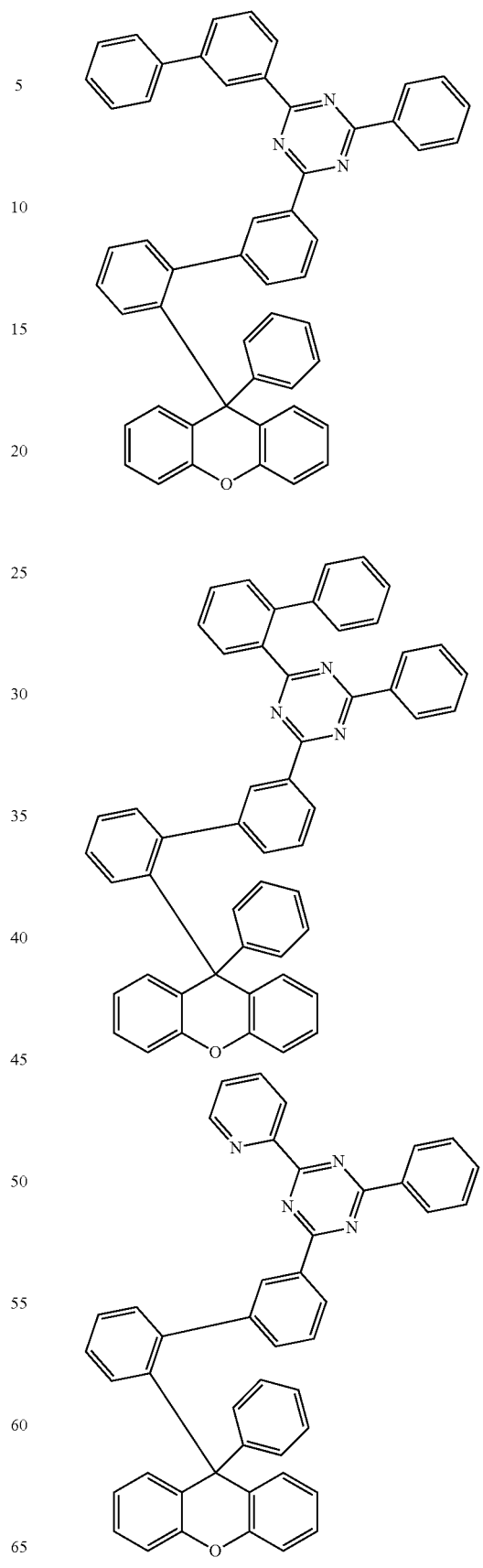

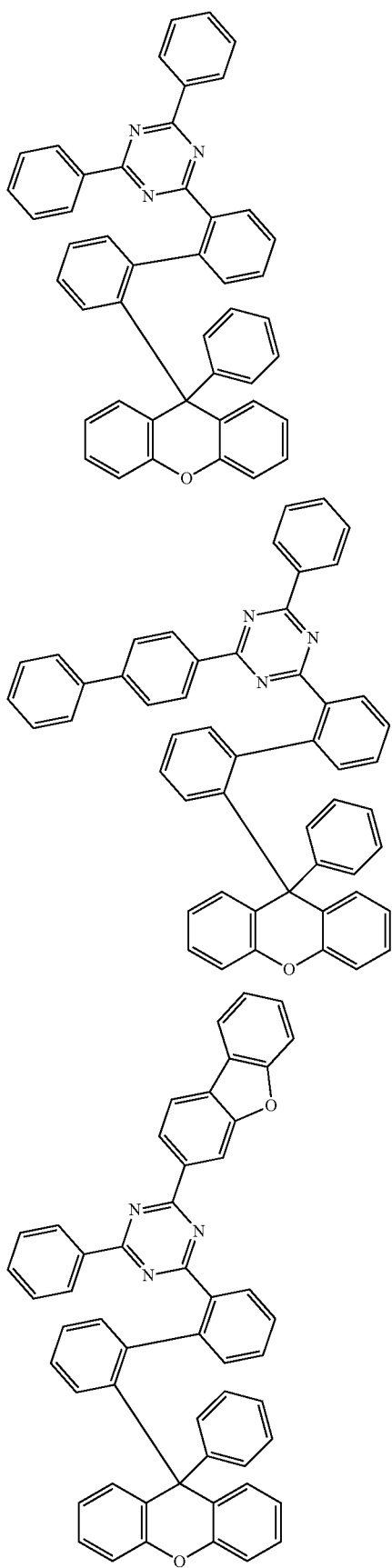
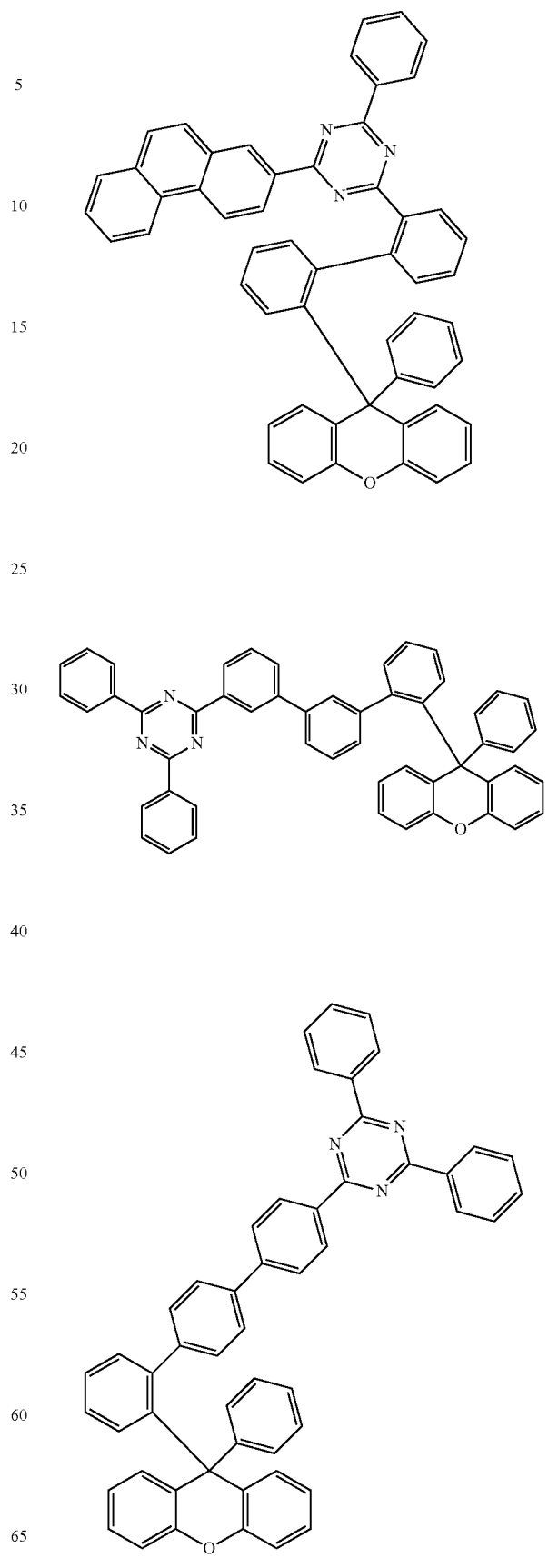

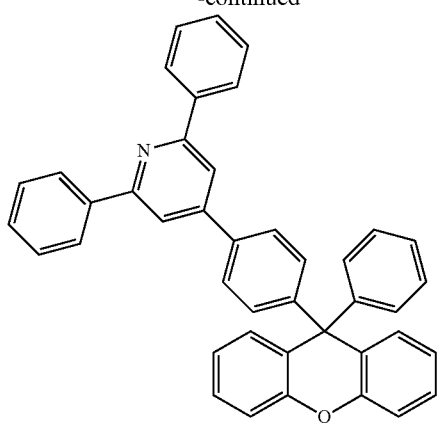
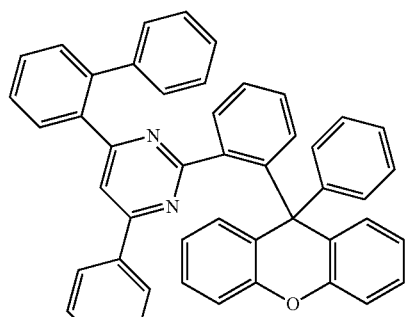
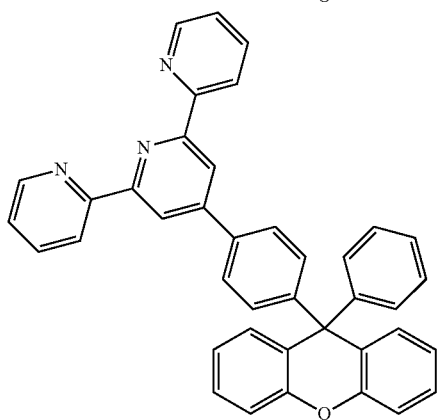
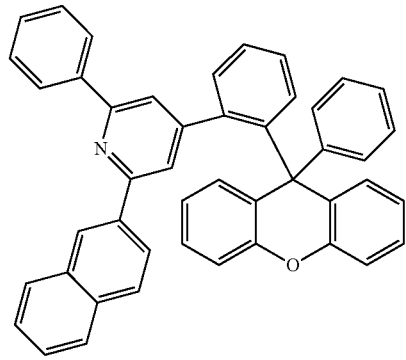
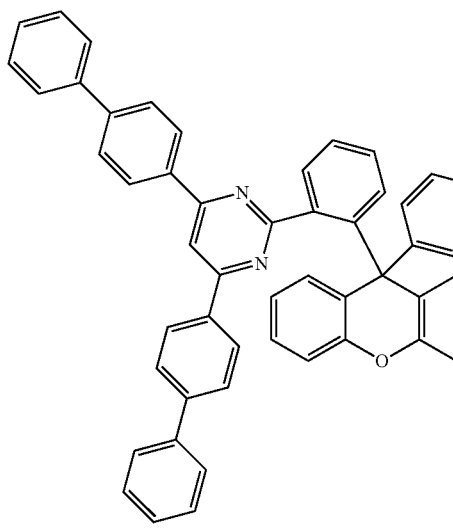
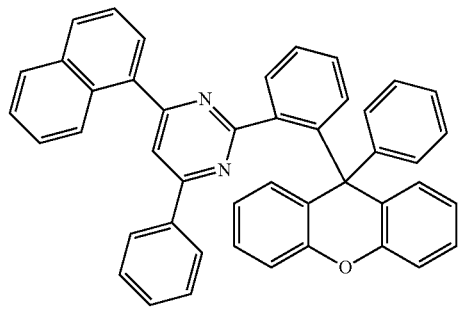
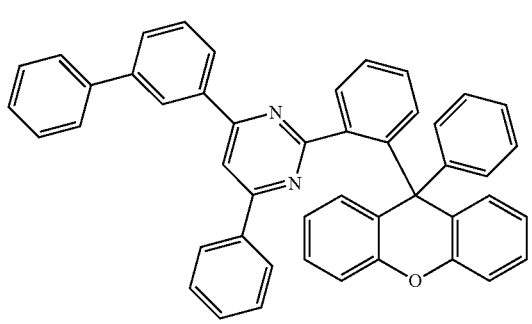
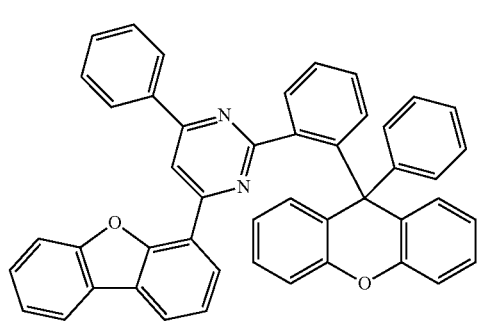

65
-continued
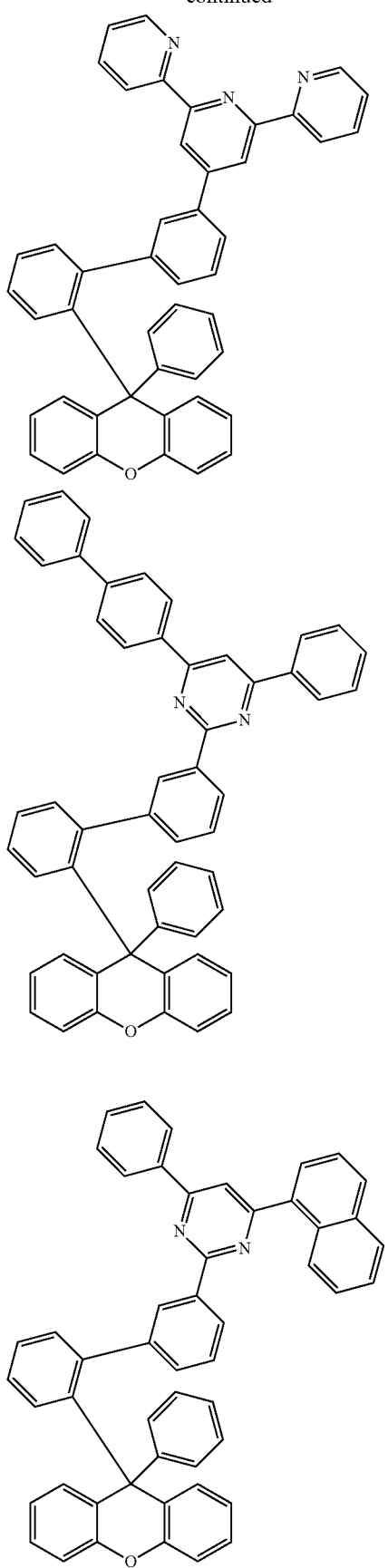
66
-continued
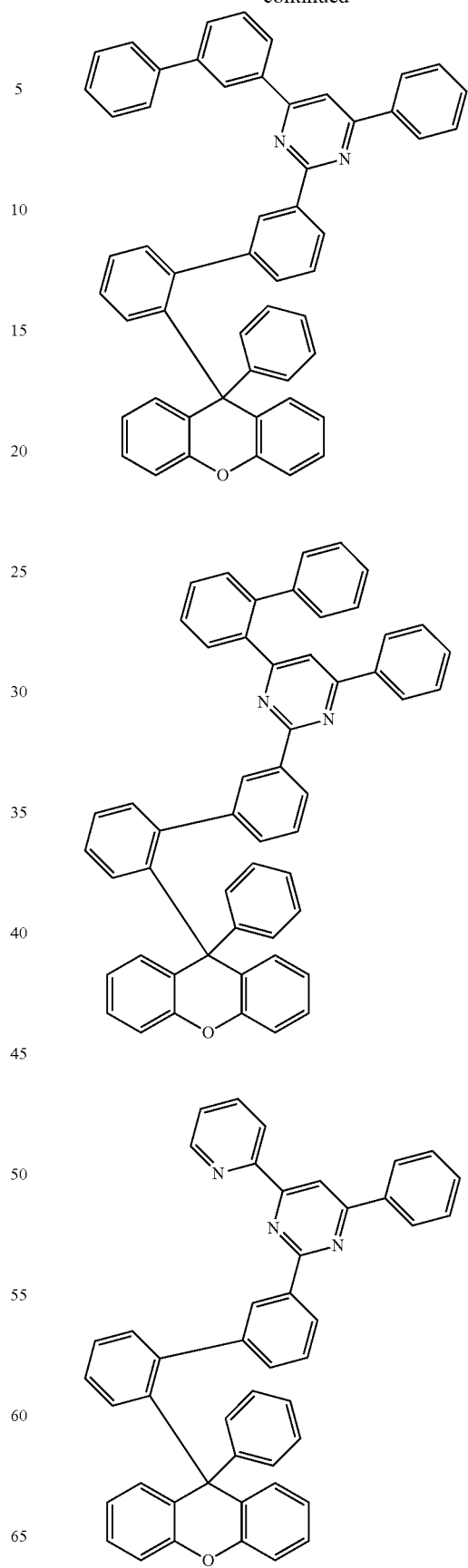

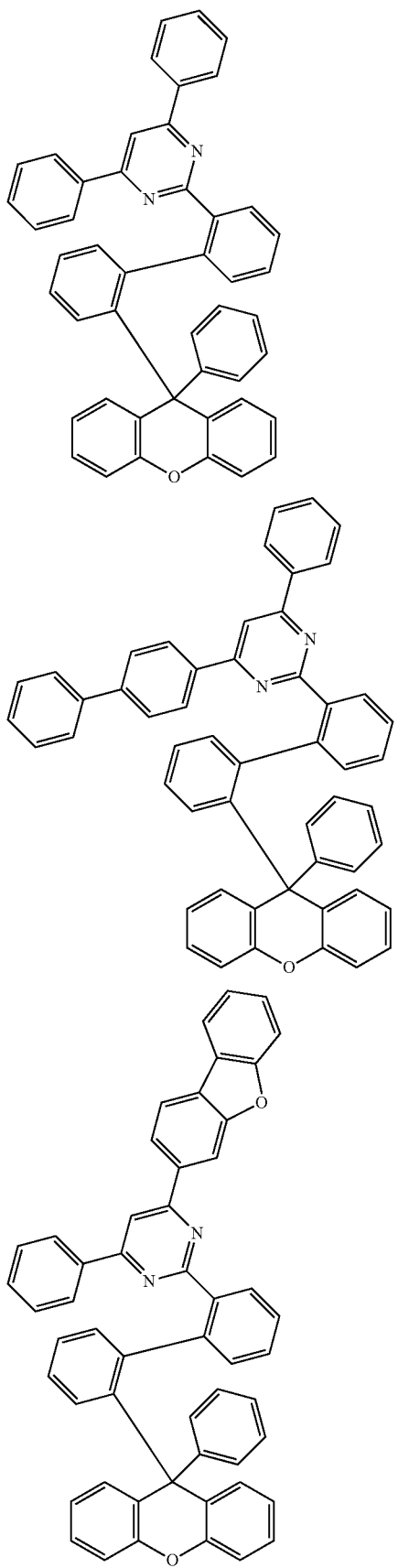
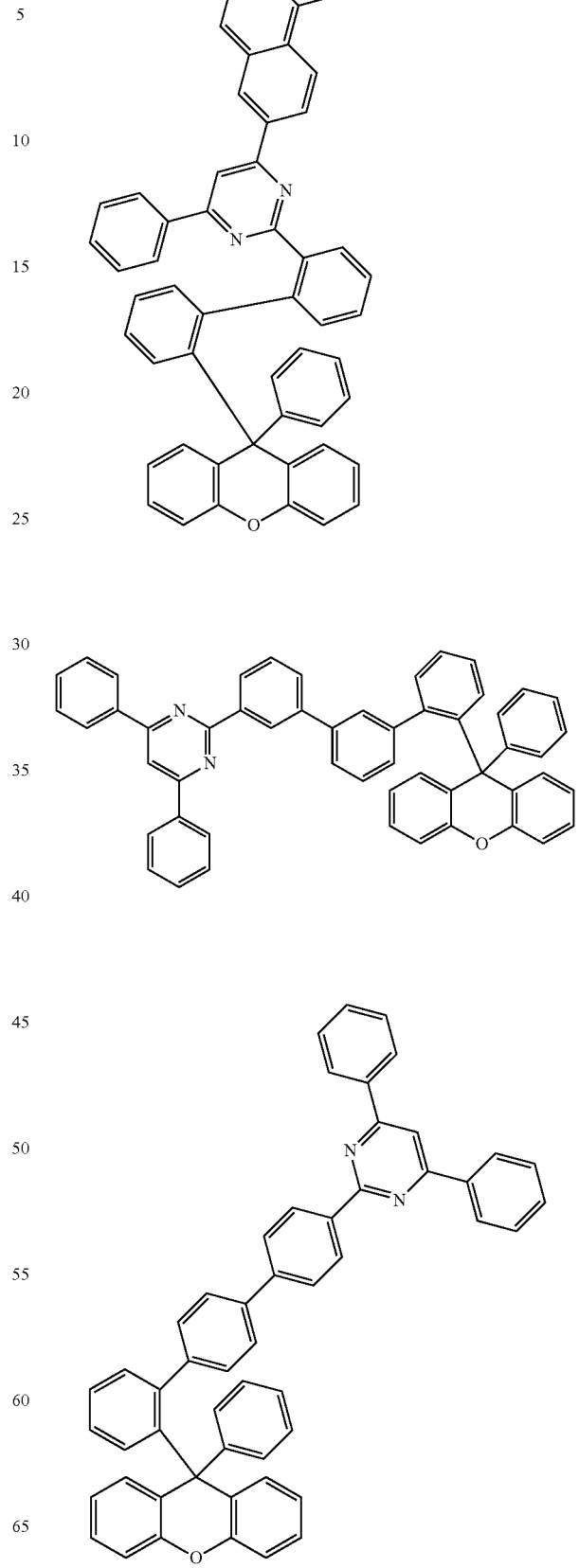

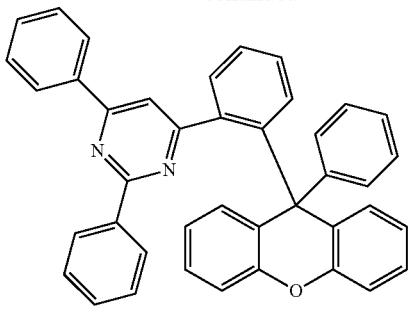
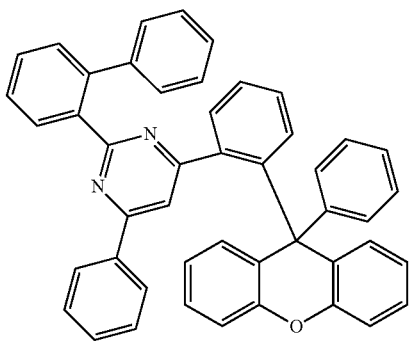
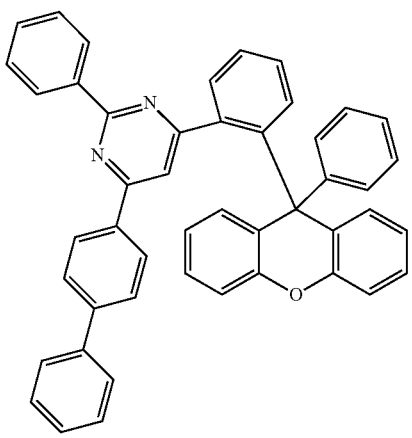
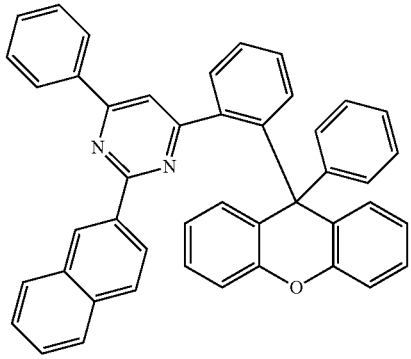
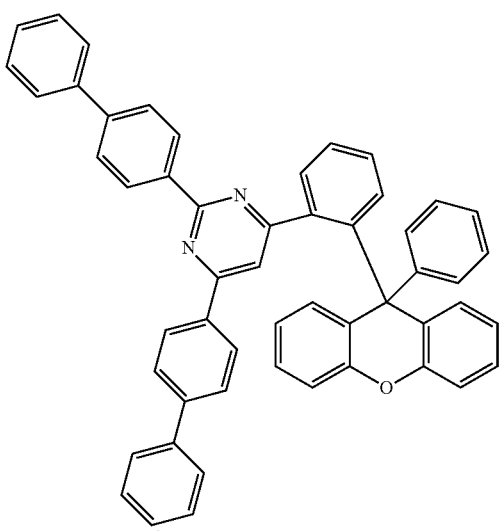
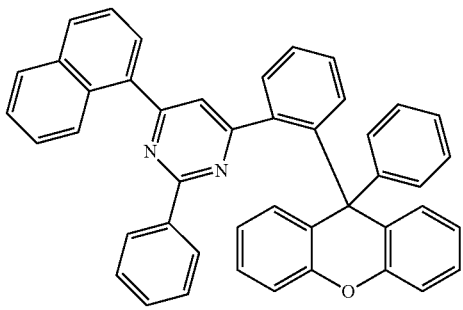
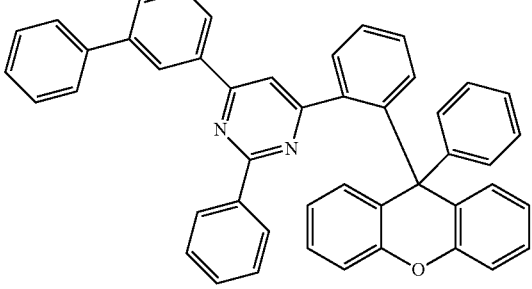
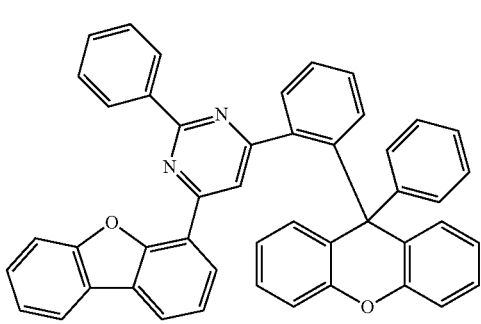

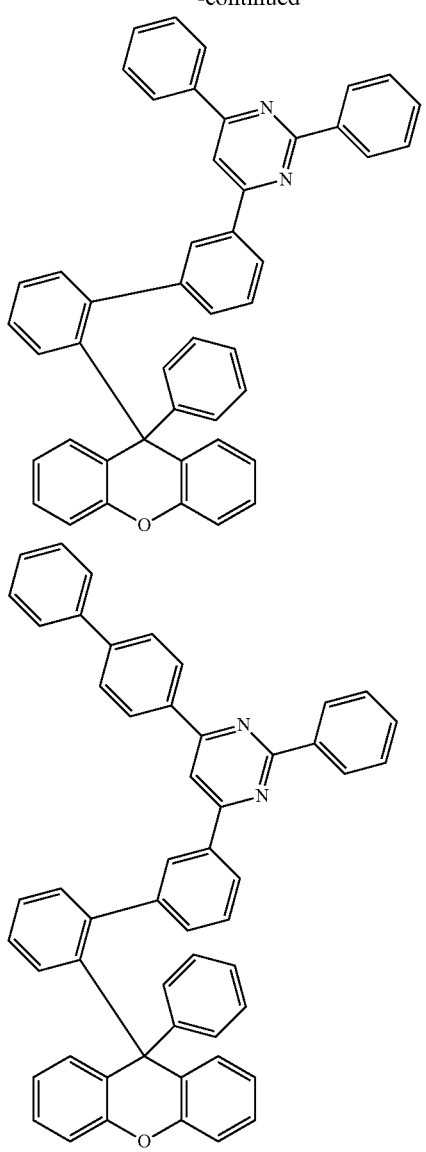
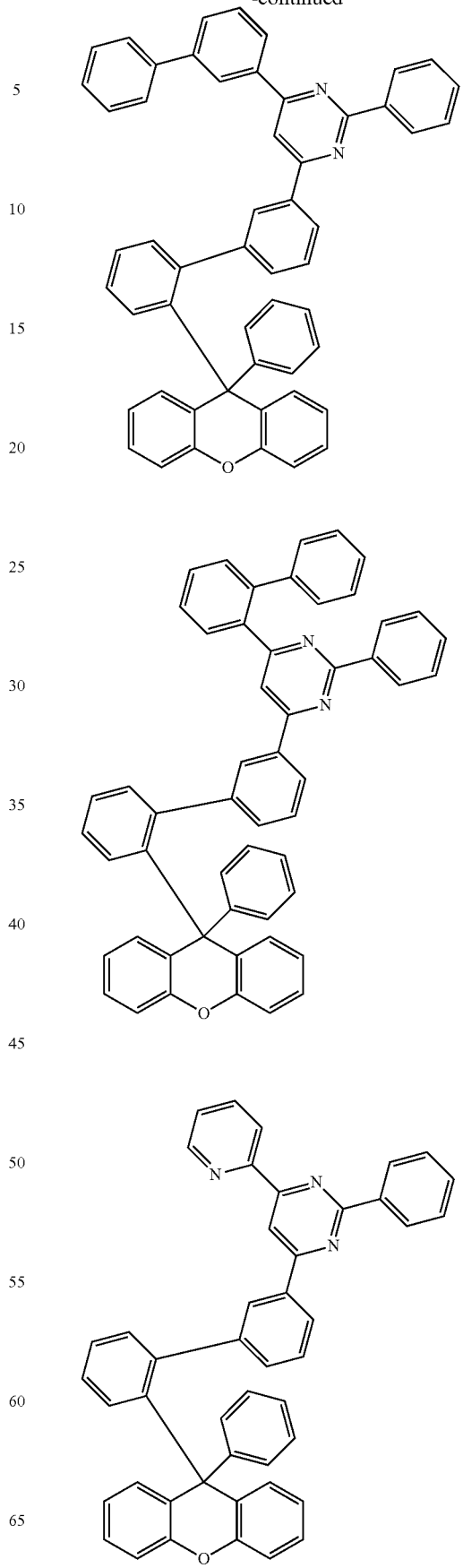

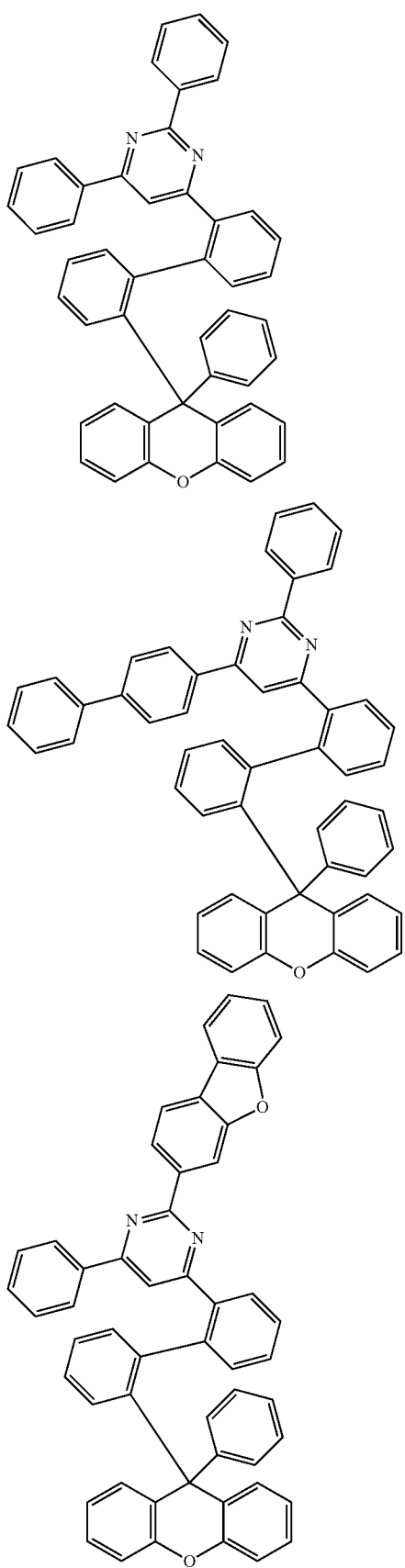
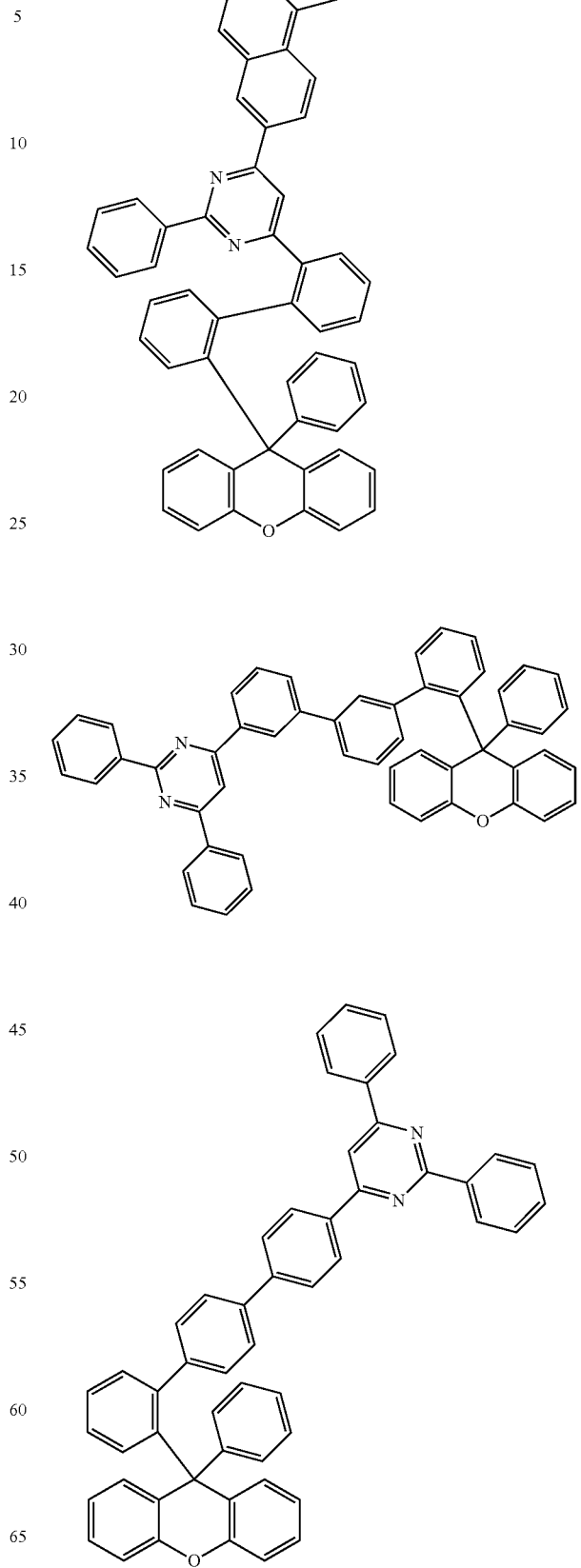

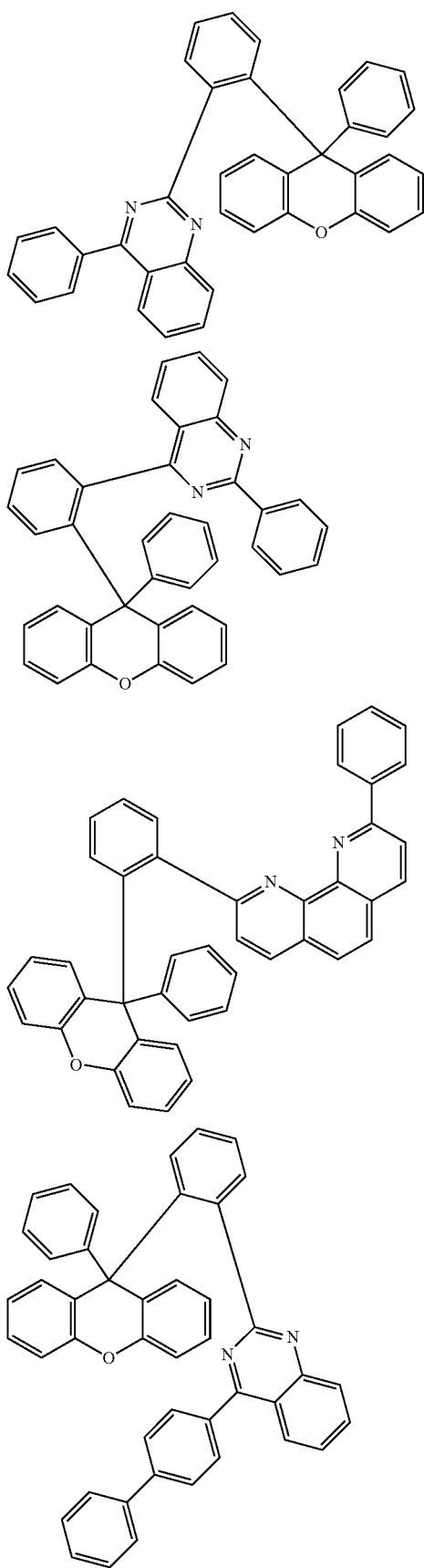
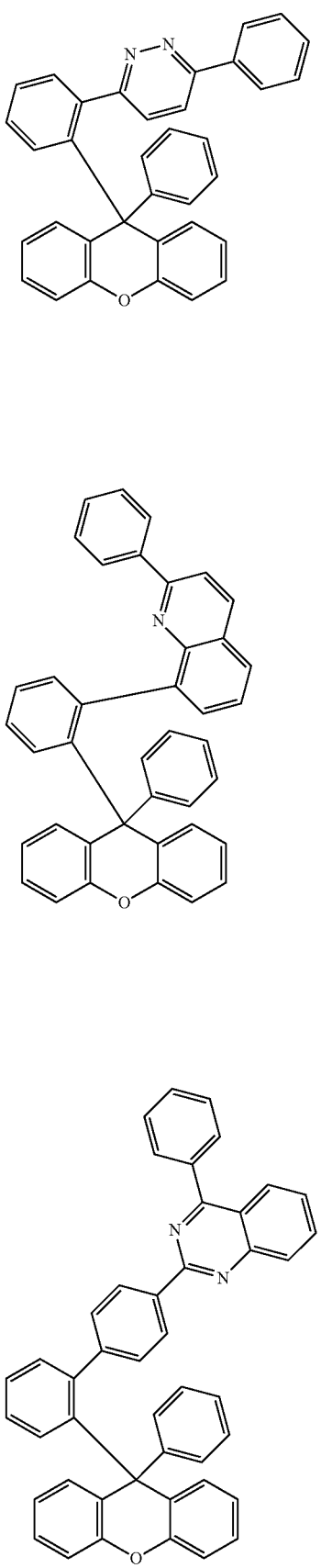

77
-continued
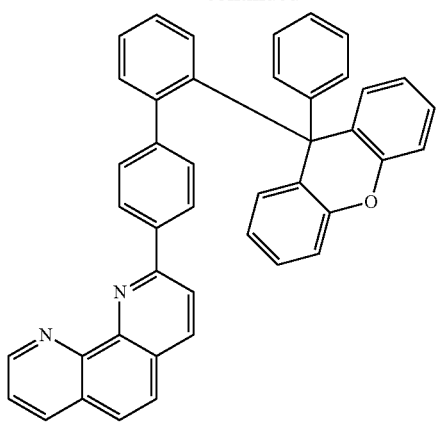
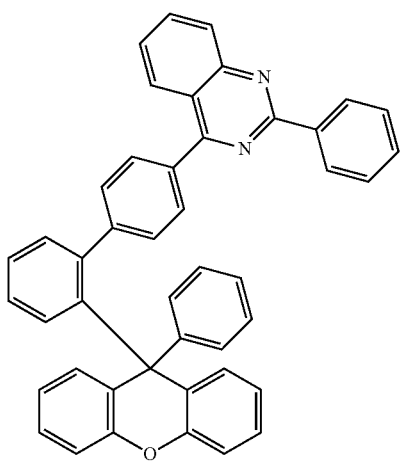
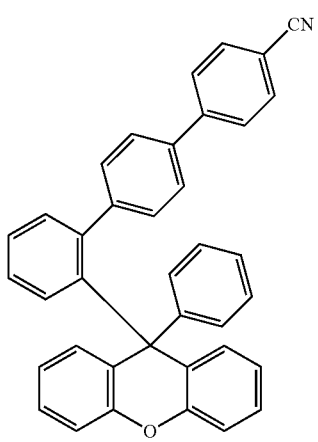
78
-continued
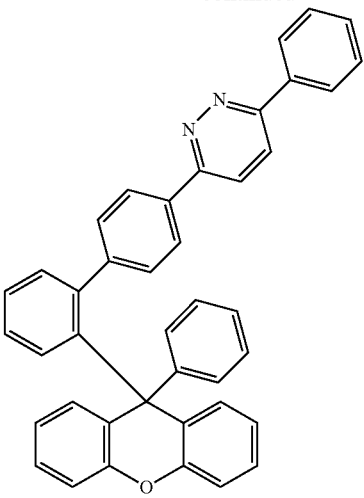
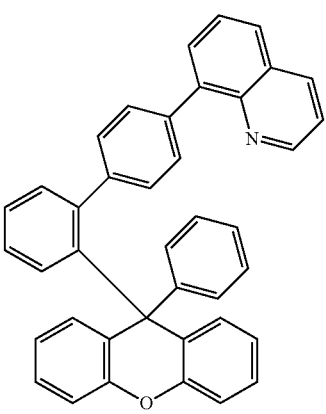

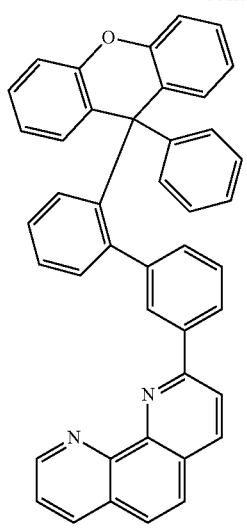

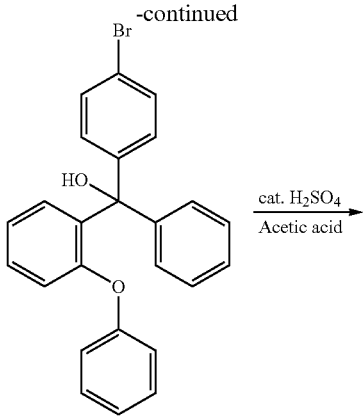

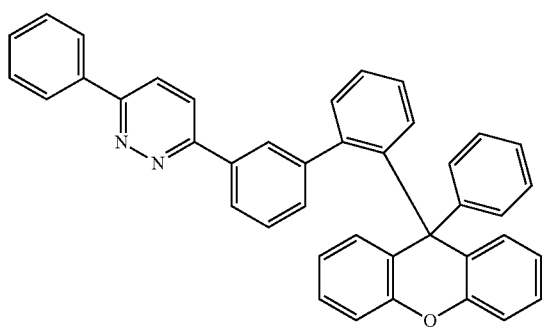

The compound according to an exemplary embodiment of the present application may be prepared by a preparation method to be described below.

For example, a core structure of the compound of Chemical Formula 1 may be prepared as in the following Reaction Formula 1. The substituent may be bonded by a method known in the art, and the kind and position of the substituent or the number of substituents may be changed according to the technology known in the art.

[Reaction Formula 1]

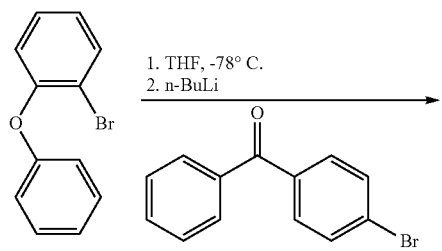

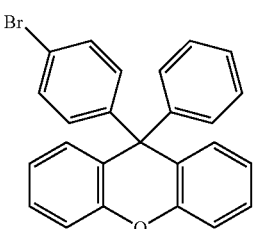

In Reaction Formula 1, the bonding position of Br may be adjusted by using (3-bromophenyl) (phenyl)methanone or (2-bromophenyl) (phenyl)methanone instead of 2A, and the compound of Chemical Formula 1 may be prepared by substituting Br with a substituent corresponding to the definition of Ar in Chemical Formula 1.

The HOMO energy level of the compound represented by Chemical Formula 1 according to an exemplary embodiment of the present specification is 6.0 eV or more.

The LUMO energy level of the compound represented by Chemical Formula 1 according to an exemplary embodiment of the present specification is 2.9 eV or more.

Further, the present specification provides an organic light emitting device including the above-described compound.

An exemplary embodiment of the present application provides an organic light emitting device including: a first electrode; a second electrode disposed to face the first electrode; and an organic material layer having one or more layers disposed between the first electrode and the second electrode, in which one or more layers of the organic material layer include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic material layer of the organic light emitting device of the present application may also be composed of a single-layered structure, but may be composed of a multi-layered structure in which two or more organic material layers are stacked. For example, as a representative example of the organic light emitting device of the present invention, an organic light emitting device may have a structure including a hole injection layer, a hole transporting layer, a light emitting layer, an electron transporting layer, an electron injection layer, and the like as organic material layers.

However, the structure of the organic light emitting device is not limited thereto, and may include a fewer number of organic material layers.

In an exemplary embodiment of the present application, the organic material layer includes a light emitting layer, and the light emitting layer includes the compound.

In an exemplary embodiment of the present application, the organic material layer includes a hole injection layer or a hole transporting layer, and the hole injection layer or the hole transporting layer includes the compound.

In an exemplary embodiment of the present application, the organic material layer includes an electron transporting layer or an electron injection layer, and the electron transporting layer or the electron injection layer includes the compound.

In an exemplary embodiment of the present application, the organic material layer includes an electron transporting layer, an electron injection layer, or an electron injection and transporting layer, and the electron transporting layer, the electron injection layer, or the electron injection or transporting layer includes the compound.

In an exemplary embodiment of the present application, the electron injection layer, the electron transporting layer, or the electron injection and transporting layer may include an additional compound.

In an exemplary embodiment of the present application, the electron injection layer, the electron transporting layer, or the electron injection and transporting layer may further include an N-type dopant.

In an exemplary embodiment of the present application, the electron injection layer, the electron transporting layer, or the electron injection and transporting layer may further include a metal complex.

In an exemplary embodiment of the present application, the electron injection layer, the electron transporting layer, or the electron injection and transporting layer may further include an alkali metal complex.

In an exemplary embodiment of the present application, the electron injection layer, the electron transporting layer, or the electron injection and transporting layer may further include lithium quinolate.

In an exemplary embodiment of the present application, the electron injection layer, the electron transporting layer, or the electron injection and transporting layer may include the compound of the present application and lithium quinolate at a weight ratio of 1:9 to 9:1.

In an exemplary embodiment of the present application, the electron injection layer, the electron transporting layer, or the electron injection and transporting layer may include the compound of the present application and lithium quinolate at a weight ratio of 4:6 to 6:4.

In an exemplary embodiment of the present application, the electron injection layer, the electron transporting layer, or the electron injection and transporting layer may include the compound of the present application and lithium quinolate at a weight ratio of 1:1.

In an exemplary embodiment of the present application, the organic material layer includes an electron blocking layer or a hole blocking layer, and the electron blocking layer or the hole blocking layer includes the compound.

In an exemplary embodiment of the present application, the organic material layer including the compound of Chemical Formula 1 has a thickness of 1 Å to 1,000 Å, and more preferably 1 Å to 500 Å.

In an exemplary embodiment of the present application, the organic light emitting device includes: a first electrode; a second electrode disposed to face the first electrode; a light emitting layer disposed between the first electrode and the second electrode; and an organic material layer having two or more layers disposed between the light emitting layer and the first electrode, or between the light emitting layer and the second electrode, in which at least one of the organic material layer having two or more layers includes the compound.

In an exemplary embodiment of the present application, as the organic material layer having two or more layers, two or more may be selected from the group consisting of an electron transporting layer, an electron injection layer, a layer which transports and injects electrons simultaneously, and a hole blocking layer.

In an exemplary embodiment of the present application, the organic material layer includes two or more electron transporting layers, and at least one of the two or more electron transporting layers includes the compound. Specifically, in an exemplary embodiment of the present specification, the compound may also be included in one layer of the two or more electron transporting layers, and may be included in each layer of the two or more electron transporting layers.

In addition, in an exemplary embodiment of the present application, when the compound is included in each of the two or more electron transporting layers, the other materials except for the compound may be the same as or different from each other.

In an exemplary embodiment of the present application, the organic material layer further includes a hole injection layer or a hole transporting layer, which includes a compound including an arylamino group, a carbazolyl group, or a benzocarbazolyl group, in addition to the organic material layer including the compound.

In another exemplary embodiment, the organic light emitting device may be an organic light emitting device having a normal type structure in which a positive electrode, an organic material layer having one or more layers, and a negative electrode are sequentially stacked on a substrate.

In still another exemplary embodiment, the organic light emitting device may be an organic light emitting device having an inverted type structure in which a negative electrode, an organic material layer having one or more layers, and a positive electrode are sequentially stacked on a substrate.

Figure 2:
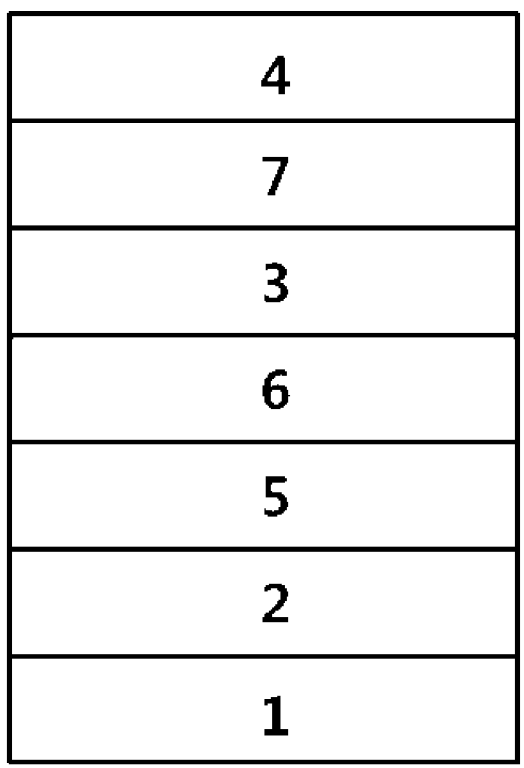
FIG. 2 illustrates an example of an organic light emitting device in which a substrate 1, a positive electrode 2, a hole injection layer 5, a hole transporting layer 6, a light emitting layer 3, an electron transporting layer 7, and a negative electrode 4 are sequentially stacked.

For example, the structure of the organic light emitting device according to an exemplary embodiment of the present application is exemplified in FIGS. 1 and 2.

FIG. 1 exemplifies a structure of an organic light emitting device in which a substrate 1, a positive electrode 2, a light emitting layer 3, and a negative electrode 4 are sequentially stacked. In the structure described above, the compound may be included in the light emitting layer 3.

FIG. 2 exemplifies a structure of an organic light emitting device in which a substrate 1, a positive electrode 2, a hole injection layer 5, a hole transporting layer 6, a light emitting layer 3, an electron transporting layer 7, and a negative electrode 4 are sequentially stacked. In the structure described above, the compound may be included in one or more layers of the hole injection layer 5, the hole transporting layer 6, the light emitting layer 3, and the electron transporting layer 7.

In the structure described above, the compound may be included in one or more layers of the hole injection layer, the hole transporting layer, the light emitting layer, and the electron transporting layer.

The organic light emitting device of the present application may be manufactured by the materials and methods known in the art, except that one or more layers of the organic material layer include the compound of the present application, that is, the compound.

When the organic light emitting device includes a plurality of organic material layers, the organic material layers may be formed of the same material or different materials.

The organic light emitting device of the present application may be manufactured by the materials and methods known in the art, except that one or more layers of the organic material layer include the compound, that is, the compound represented by Chemical Formula 1.

For example, the organic light emitting device of the present application may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present application, the first electrode is a positive electrode, and the second electrode is a negative electrode.

In another exemplary embodiment, the first electrode is a negative electrode, and the second electrode is a positive electrode.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is a material which may emit light in a visible light region by accepting and combining holes and electrons from a hole transporting layer and an electron transporting layer, respectively, and preferably a material having high quantum efficiency for fluorescence or phosphorescence. Specific examples thereof include: an 8-hydroxy-quinoline aluminum complex ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

The electron transporting layer is a layer which receives electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: an Al complex of 8-hydroxyquinoline; a complex including $Alq_3$; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a negative electrode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and a derivative thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

MODE FOR INVENTION

The preparation of the compound represented by Chemical Formula 1 and the organic light emitting device including the same will be specifically described in the following Examples. However, the following Examples are provided for exemplifying the present specification, and the scope of the present specification is not limited thereby.

Preparation Example 1. Synthesis of Chemical Formula E1

[Chemical Formula E1]

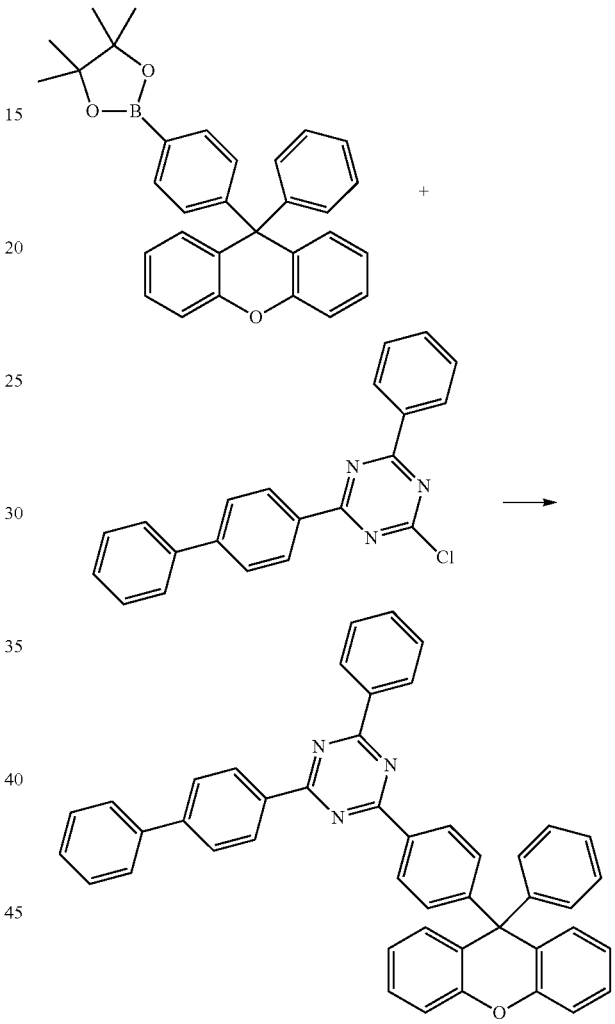

After the compounds 4,4,5,5-tetramethyl-2-(4-(9-phenyl-9H-xanthene-9-yl)phenyl)-1,3,2-dioxaborolane (10.0 g, 21.7 mmol) and 2-([1,1'-biphenyl]-4-yl)-4-chloro-6-phenyl-1,3,4-triazine (7.5 g, 21.7 mmol) were completely dissolved in tetrahydrofuran (100 ml), potassium carbonate (9.0 g, 65.4 mmol) was dissolved in 50 ml of water, the resulting solution was added thereto, tetrakistriphenyl-phosphinopaladium (753 mg, 0.65 mmol) was put thereinto, and then the resulting mixture was heated and stirred for 8 hours. The temperature was lowered to room temperature, the reaction was terminated, and then the potassium carbonate solution was removed to filter the white solid. The filtered white solid was washed each twice with tetrahydrofuran and ethyl acetate to prepare the compound of Chemical Formula E1 (12.5 g, yield 90%).

$MS[M+H]^+=642$

Figure 3:
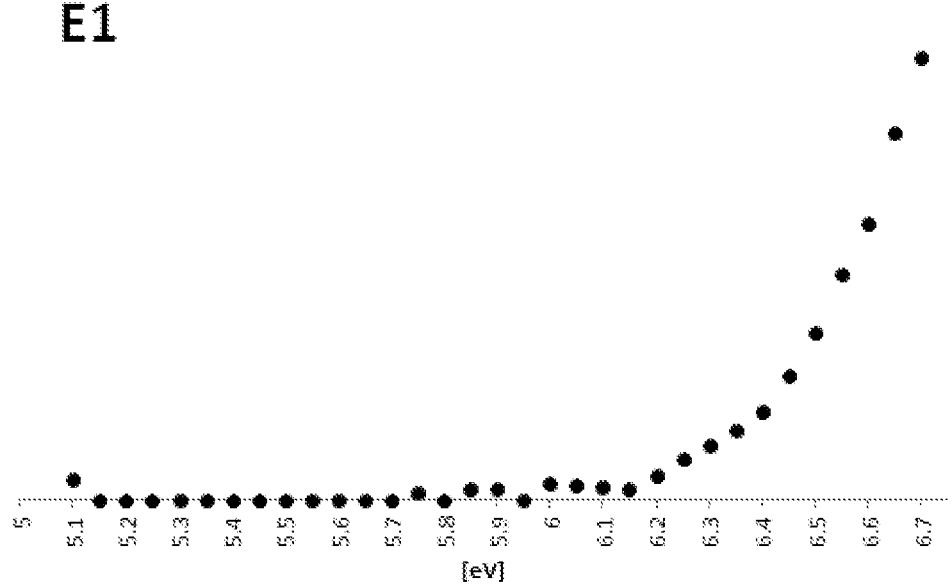
FIG. 3 illustrates a HOMO energy level of Compound E1 according to an exemplary embodiment of the present specification, which is measured by using a photoelectron spectrometer.

A HOMO energy level of the compound of Chemical Formula E1, which was measured by using a photoelectron spectrometer, is illustrated in FIG. 3.

Figure 6:
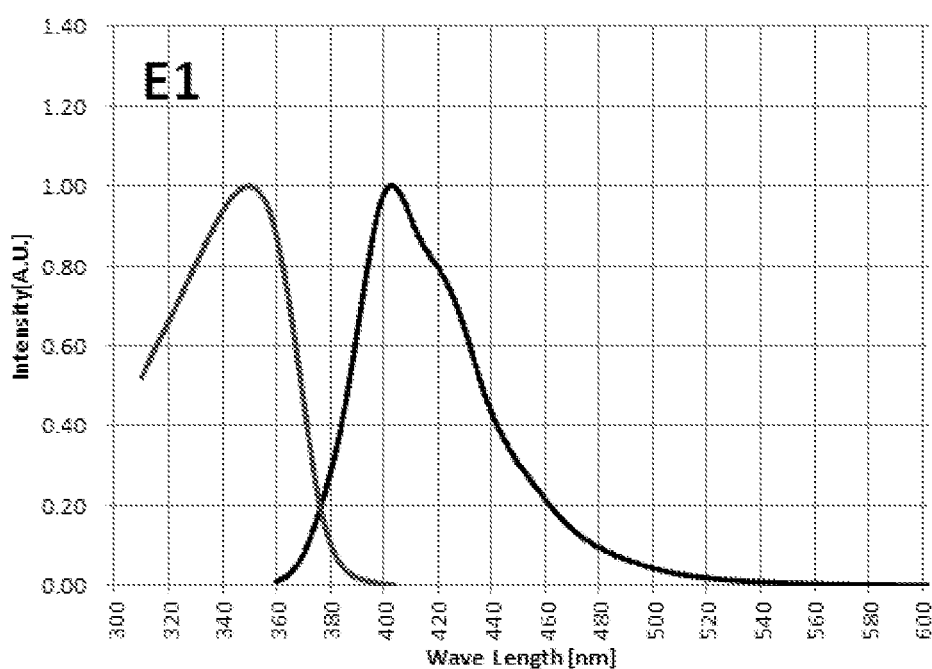
FIG. 6 is absorption and emission spectra of Compound E1 according to an exemplary embodiment of the present specification, which are measured via photoluminescence (PL).

The absorption and emission spectra of the compound of Chemical Formula E1, which were measured by using photoluminescence, are illustrated in FIG. 6.

Preparation Example 2. Synthesis of Chemical Formula E2

[Chemical Formula E2]

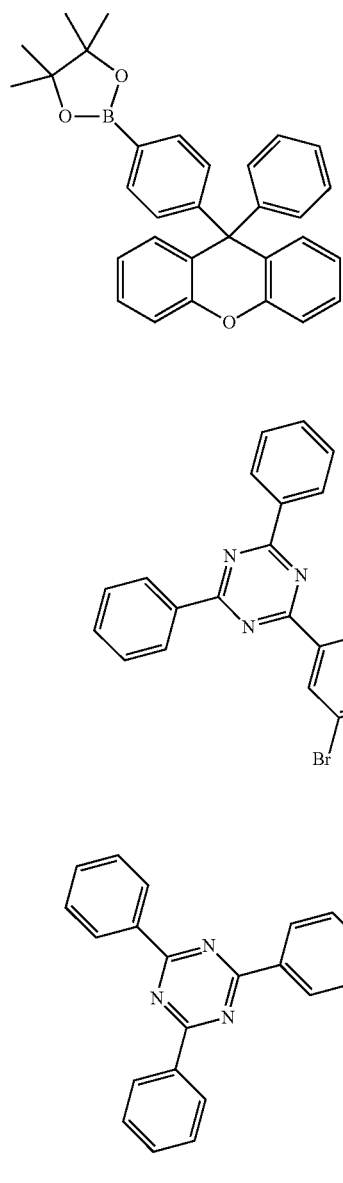

The compound represented by Chemical Formula E2 was prepared in the same manner as in Preparation Example 1, except that each starting material was used as in the reaction formula.

MS[M+H]$^+$=642

Preparation Example 3. Synthesis of Chemical Formula E3

[Chemical Formula E3]

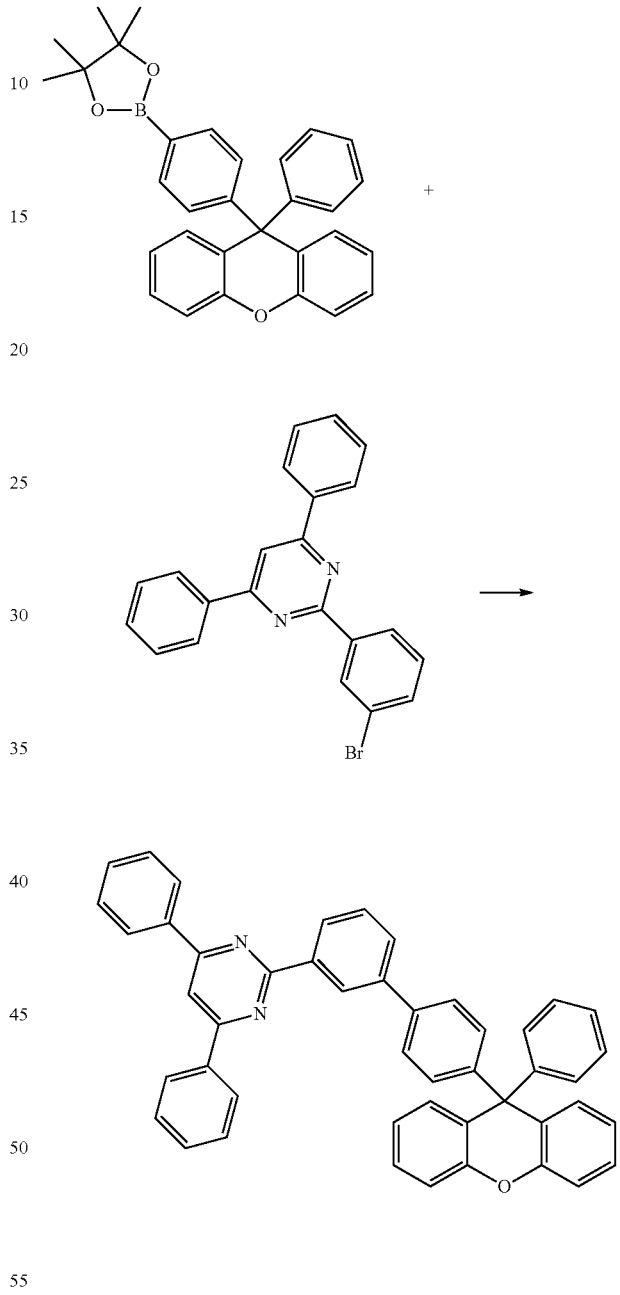

The compound represented by Chemical Formula E3 was prepared in the same manner as in Preparation Example 1, except that each starting material was used as in the reaction formula.

MS[M+H]$^+$=641

Figure 4:
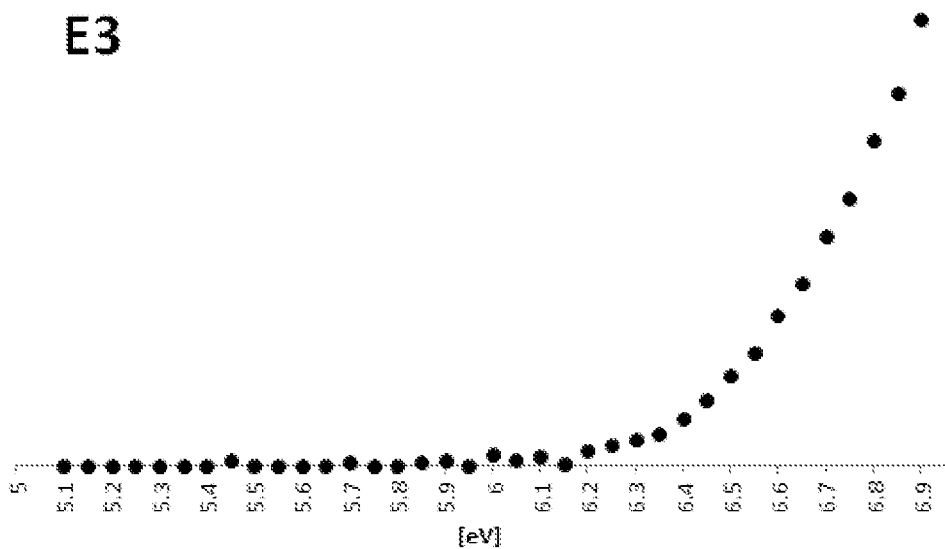
FIG. 4 illustrates a HOMO energy level of Compound E3 according to an exemplary embodiment of the present specification, which is measured by using a photoelectron spectrometer.

A HOMO energy level of the compound of Chemical Formula E3, which was measured by using a photoelectron spectrometer, is illustrated in FIG. 4.

Figure 7:
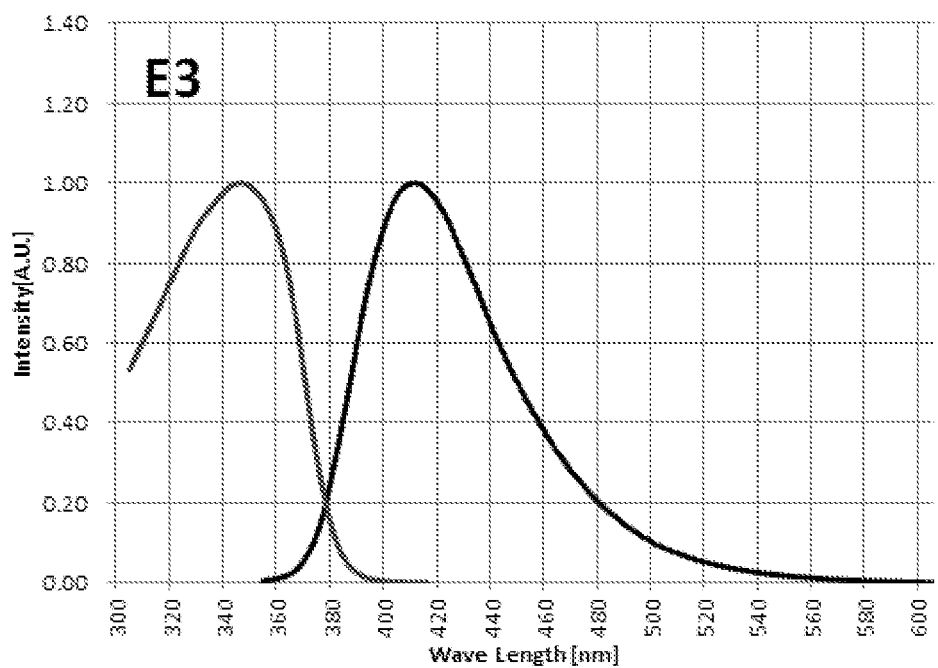
FIG. 7 is absorption and emission spectra of Compound E3 according to an exemplary embodiment of the present specification, which are measured via photoluminescence (PL).

The absorption and emission spectra of the compound of Chemical Formula E3, which were measured by using photoluminescence, are illustrated in FIG. 7.

Preparation Example 4. Synthesis of Chemical Formula E4

[Chemical Formula E4]

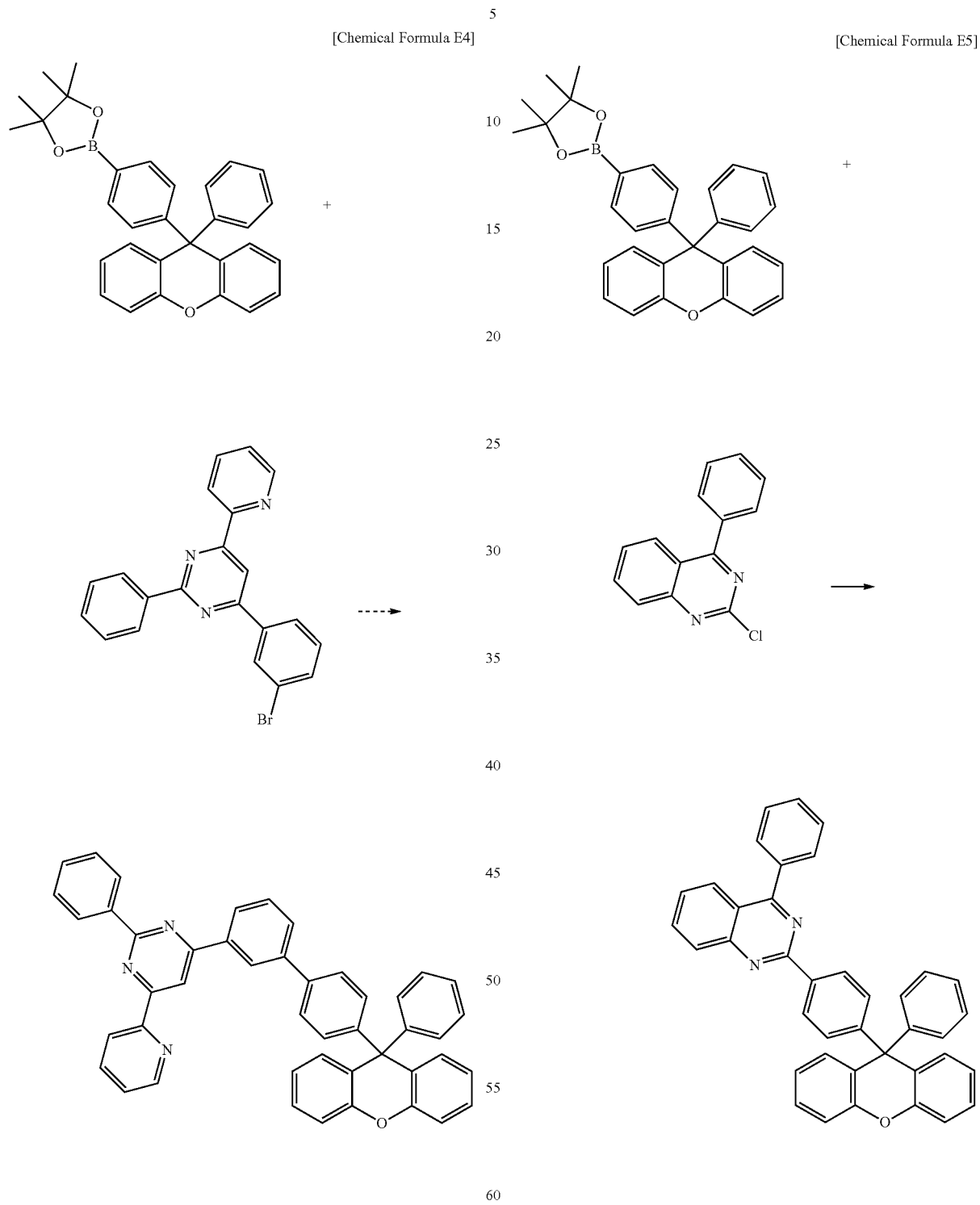

The compound represented by Chemical Formula E4 was prepared in the same manner as in Preparation Example 1, except that each starting material was used as in the reaction formula.

MS[M+H]$^+$=642

Preparation Example 5. Synthesis of Chemical Formula E5

[Chemical Formula E5]

The compound represented by Chemical Formula E5 was prepared in the same manner as in Preparation Example 1, except that each starting material was used as in the reaction formula.

MS[M+H]$^+$=539

Preparation Example 6. Synthesis of Chemical Formula E6

[Chemical Formula E6]

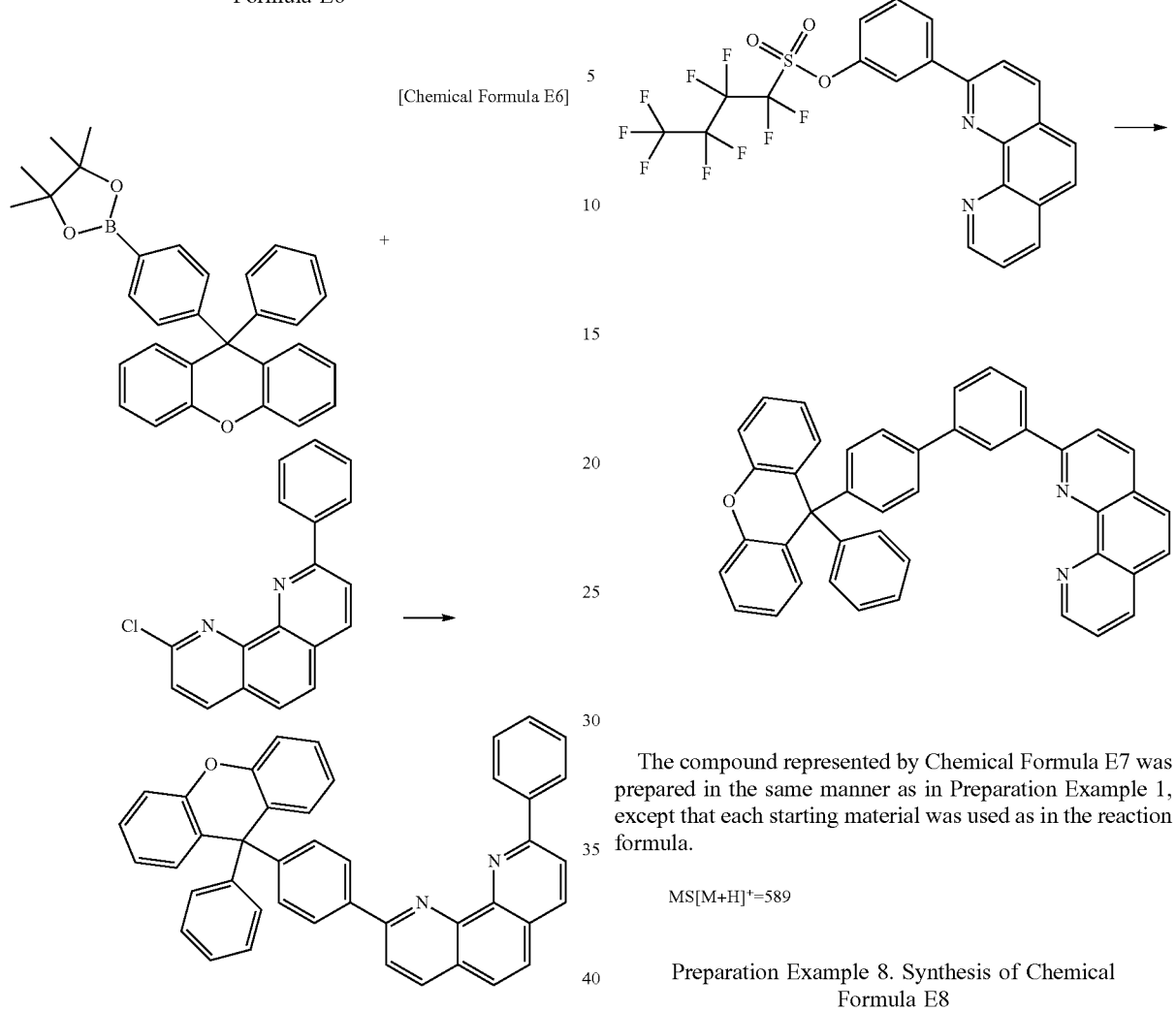

The compound represented by Chemical Formula E6 was prepared in the same manner as in Preparation Example 1, except that each starting material was used as in the reaction formula.

MS[M+H]⁺=589

Preparation Example 7. Synthesis of Chemical Formula E7

[Chemical Formula E7]

The compound represented by Chemical Formula E7 was prepared in the same manner as in Preparation Example 1, except that each starting material was used as in the reaction formula.

MS[M+H]⁺=589

Preparation Example 8. Synthesis of Chemical Formula E8

[Chemical Formula E8]

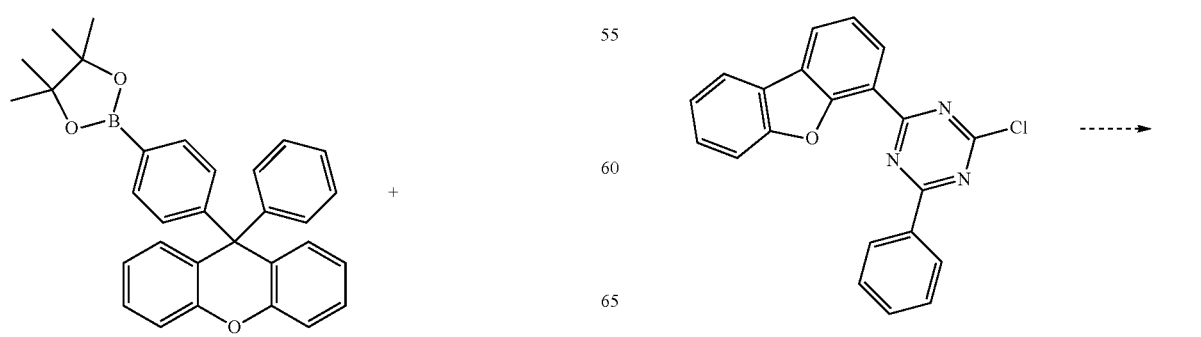

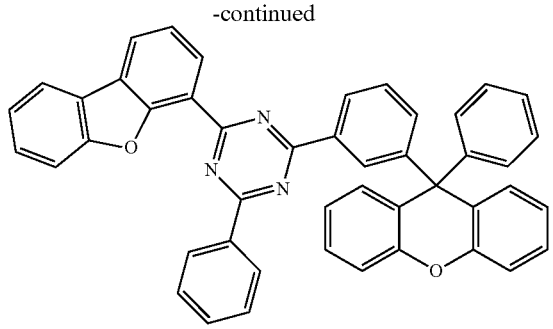

The compound represented by Chemical Formula E8 was prepared in the same manner as in Preparation Example 1, except that each starting material was used as in the reaction formula.

MS[M+H]⁺=656

Preparation Example 9. Synthesis of Chemical Formula E9

[Chemical Formula E9]

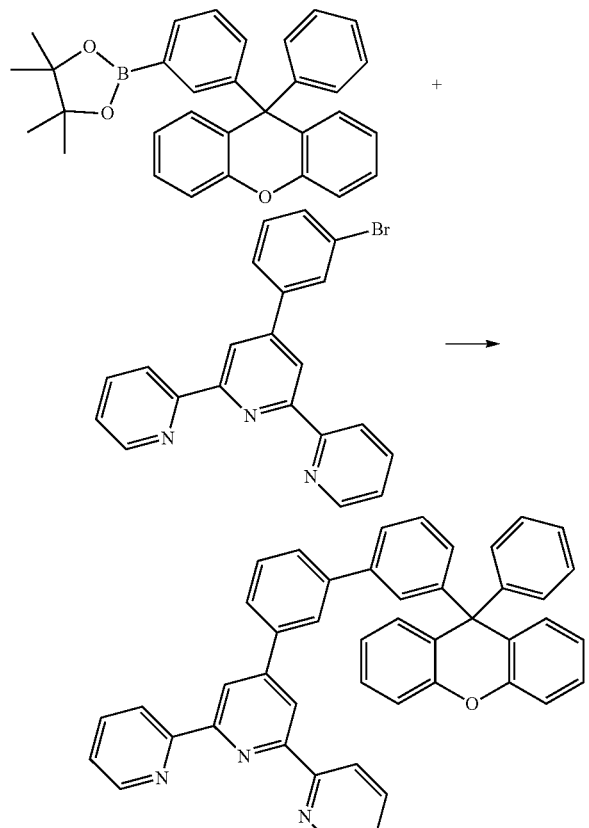

The compound represented by Chemical Formula E9 was prepared in the same manner as in Preparation Example 1, except that each starting material was used as in the reaction formula.

MS[M+H]⁺=642

Preparation Example 10. Synthesis of Chemical Formula E10

[Chemical Formula E10]

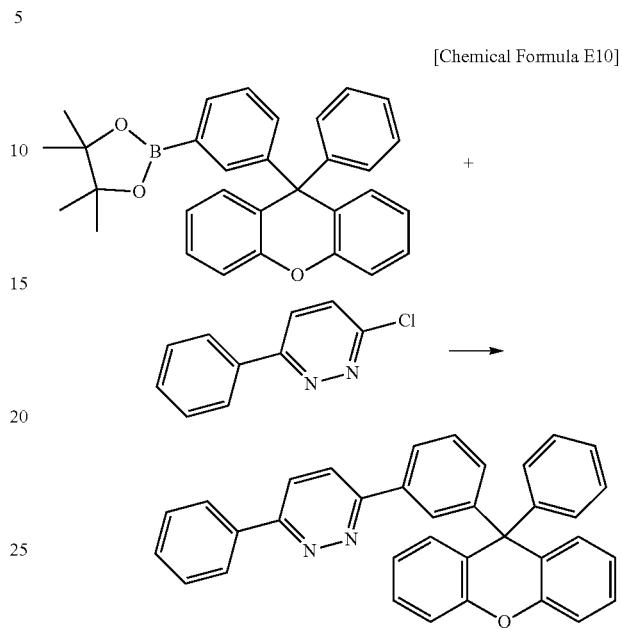

The compound represented by Chemical Formula E10 was prepared in the same manner as in Preparation Example 1, except that each starting material was used as in the reaction formula.

MS[M+H]⁺=489

Preparation Example 11. Synthesis of Chemical Formula E11

[Chemical Formula E11]

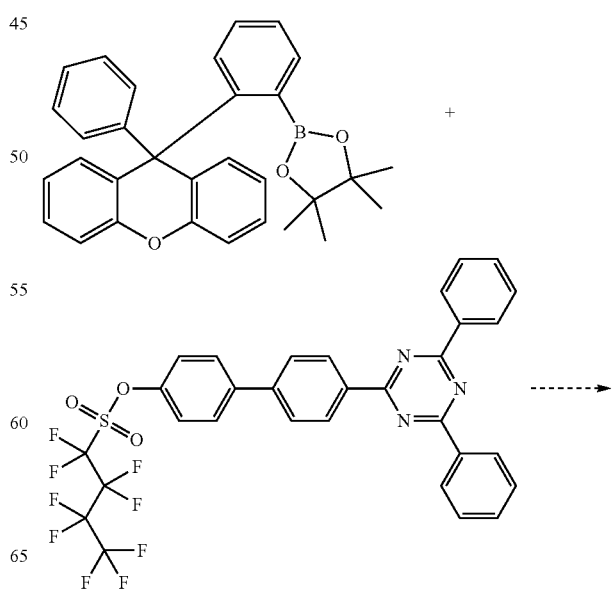

-continued

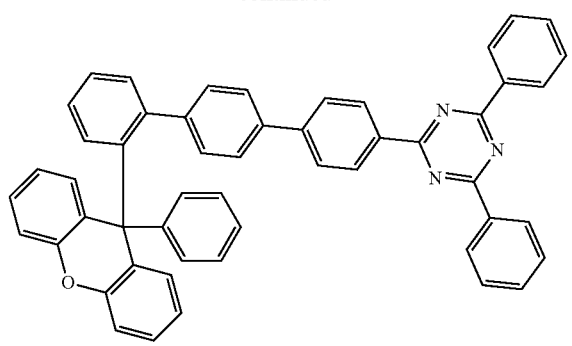

The compound represented by Chemical Formula E11 was prepared in the same manner as in Preparation Example 1, except that each starting material was used as in the reaction formula.

MS[M+H]⁺=718

Preparation Example 12. Synthesis of Chemical Formula E12

[Chemical Formula E12]

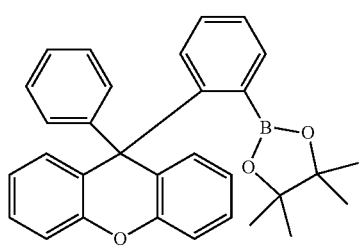

+

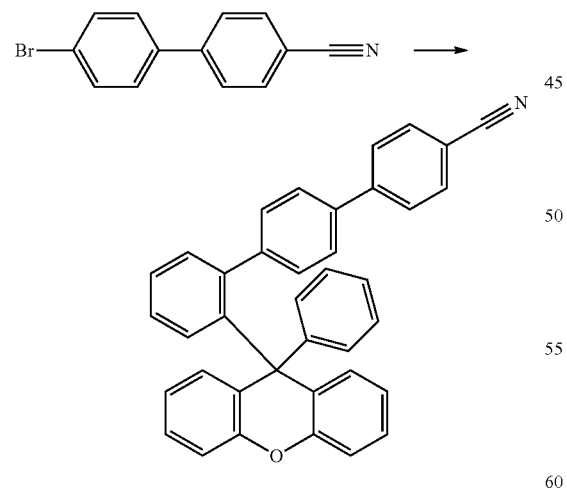

The compound represented by Chemical Formula E12 was prepared in the same manner as in Preparation Example 1, except that each starting material was used as in the reaction formula.

MS[M+H]⁺=512

Preparation Example 13. Synthesis of Chemical Formula E13

[Chemical Formula E13]

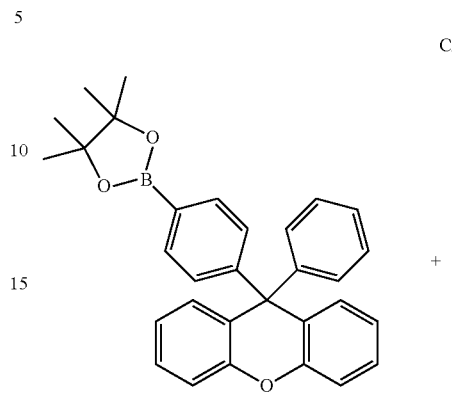

+

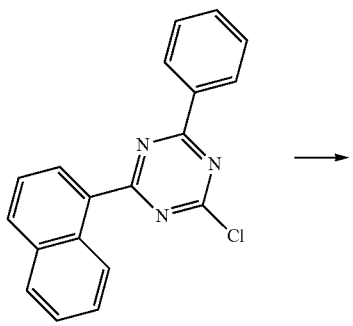

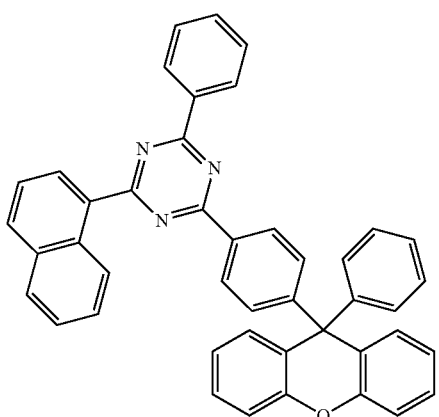

The compound represented by Chemical Formula E13 was prepared in the same manner as in Preparation Example 1, except that each starting material was used as in the reaction formula.

MS[M+H]⁺=616

Preparation Example 14. Synthesis of Chemical Formula E14

[Chemical Formula E14]

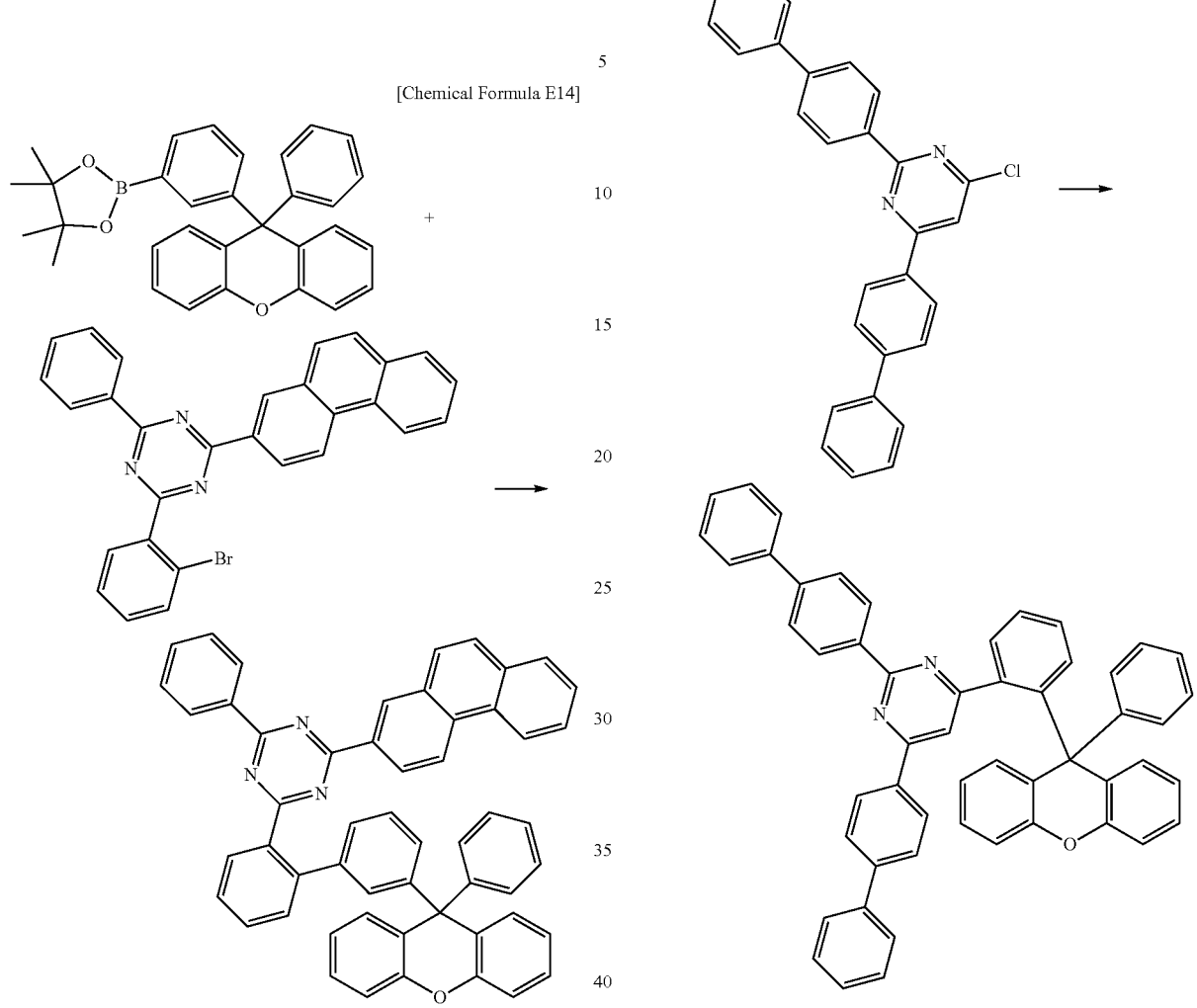

The compound represented by Chemical Formula E14 was prepared in the same manner as in Preparation Example 1, except that each starting material was used as in the reaction formula.

MS[M+H]$^+$=742

Preparation Example 15. Synthesis of Chemical Formula E15

[Chemical Formula E15]

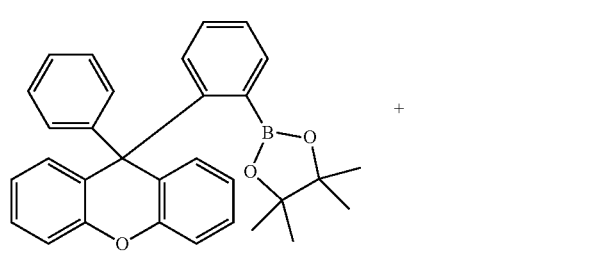

The compound represented by Chemical Formula E15 was prepared in the same manner as in Preparation Example 1, except that each starting material was used as in the reaction formula.

MS[M+H]$^+$=717

Experimental Example 1-1

A glass substrate thinly coated with indium tin oxide (ITO) to have a thickness of 1,000 Å was put into distilled water in which a detergent was dissolved, and ultrasonically washed. At this time, a product manufactured by Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

The following Compound [HI-A] was thermally vacuum deposited to have a thickness of 600 Å on the transparent ITO electrode, which was thus prepared, thereby forming a hole injection layer. Hexanitrile hexaazatriphenylene (HAT) of the following chemical formula (50 Å) and the following compound [HT-A] (600 Å) were sequentially vacuum deposited on the hole injection layer, thereby forming a hole transporting layer.

Next, the following Compounds [BH] and [BD] were vacuum deposited at a weight ratio of 25:1 to have a film thickness of 200 Å on the hole transporting layer, thereby forming a light emitting layer.

The compound of [Chemical Formula E1] and the following compound [LiQ] (lithium quinolate) were vacuum deposited at a weight ratio of 1:1 on the light emitting layer, thereby forming an electron injection and transporting layer having a thickness of 350 Å. Lithium fluoride (LiF) and aluminum were sequentially deposited to have a thickness of 10 Å and 1,000 Å, respectively, on the electron injection and transporting layer, thereby forming a negative electrode.

In the aforementioned procedure, the deposition rate of the organic material was maintained at 0.4 to 0.9 Å/sec, the deposition rates of lithium fluoride and aluminum of the negative electrode were maintained at 0.3 Å/sec and at 2 Å/sec, respectively, and the degree of vacuum during the deposition was maintained at $1\times10^{-7}$ to $5\times10^{-8}$ torr, thereby manufacturing an organic light emitting device.

[HAT]

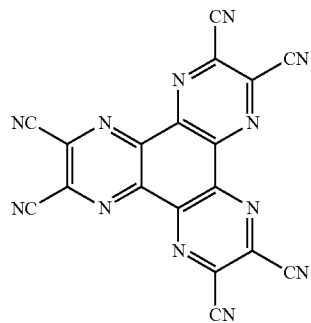

[HI-A]

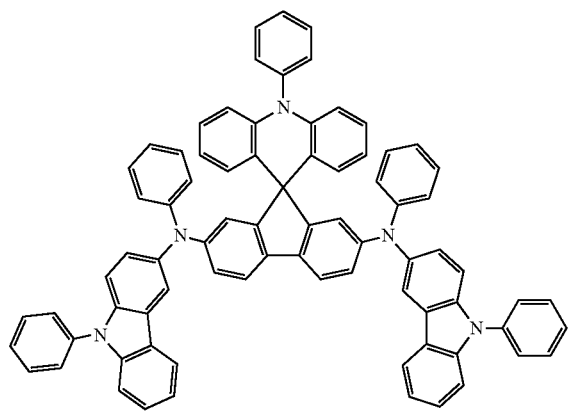

[HT-A]

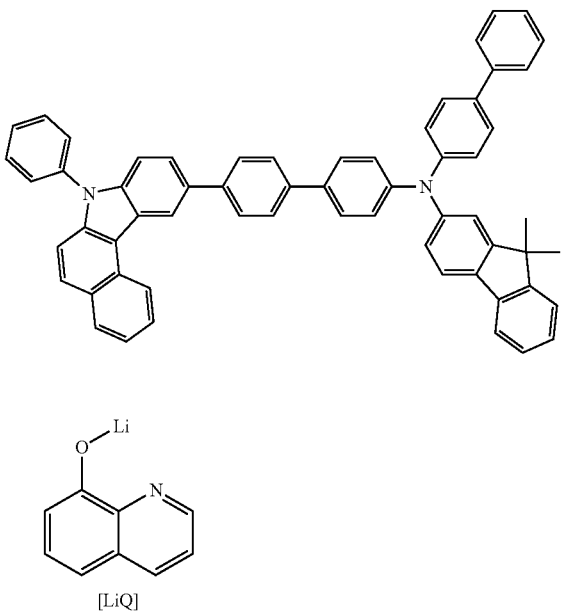

[LiQ]

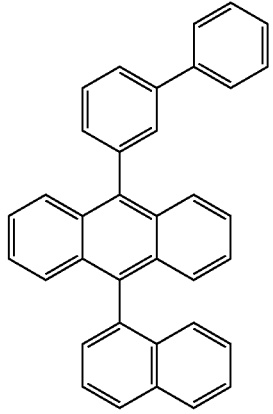

[BH]

[BD]

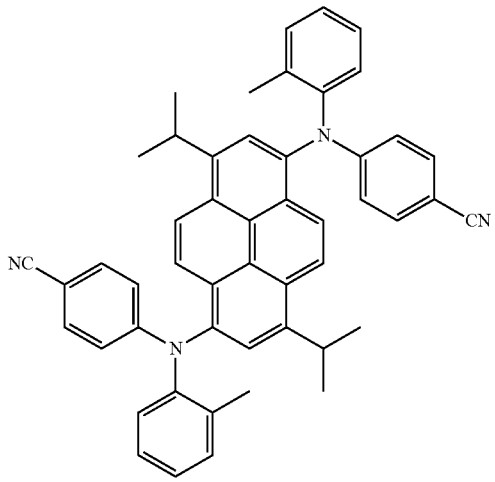

[ET-1-A]
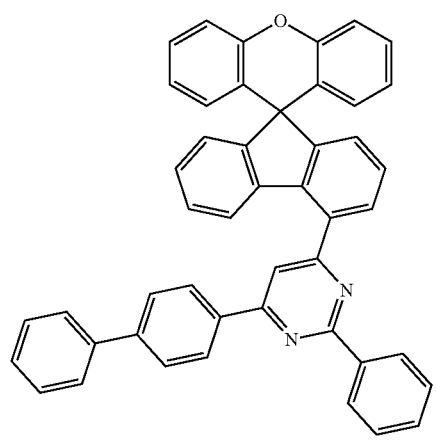
[ET-1-B]
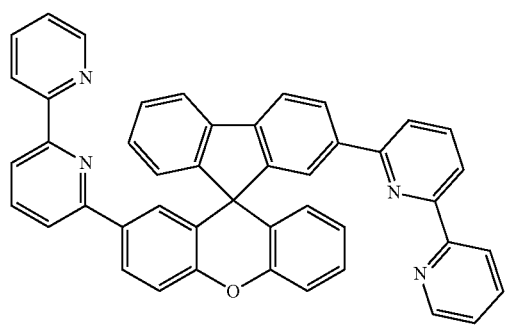
[ET-1-C]
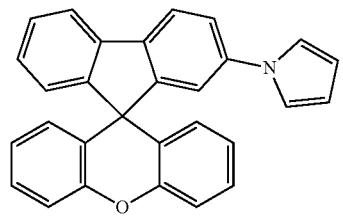
[ET-1-D]
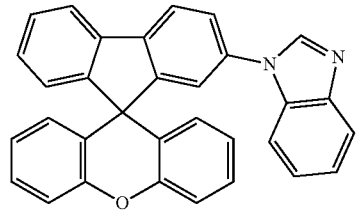
[ET-1-E]
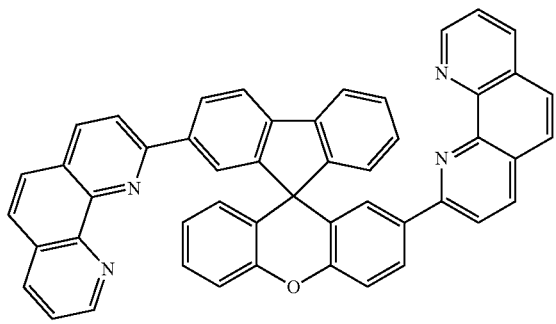
[ET-1-F]
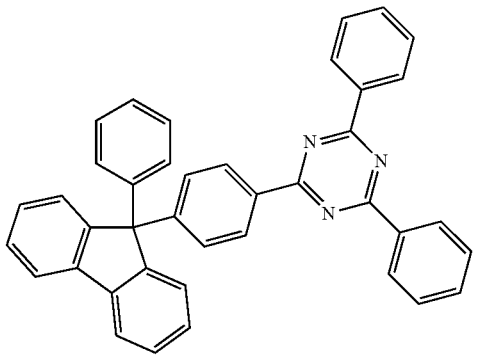
[ET-1-G]
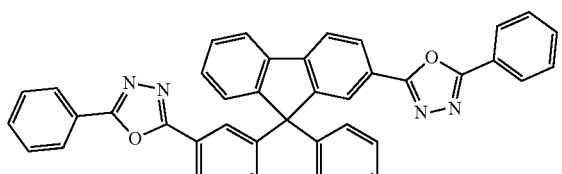
[ET-1-H]
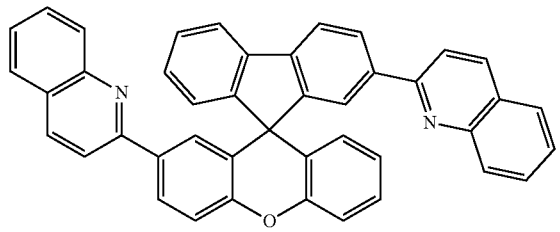
[ET-1-I]
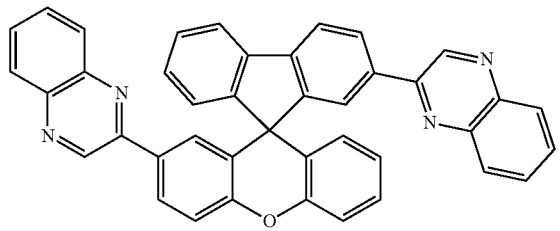
[ET-1-J]
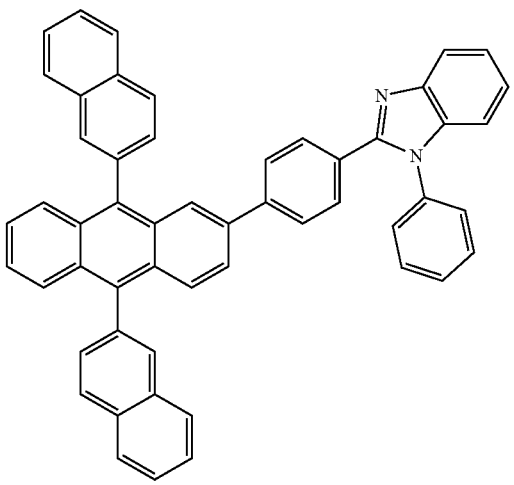

-continued

[ET-1-K]

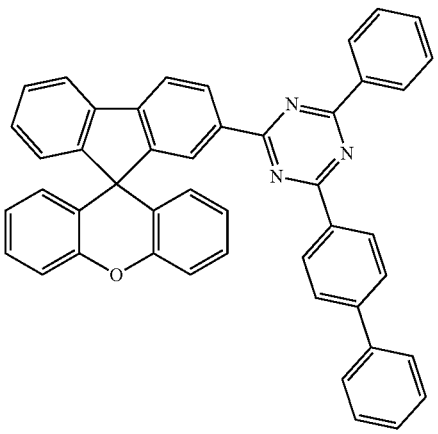

[ET-1-L]

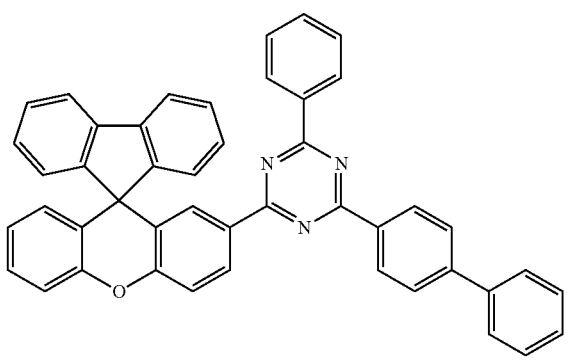

Experimental Example 1-2

An organic light emitting device was manufactured in the same manner as in Experimental Example 1-1, except that the compound of Chemical Formula E2 was used instead of the compound of Chemical Formula E1 in Experimental Example 1-1.

Experimental Example 1-3

An organic light emitting device was manufactured in the same manner as in Experimental Example 1-1, except that the compound of Chemical Formula E3 was used instead of the compound of Chemical Formula E1 in Experimental Example 1-1.

Experimental Example 1-4

An organic light emitting device was manufactured in the same manner as in Experimental Example 1-1, except that the compound of Chemical Formula E4 was used instead of the compound of Chemical Formula E1 in Experimental Example 1-1.

Experimental Example 1-5

An organic light emitting device was manufactured in the same manner as in Experimental Example 1-1, except that the compound of Chemical Formula E5 was used instead of the compound of Chemical Formula E1 in Experimental Example 1-1.

Experimental Example 1-6

An organic light emitting device was manufactured in the same manner as in Experimental Example 1-1, except that the compound of Chemical Formula E6 was used instead of the compound of Chemical Formula E1 in Experimental Example 1-1.

Experimental Example 1-7

An organic light emitting device was manufactured in the same manner as in Experimental Example 1-1, except that the compound of Chemical Formula E7 was used instead of the compound of Chemical Formula E1 in Experimental Example 1-1.

Experimental Example 1-8

An organic light emitting device was manufactured in the same manner as in Experimental Example 1-1, except that the compound of Chemical Formula E8 was used instead of the compound of Chemical Formula E1 in Experimental Example 1-1.

Experimental Example 1-9

An organic light emitting device was manufactured in the same manner as in Experimental Example 1-1, except that the compound of Chemical Formula E9 was used instead of the compound of Chemical Formula E1 in Experimental Example 1-1.

Experimental Example 1-10

An organic light emitting device was manufactured in the same manner as in Experimental Example 1-1, except that the compound of Chemical Formula E10 was used instead of the compound of Chemical Formula E1 in Experimental Example 1-1.

Experimental Example 1-11

An organic light emitting device was manufactured in the same manner as in Experimental Example 1-1, except that the compound of Chemical Formula E11 was used instead of the compound of Chemical Formula E1 in Experimental Example Experimental Example 1-12

An organic light emitting device was manufactured in the same manner as in Experimental Example 1-1, except that the compound of Chemical Formula E12 was used instead of the compound of Chemical Formula E1 in Experimental Example 1-1.

Experimental Example 1-13

An organic light emitting device was manufactured in the same manner as in Experimental Example 1-1, except that the compound of Chemical Formula E13 was used instead of the compound of Chemical Formula E1 in Experimental Example 1-1.

Experimental Example 1-14

An organic light emitting device was manufactured in the same manner as in Experimental Example 1-1, except that the compound of Chemical Formula E14 was used instead of the compound of Chemical Formula E1 in Experimental Example 1-1.

Experimental Example 1-15

An organic light emitting device was manufactured in the same manner as in Experimental Example 1-1, except that the compound of Chemical Formula E15 was used instead of the compound of Chemical Formula E1 in Experimental Example Comparative Example 1-1

An organic light emitting device was manufactured in the same manner as in Experimental Example 1-1, except that the compound of Chemical Formula ET-1-A was used instead of the compound of Chemical Formula E1 in Experimental Example 1-1.

Comparative Example 1-2

An organic light emitting device was manufactured in the same manner as in Experimental Example 1-1, except that the compound of Chemical Formula ET-1-B was used instead of the compound of Chemical Formula E1 in Experimental Example 1-1.

Comparative Example 1-3

An organic light emitting device was manufactured in the same manner as in Experimental Example 1-1, except that the compound of Chemical Formula ET-1-C was used instead of the compound of Chemical Formula E1 in Experimental Example 1-1.

Comparative Example 1-4

An organic light emitting device was manufactured in the same manner as in Experimental Example 1-1, except that the compound of Chemical Formula ET-1-D was used instead of the compound of Chemical Formula E1 in Experimental Example 1-1.

Comparative Example 1-5

An organic light emitting device was manufactured in the same manner as in Experimental Example 1-1, except that the compound of Chemical Formula ET-1-E was used instead of the compound of Chemical Formula E1 in Experimental Example 1-1.

Comparative Example 1-6

An organic light emitting device was manufactured in the same manner as in Experimental Example 1-1, except that the compound of Chemical Formula ET-1-F was used instead of the compound of Chemical Formula E1 in Experimental Example 1-1.

Comparative Example 1-7

An organic light emitting device was manufactured in the same manner as in Experimental Example 1-1, except that the compound of Chemical Formula ET-1-G was used instead of the compound of Chemical Formula E1 in Experimental Example 1-1.

Comparative Example 1-8

An organic light emitting device was manufactured in the same manner as in Experimental Example 1-1, except that the compound of Chemical Formula ET-1-H was used instead of the compound of Chemical Formula E1 in Experimental Example 1-1.

Comparative Example 1-9

An organic light emitting device was manufactured in the same manner as in Experimental Example 1-1, except that the compound of Chemical Formula ET-1-I was used instead of the compound of Chemical Formula E1 in Experimental Example 1-1.

Comparative Example 1-10

An organic light emitting device was manufactured in the same manner as in Experimental Example 1-1, except that the compound of Chemical Formula ET-1-J was used instead of the compound of Chemical Formula E1 in Experimental Example 1-1.

Figure 5:
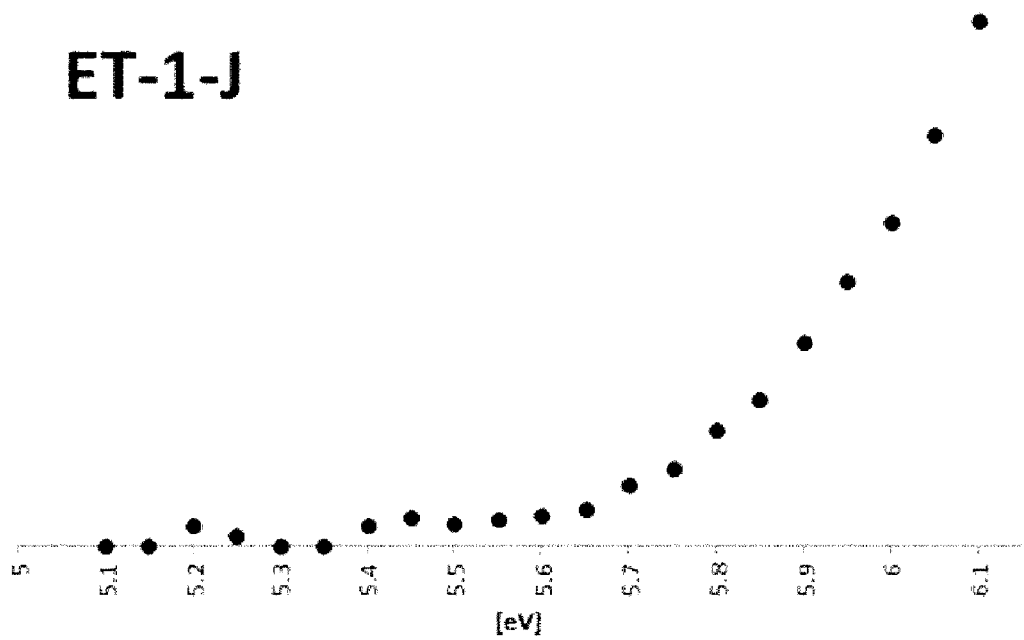
FIG. 5 illustrates a HOMO energy level of Compound [ET-1-J], which is measured by using a photoelectron spectrometer.
Figure 8:
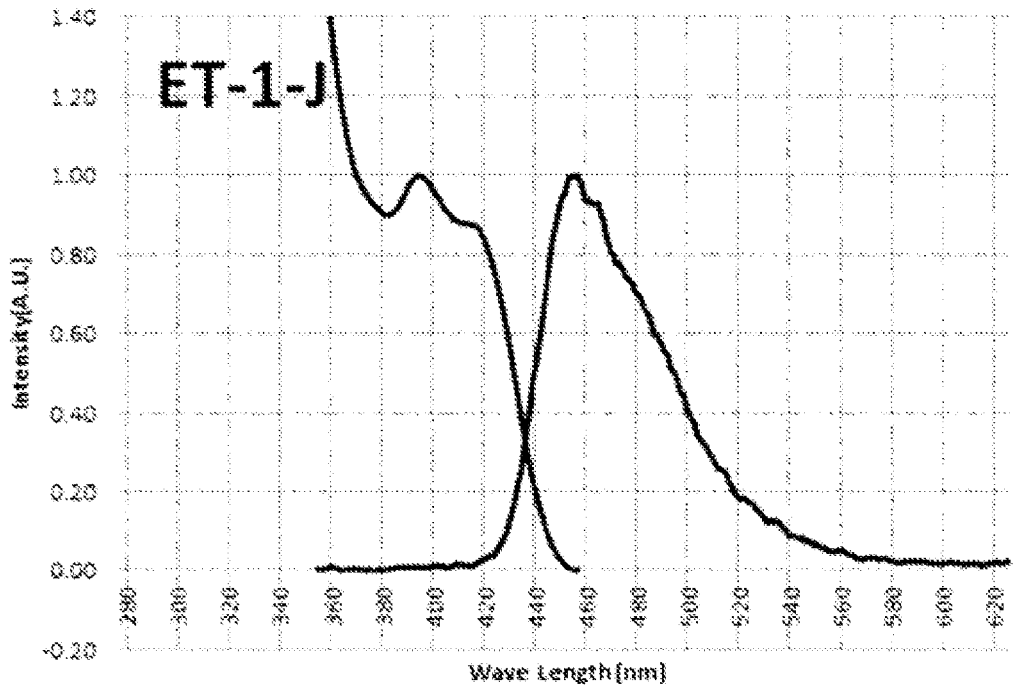
FIG. 8 is absorption and emission spectra of Compound [ET-1-J], which are measured via photoluminescence (PL).

Further, the HOMO energy level of Compound [ET-1-J], which was measured by using a photoelectron spectrometer, is illustrated in FIG. 5, and the absorption and emission spectra of Compound [ET-1-J], which were measured by using photoluminescence, are illustrated in FIG. 8.

Comparative Example 1-11

An organic light emitting device was manufactured in the same manner as in Experimental Example 1-1, except that the compound of Chemical Formula ET-1-K was used instead of the compound of Chemical Formula E1 in Experimental Example 1-1.

Comparative Example 1-12

An organic light emitting device was manufactured in the same manner as in Experimental Example 1-1, except that the compound of Chemical Formula ET-1-L was used instead of the compound of Chemical Formula E1 in Experimental Example 1-1.

For the organic light emitting devices manufactured by the above-described methods in Experimental Examples 1-1 to 1-15 and Comparative Examples 1-1 to 1-12, the driving voltage and the light emitting efficiency were measured at a current density of 10 mA/cm$^2$, and a time ($T_{90}$) for reaching a 90% value compared to the initial luminance was measured at a current density of 20 mA/cm$^2$. The results are shown in the following Table 1.

TABLE 1

| | Chemical Formula | Voltage (V@10 mA/cm$^2$) | Efficiency (cd/A@10 mA/cm$^2$) | Color coordinate (x, y) | Service life (h) $T_{90}$ at 20 mA/cm$^2$ |
|---|---|---|---|---|---|
| Experimental Example 1-1 | E1 | 4.37 | 5.77 | (0.142, 0.097) | 110 |
| Experimental Example 1-2 | E2 | 4.25 | 5.80 | (0.142, 0.096) | 100 |
| Experimental Example 1-3 | E3 | 4.44 | 5.82 | (0.142, 0.096) | 98 |
| Experimental Example 1-4 | E4 | 4.30 | 5.75 | (0.142, 0.096) | 106 |

TABLE 1-continued

| | Chemical Formula | Voltage (V@10 mA/cm$^2$) | Efficiency (cd/A@10 mA/cm$^2$) | Color coordinate (x, y) | Service life (h) T$_{90}$ at 20 mA/cm$^2$ |
|---|---|---|---|---|---|
| Experimental Example 1-5 | E5 | 4.50 | 5.34 | (0.142, 0.096) | 97 |
| Experimental Example 1-6 | E6 | 4.41 | 5.40 | (0.142, 0.097) | 115 |
| Experimental Example 1-7 | E7 | 4.47 | 5.39 | (0.142, 0.096) | 112 |
| Experimental Example 1-8 | E8 | 4.39 | 5.71 | (0.142, 0.099) | 129 |
| Experimental Example 1-9 | E9 | 4.48 | 5.30 | (0.142, 0.096) | 96 |
| Experimental Example 1-10 | E10 | 4.39 | 5.68 | (0.142, 0.098) | 133 |
| Experimental Example 1-11 | E11 | 4.31 | 5.70 | (0.142, 0.096) | 136 |
| Experimental Example 1-12 | E12 | 4.47 | 5.48 | (0.142, 0.097) | 160 |
| Experimental Example 1-13 | E13 | 4.21 | 5.75 | (0.142, 0.096) | 120 |
| Experimental Example 1-14 | E14 | 4.33 | 5.80 | (0.142, 0.097) | 100 |
| Experimental Example 1-15 | E15 | 4.30 | 5.84 | (0.142, 0.097) | 101 |
| Comparative Example 1-1 | ET-1-A | 4.50 | 4.70 | (0.142, 0.098) | 90 |
| Comparative Example 1-2 | ET-1-B | 4.84 | 4.01 | (0.142, 0.102) | 77 |
| Comparative Example 1-3 | ET-1-C | 4.99 | 2.99 | (0.142, 0.096) | 81 |
| Comparative Example 1-4 | ET-1-D | 4.70 | 4.00 | (0.142, 0.096) | 57 |
| Comparative Example 1-5 | ET-1-E | 5.11 | 3.50 | (0.142, 0.096) | 65 |
| Comparative Example 1-6 | ET-1-F | 4.33 | 5.00 | (0.142, 0.096) | 30 |
| Comparative Example 1-7 | ET-1-G | 5.33 | 3.21 | (0.142, 0.096) | 40 |
| Comparative Example 1-8 | ET-1-H | 5.45 | 3.18 | (0.142, 0.096) | 45 |
| Comparative Example 1-9 | ET-1-I | 5.59 | 3.07 | (0.142, 0.096) | 52 |
| Comparative Example 1-10 | ET-1-J | 5.00 | 3.77 | (0.142, 0.096) | 80 |
| Comparative Example 1-11 | ET-1-K | 4.55 | 4.51 | (0.142, 0.097) | 88 |
| Comparative Example 1-12 | ET-1-L | 4.40 | 5.05 | (0.142, 0.097) | 27 |

From the results of Table 1, it can be confirmed that the heterocyclic compound represented by Chemical Formula 1 according to an exemplary embodiment of the present specification may be used for an organic material layer of an organic light emitting device which may simultaneously inject and transport electrons.

Specifically, when Experimental Examples 1-1 to 1-15 are compared with Comparative Examples 1-1 and 1-11, it can be confirmed that the compound having a diphenyl xanthene skeleton as in Chemical Formula 1 exhibits excellent characteristics in terms of driving voltage and efficiency in the organic light emitting device as compared to the compound having a spirofluorene xanthene skeleton.

Specifically, when Experimental Examples 1-1 to 1-15 are compared with Comparative Examples 1-2, 1-5, 1-7, 1-8, and 1-9, it can be confirmed that the compound in which only one substituent is substituted with the diphenyl xanthene skeleton as in Chemical Formula 1 exhibits excellent characteristics in terms of driving voltage, efficiency, and service life in the organic light emitting device as compared to the compound having two or more substituents in the spirofluorene xanthene skeleton.

Specifically, when Experimental Examples 1-1 to 1-15 are compared with Comparative Examples 1-3, 1-4, 1-7, and 1-10, it can be confirmed that the compound in which Ar1 of the six-membered ring is substituted with the diphenyl xanthene skeleton as in Chemical Formula 1 exhibits excellent characteristics in terms of driving voltage, efficiency, and service life in the organic light emitting device as compared to the compound having a 5-membered heterocyclic substituent containing nitrogen.

Specifically, when Experimental Examples 1-1 to 1-15 are compared with Comparative Example 1-6, it can be confirmed that the compound having a diphenyl xanthene skeleton as in Chemical Formula 1 exhibits excellent characteristics in terms of driving voltage and service life in the organic light emitting device as compared to the compound having a diphenylfluorene skeleton.

Specifically, when Experimental Examples 1-1 to 1-15 are compared with Comparative Example 1-12, it can be confirmed that the compound having a diphenyl xanthene skeleton as in Chemical Formula 1 exhibits excellent characteristics in terms of efficiency and service life in the organic light emitting device as compared to the heteroaryl compound substituted with xanthene ring benzene.

The compound represented by Chemical Formula 1 according to an exemplary embodiment of the present specification has excellent thermal stability, a deep HOMO level of 6.0 eV or more, a high triplet energy (ET), and hole stability and thus may exhibit excellent characteristics.

In an exemplary embodiment of the present specification, when the compound represented by Chemical Formula 1 is used in the organic material layer which may simultaneously inject and transport electrons, the compound may be used in a mixture with an n-type dopant used in the art.

Accordingly, the compound represented by Chemical Formula 1 according to an exemplary embodiment of the present specification may have low driving voltage and high efficiency, and may improve stability of the device by hole stability of the compound.

Experimental Example 2

The HOMO energy and LUMO energy values of the compounds represented by the following Chemical Formulae E1, E3, and ET-1-J, which correspond to the compound represented by Chemical Formula 1 according to an exemplary embodiment of the present specification, are shown in the following Table 2.

[E1]

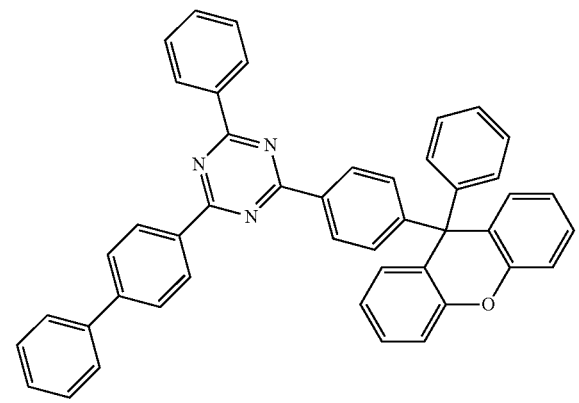

109
-continued

[E3]

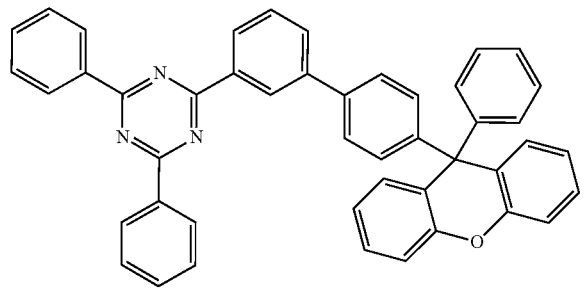

[ET-1-J]

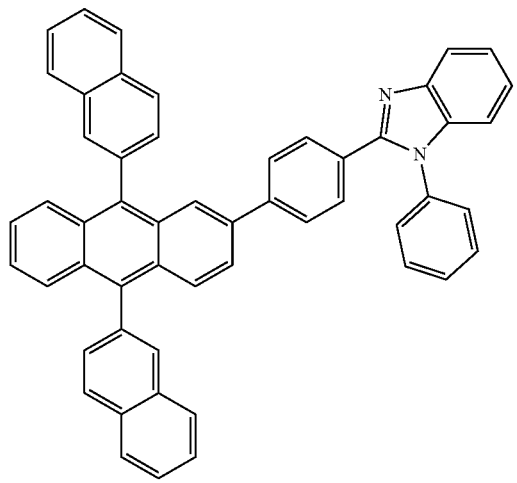

In the Examples of the present specification, the HOMO level was measured by using an atmospheric pressure photoelectron spectrometer (AC3: manufactured by RIKEN KEIKI Co., Ltd.).

In the Examples of the present specification, the LUMO level was calculated as a wavelength value measured via photoluminescence (PL).

TABLE 2

| Chemical Formula | HOMO (eV) | LUMO (eV) |
|---|---|---|
| E1 | 6.22 | 2.96 |
| E3 | 6.18 | 2.93 |
| ET-1-J | 5.70 | 2.87 |

The invention claimed is:

1. A compound represented by the following Chemical Formula 1:

[Chemical Formula 1]

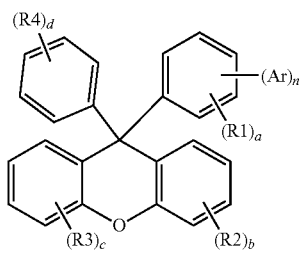

110 in Chemical Formula 1, each Ar is the same as or different from each other, and each independently -L-Ar1, R1 to R4 are the same as or different from each other, and are each independently hydrogen or deuterium, a, b, and c are an integer from 1 to 4, n is 1, d is an integer from 1 to 5, and when a to d are 2 or more, substituents in the parenthesis are the same as or different from each other, L is a direct bond; or a substituted or unsubstituted arylene group, Ar1 is selected from the following structural formulae,

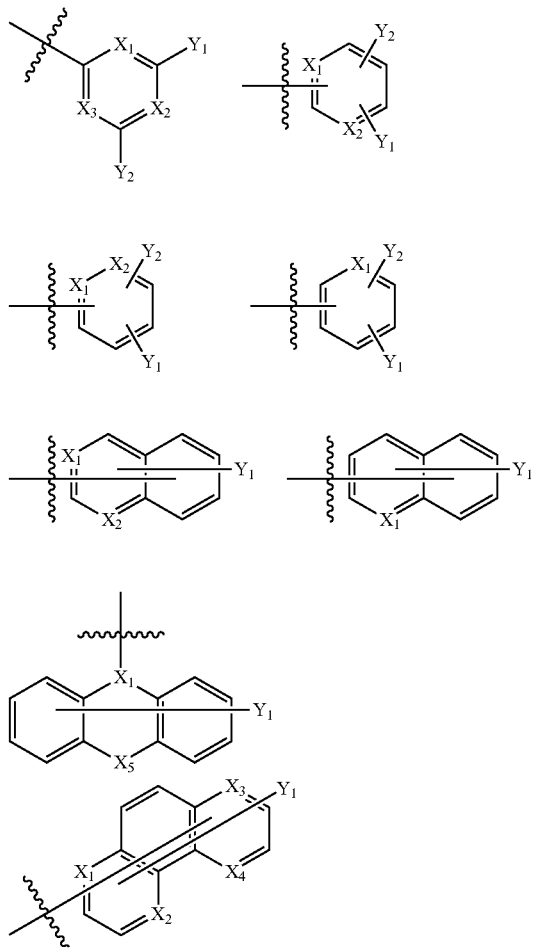

in the structural formulae, $X_1$ to $X_4$ are the same as or different from each other, and are each independently N or CH, and $X_5$ is S or O, $Y_1$ and $Y_2$ are the same as or different from each other, and are each independently hydrogen; deuterium; a nitrile group; a substituted or unsubstituted aryl group; or a substituted or unsubstituted heteroaryl group, and wherein at least one of $X_1$ to $X_4$ of Ar1 is N; or $X_1$ to $X_4$ are all CH and $Y_1$ or $Y_2$ is a nitrile group.

2. The compound of claim 1, wherein Chemical Formula 1 is represented by any one of the following Chemical Formulae 2 to 4:

[Chemical Formula 2]

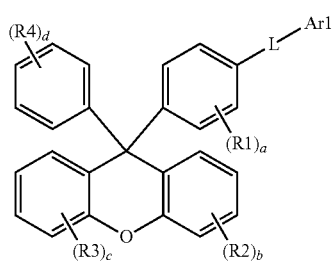

[Chemical Formula 3]

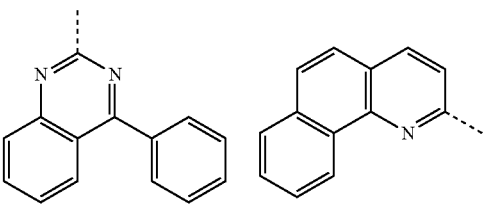

[Chemical Formula 4]

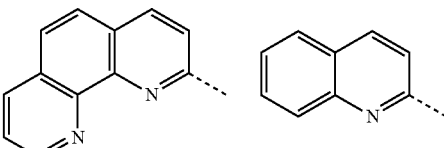

in Chemical Formulae 2 to 4, R1 to R4, a to d, L, and Ar1 are the same as the definitions in Chemical Formula 1.

3. The compound of claim 1, wherein $Y_1$ and $Y_2$ are the same as or different from each other, and are each independently hydrogen; deuterium; a nitrile group; a substituted or unsubstituted phenyl group; a substituted or unsubstituted biphenyl group; a substituted or unsubstituted naphthyl group; a substituted or unsubstituted phenanthryl group; a substituted or unsubstituted pyridine group; or a substituted or unsubstituted dibenzofuranyl group.

4. The compound of claim 1, wherein Ar1 is selected from the following structural formulae:

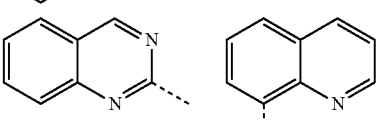

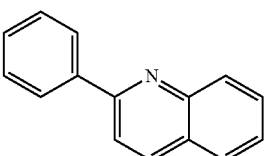

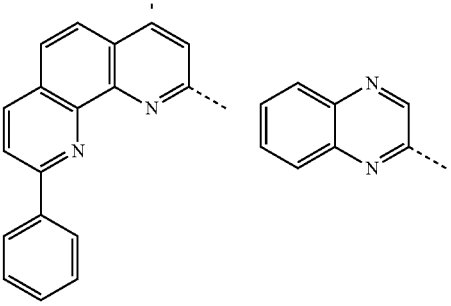

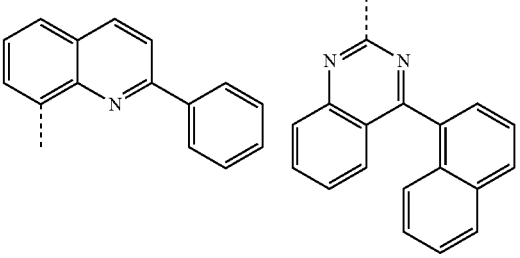

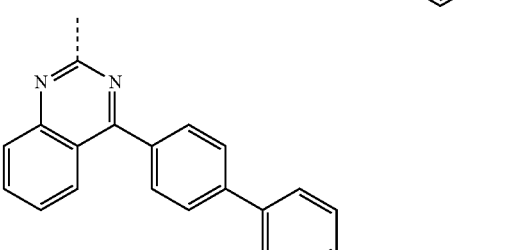

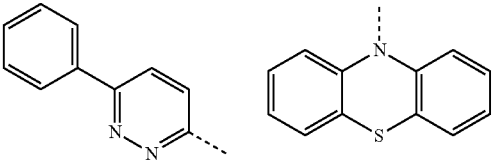

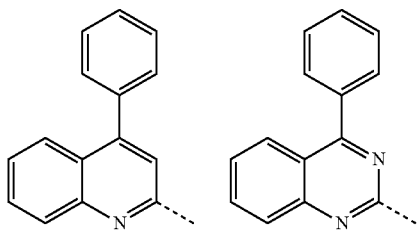

113
-continued
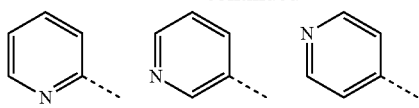
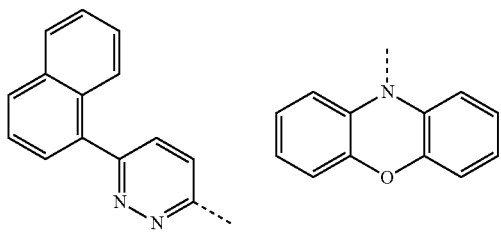
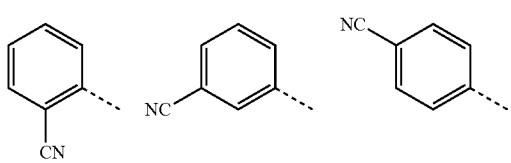
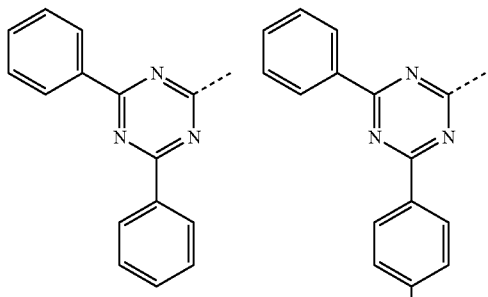
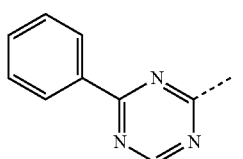
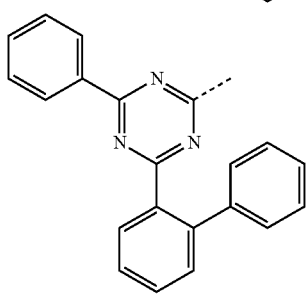
114
-continued
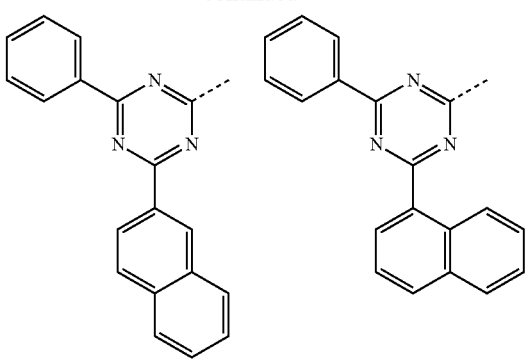
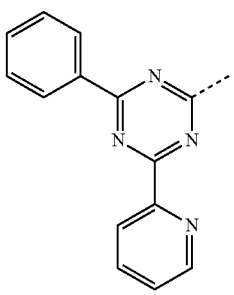
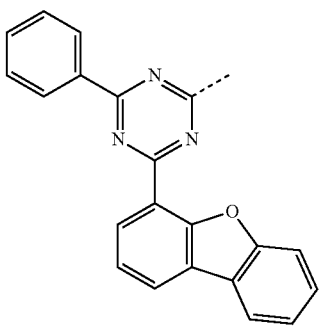
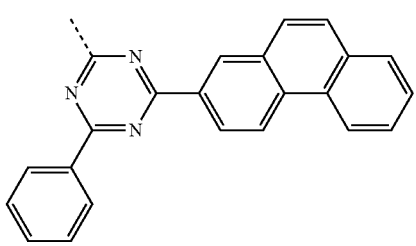
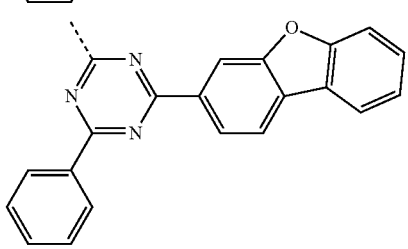

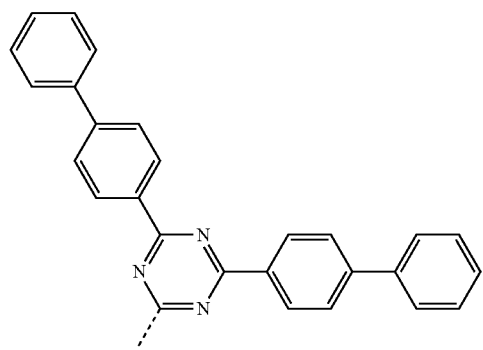
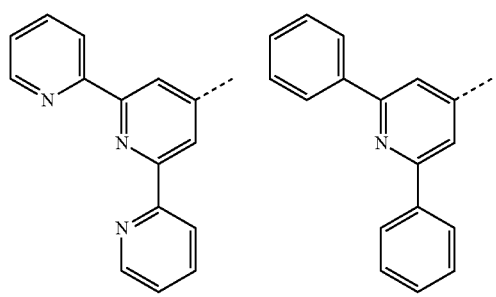
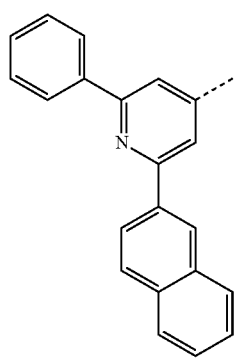
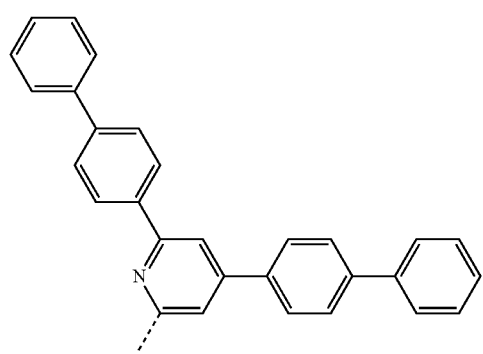
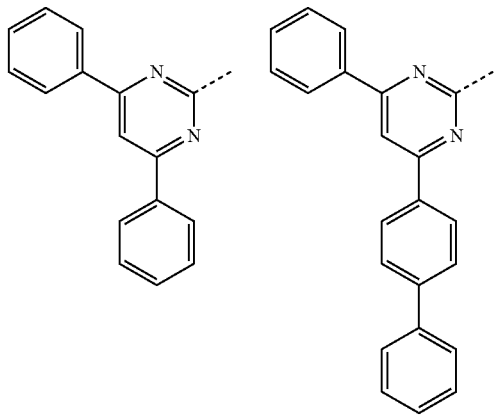
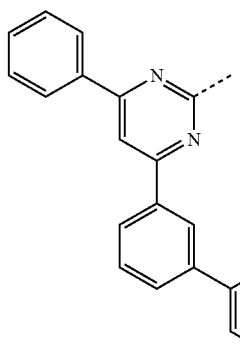
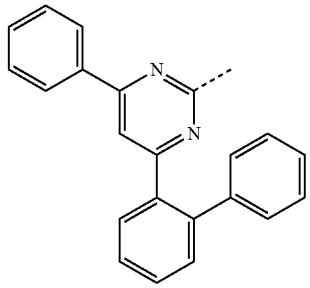
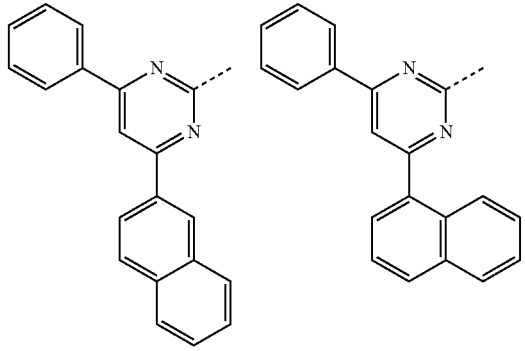
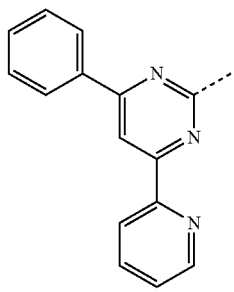

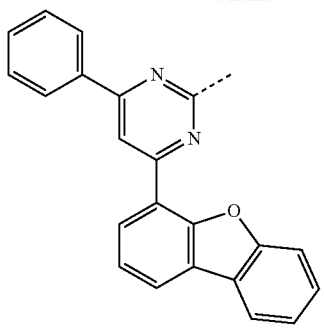
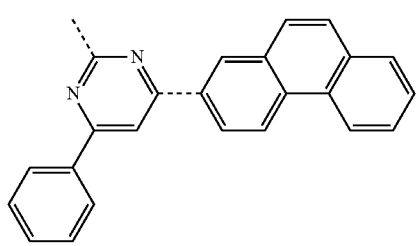
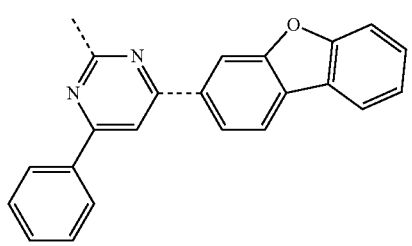
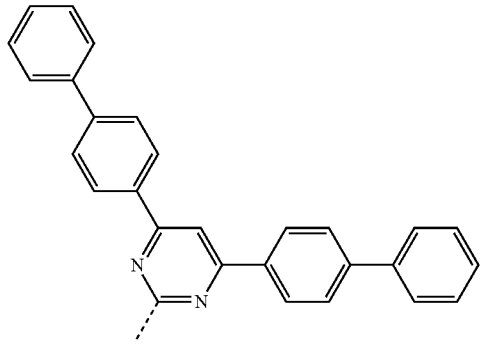
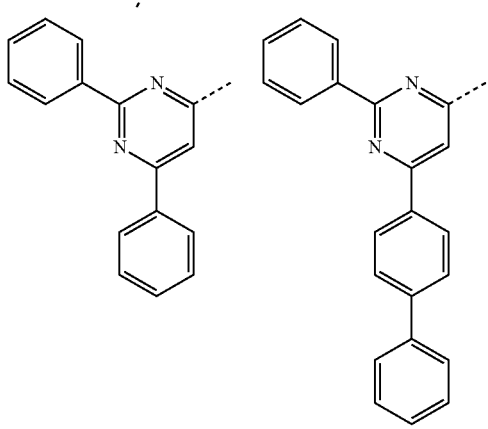
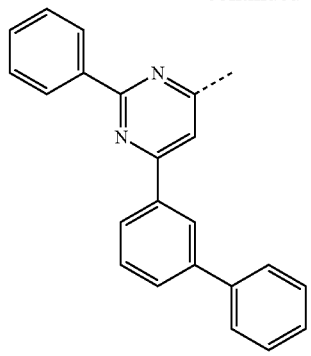
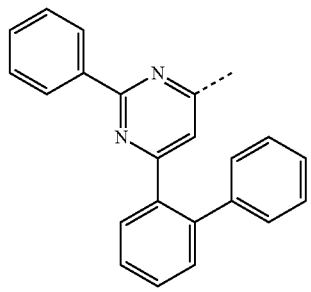
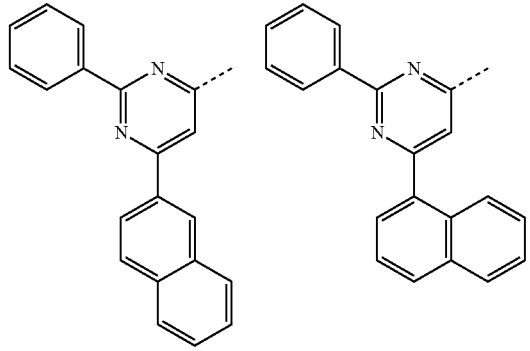
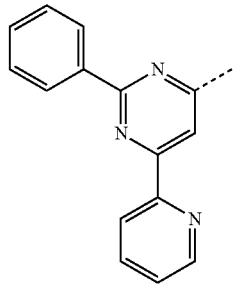
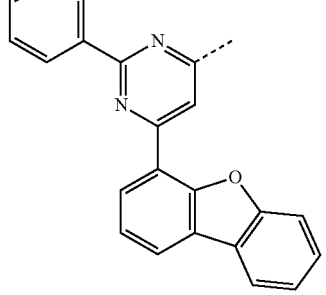

119
-continued
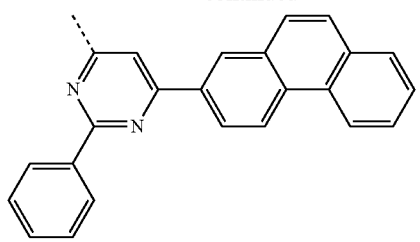
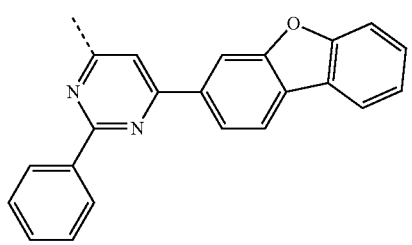
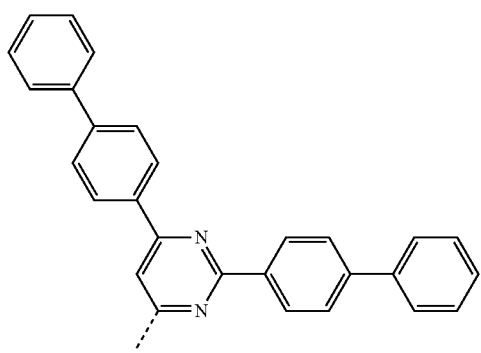
in the structural formulae, a dotted line means a position which is bonded to L.
5. The compound of claim 1, wherein the compound represented by Chemical Formula 1 is any one selected from the following structural formulae:
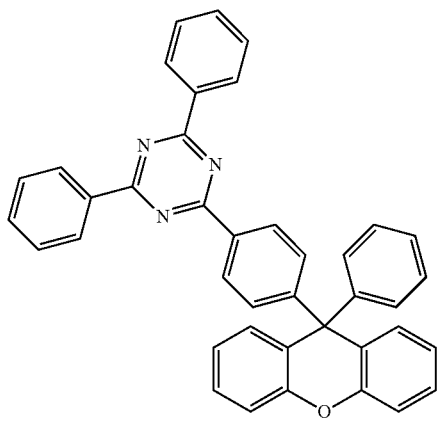
120
-continued
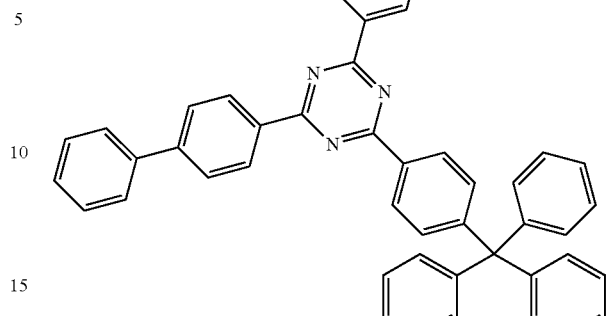
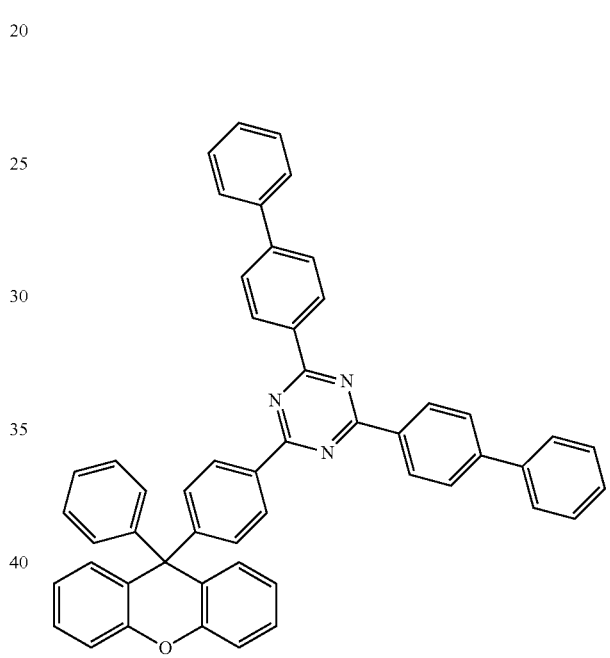
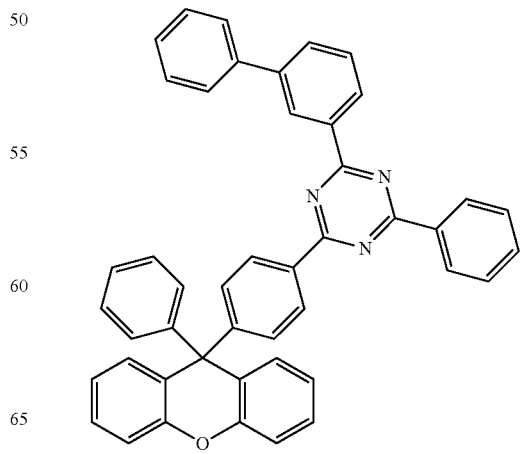

121
-continued
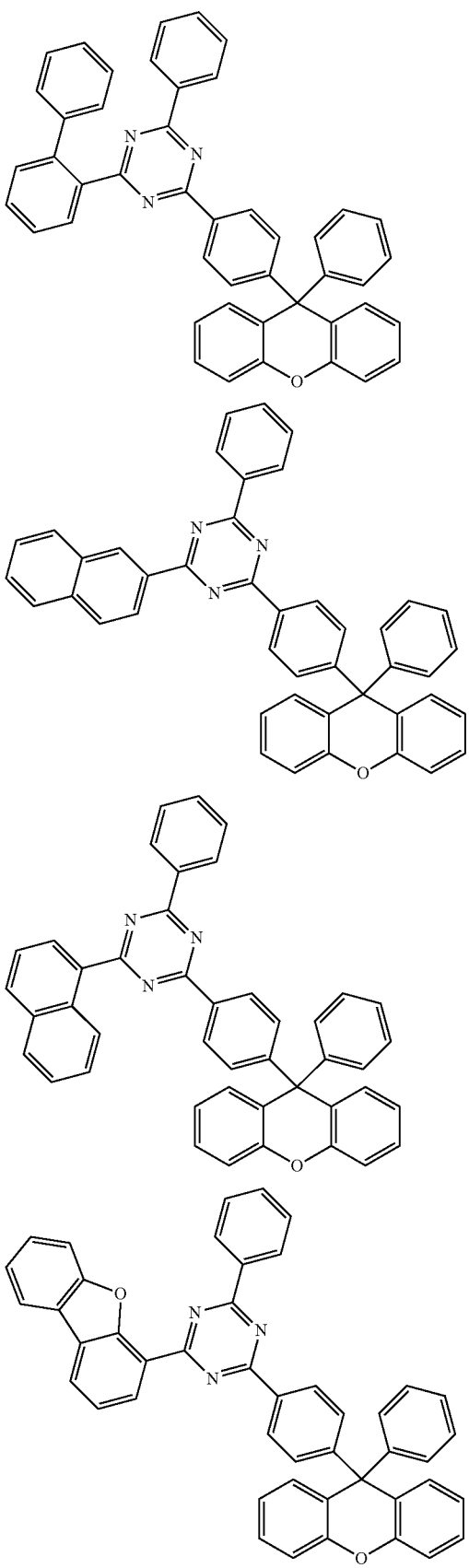
122
-continued
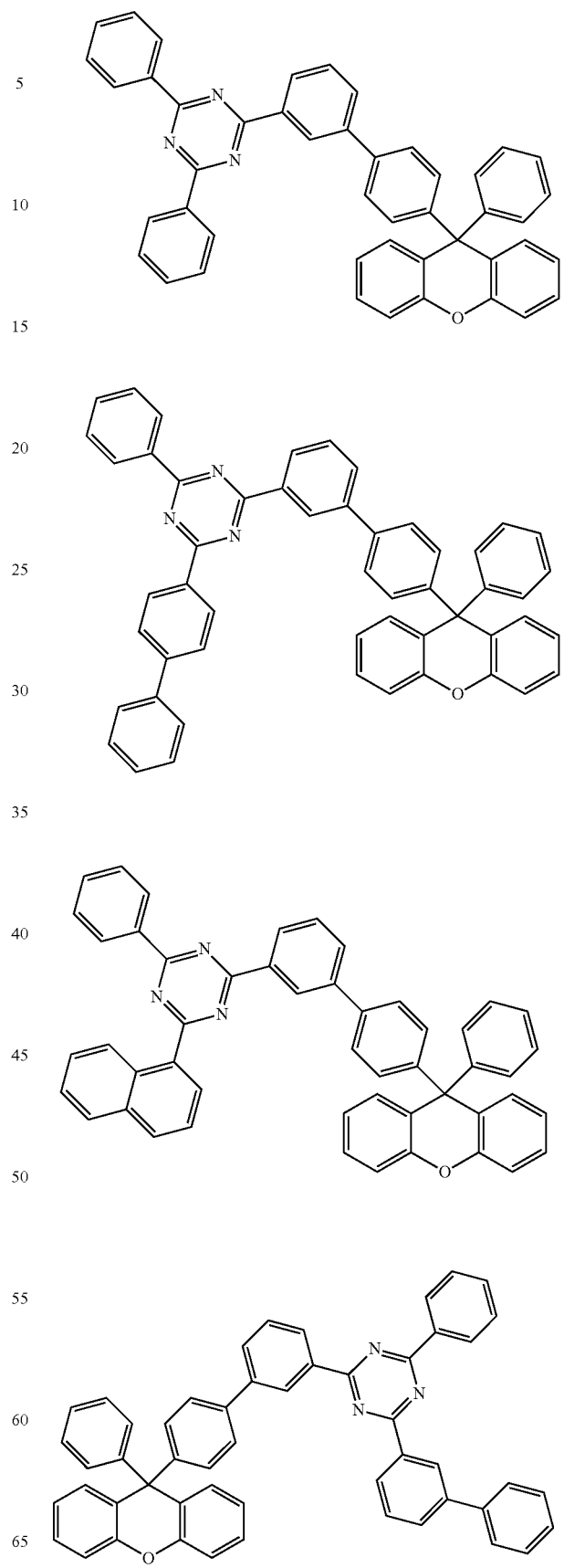

123
-continued
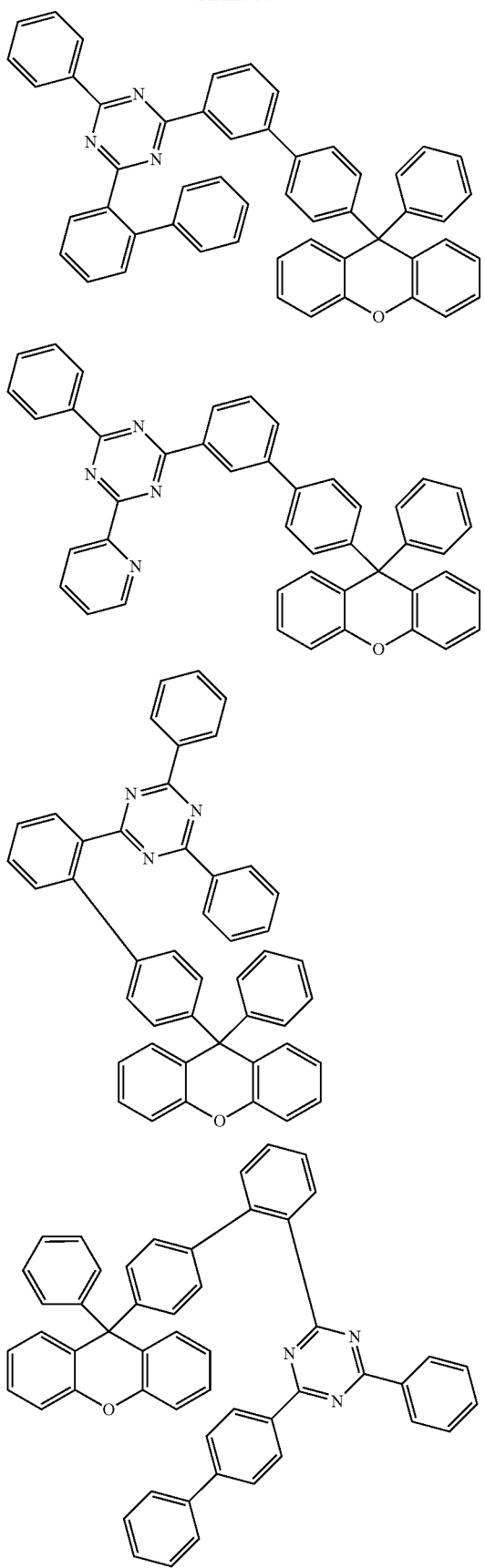
124
-continued
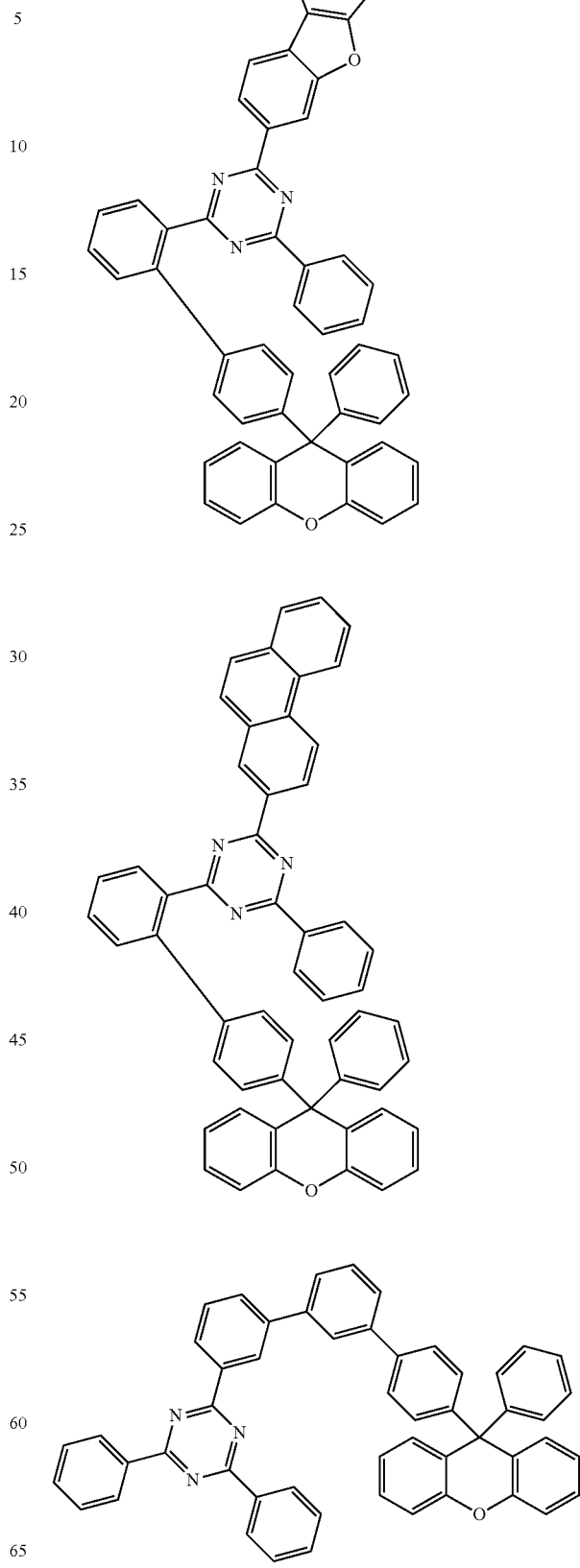

125
-continued
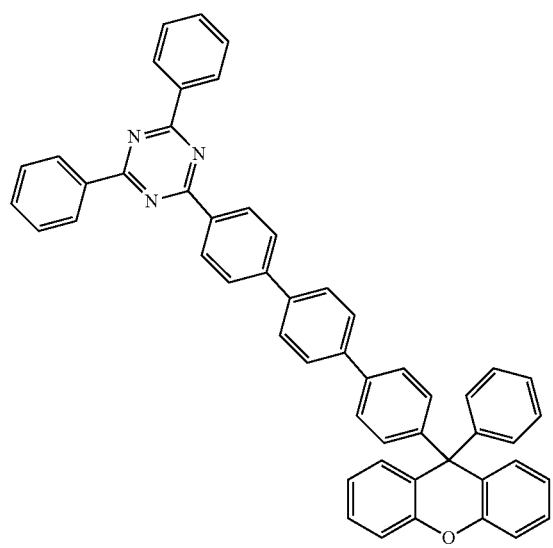 [SMILES: c1ccc(-c2nc(-c3ccccc3)nc(-c3ccc(-c4ccc(-c5ccc(C6(c7ccccc7)c7ccccc7Oc7ccccc76)cc5)cc4)cc3)n2)cc1]
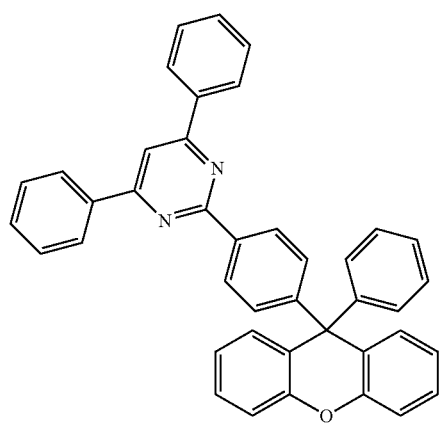
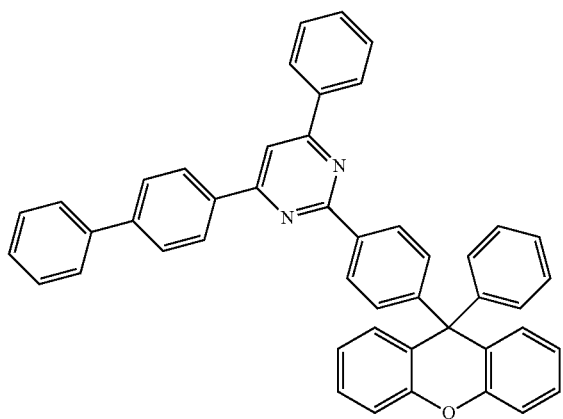
126
-continued
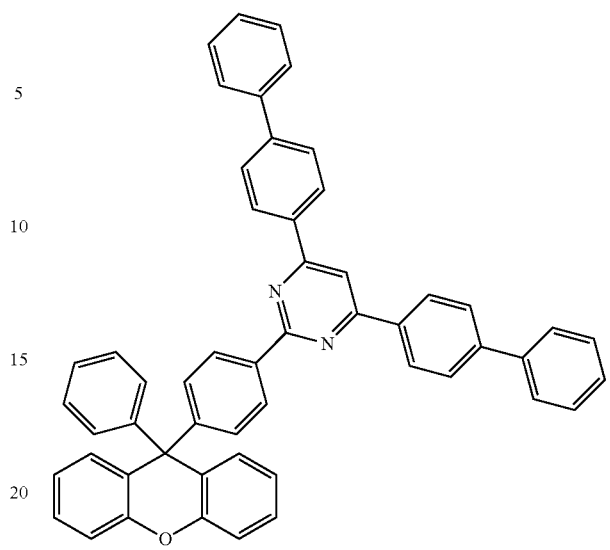
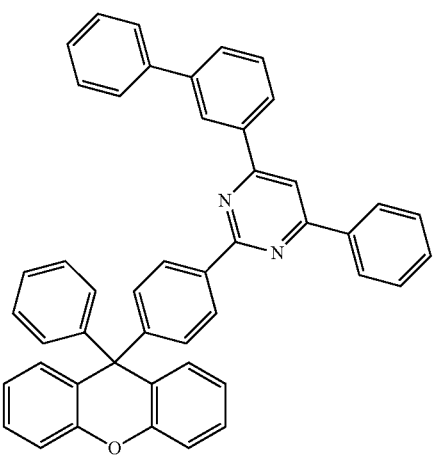
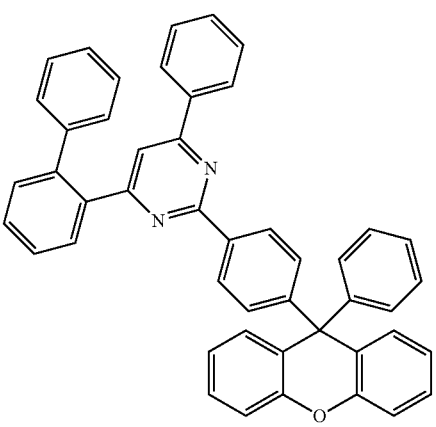

127
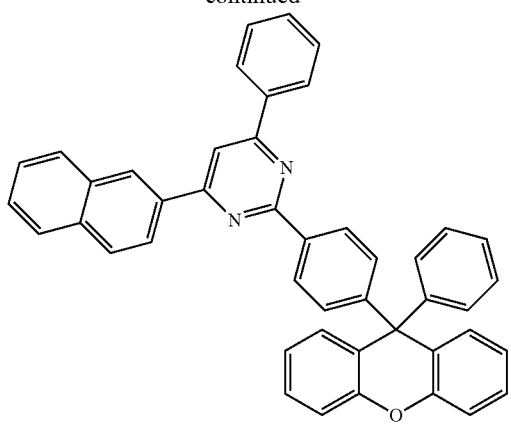
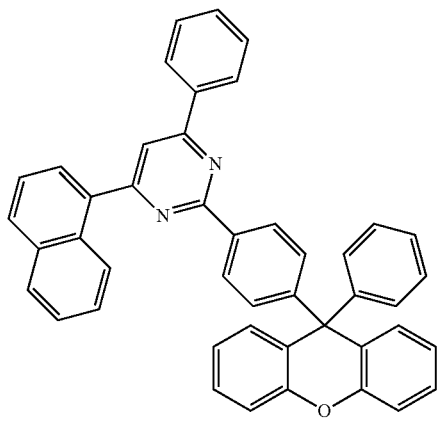
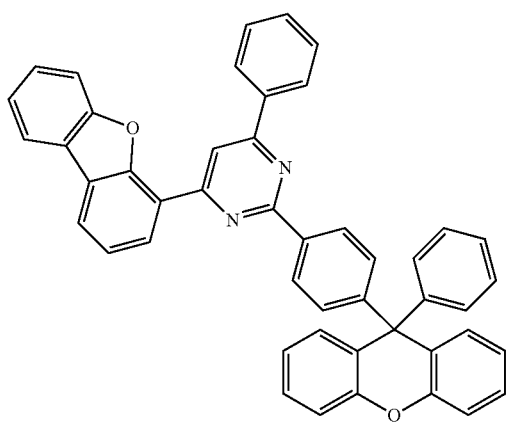
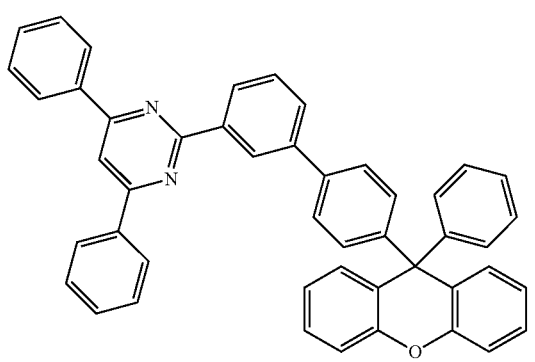
128
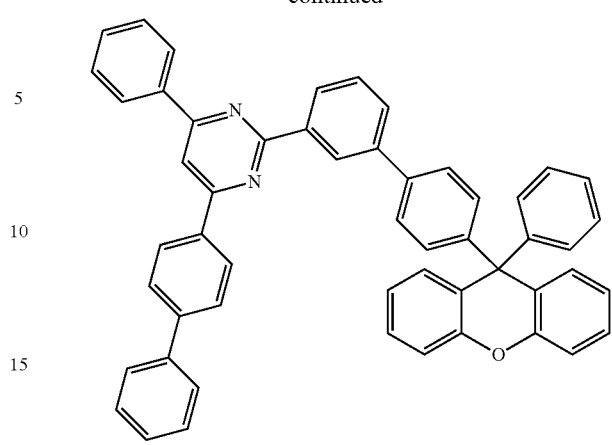
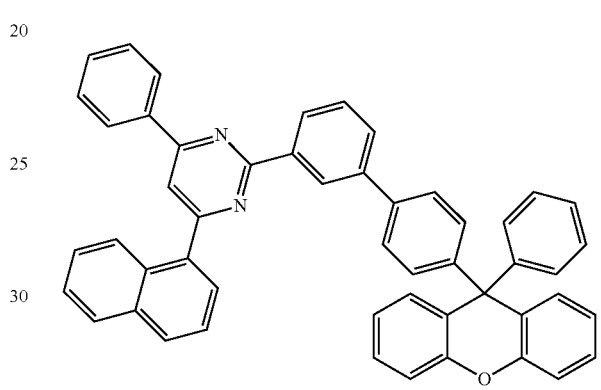
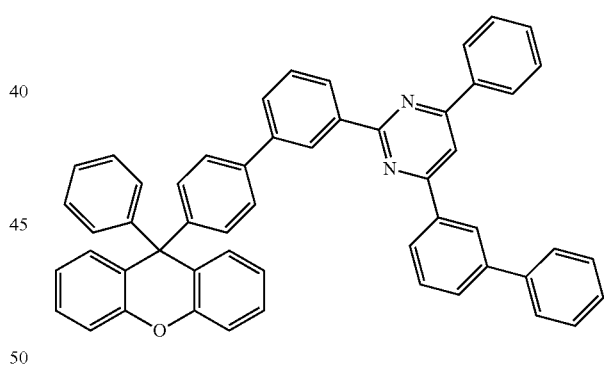
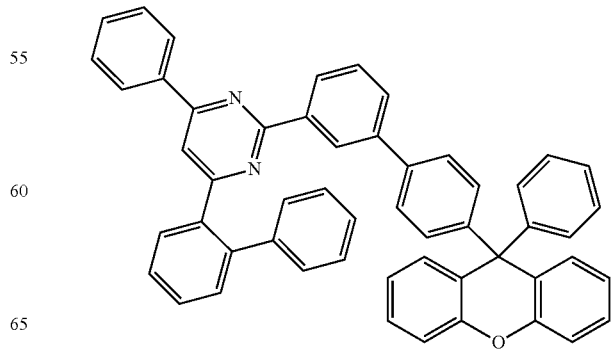

129
-continued
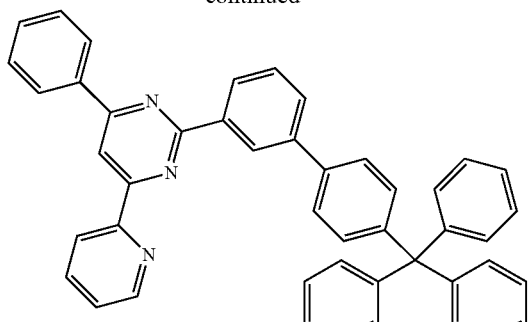
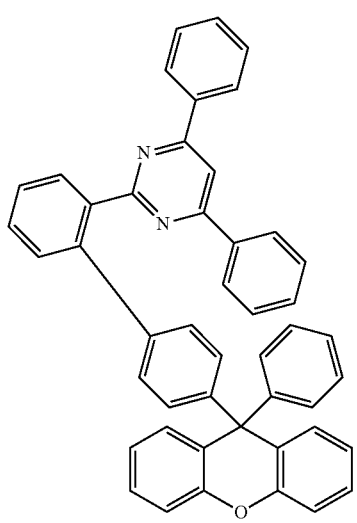
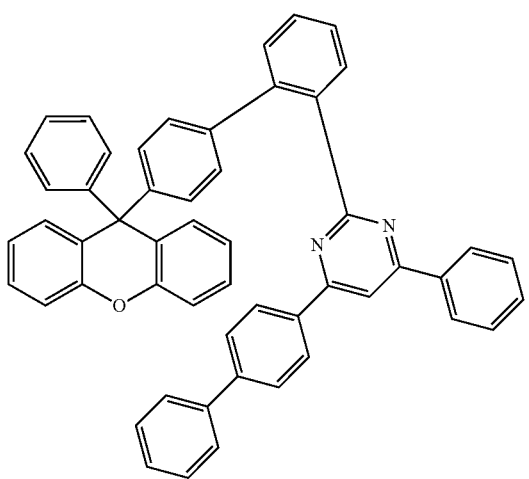
130
-continued
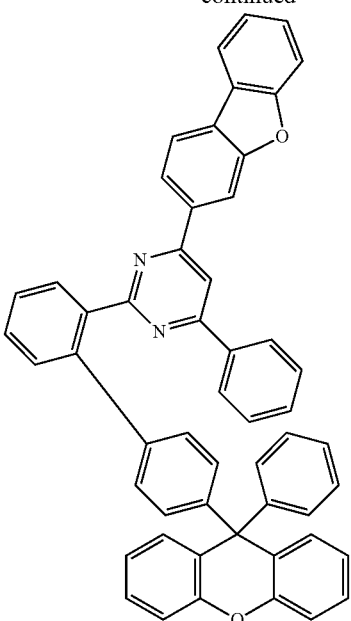
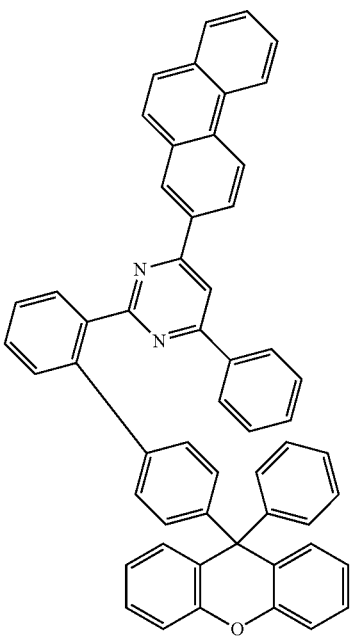
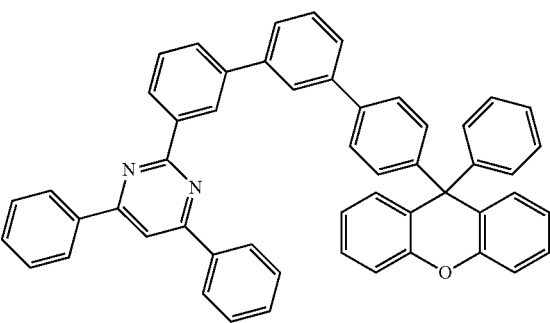

131
-continued
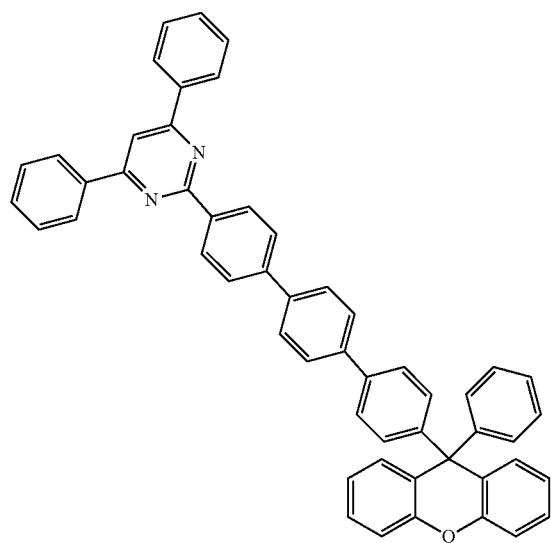 [SMILES: c1ccc(-c2cc(-c3ccccc3)nc(-c3ccc(-c4ccc(-c5ccc(C6(c7ccccc7)c7ccccc7Oc7ccccc76)cc5)cc4)cc3)n2)cc1]
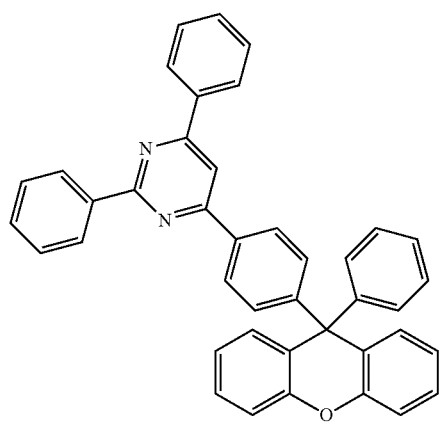
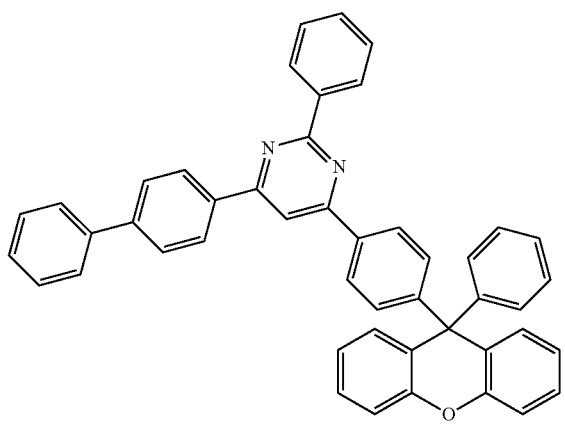
132
-continued
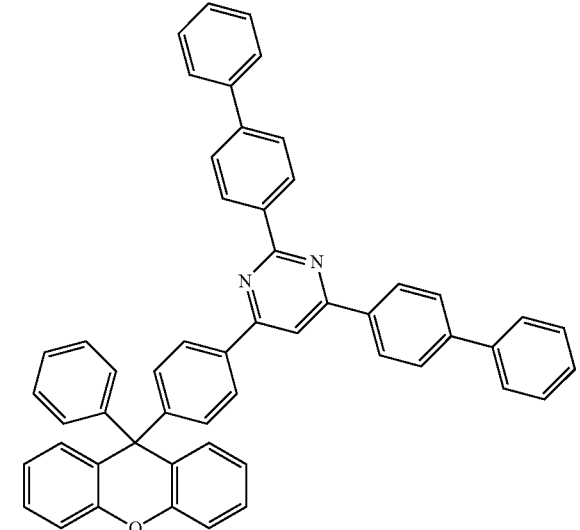
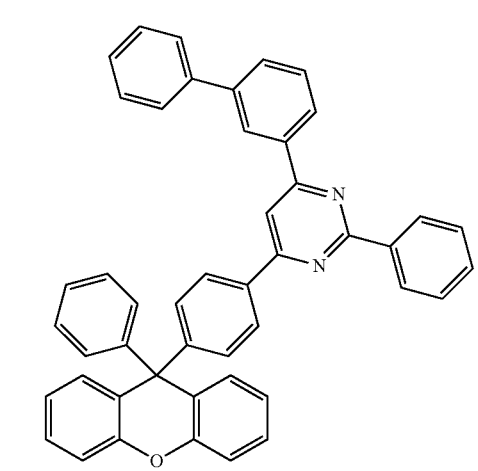
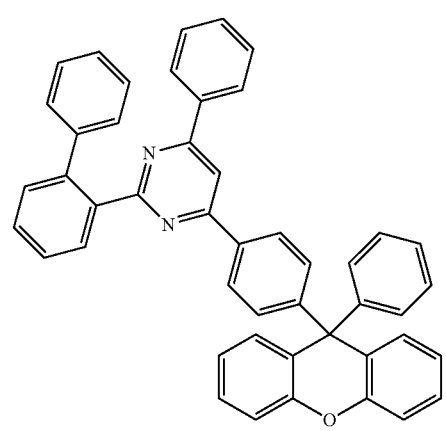

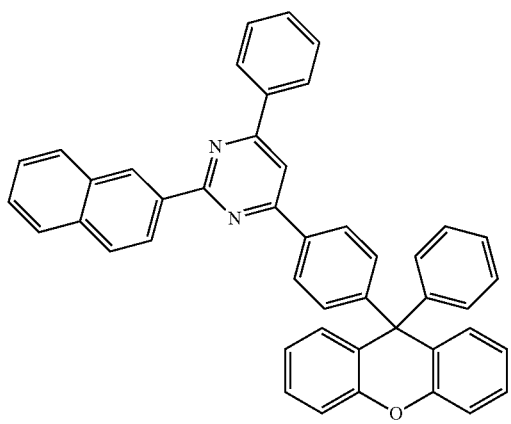
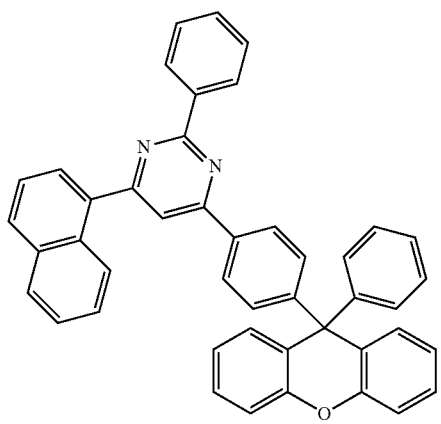
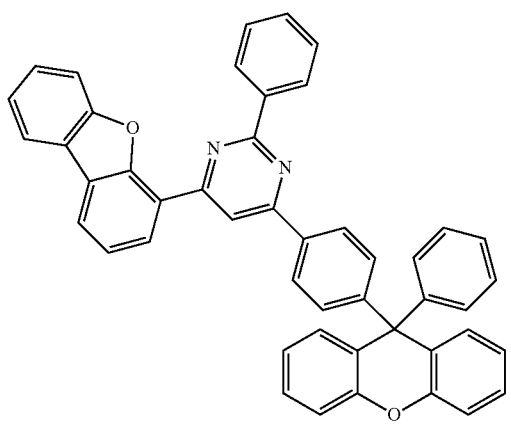
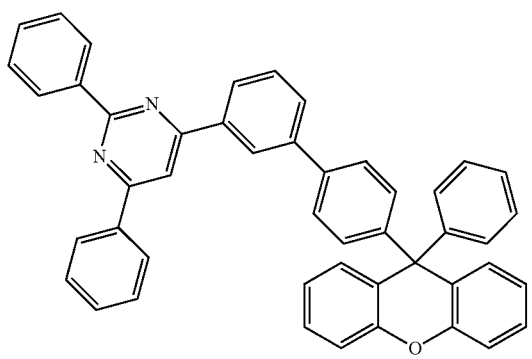
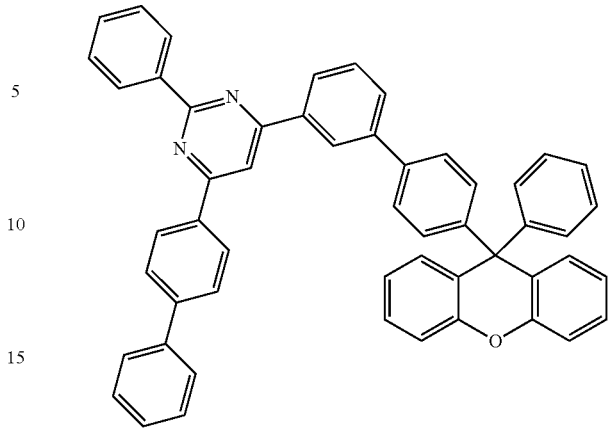
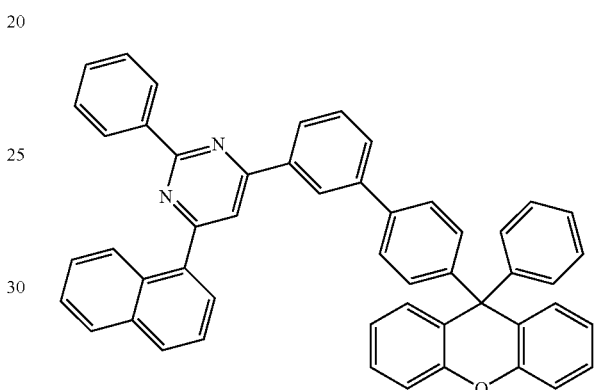
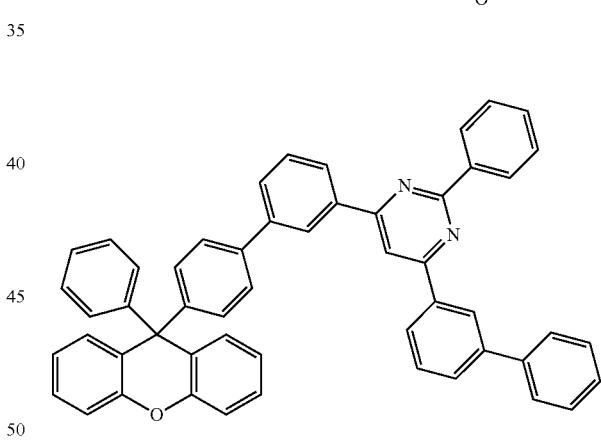
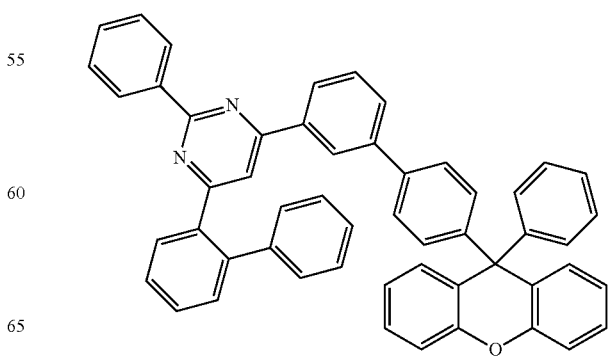

135
-continued
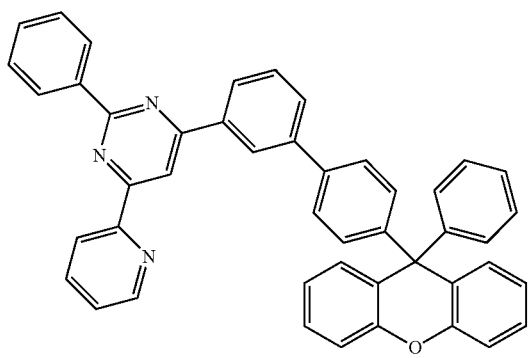
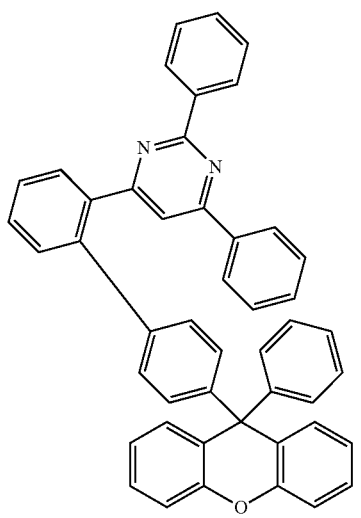
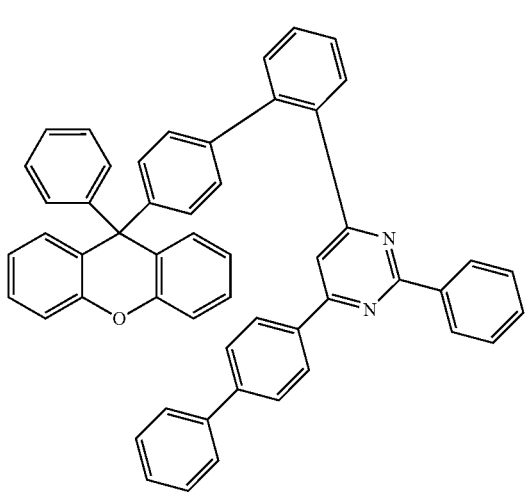
136
-continued
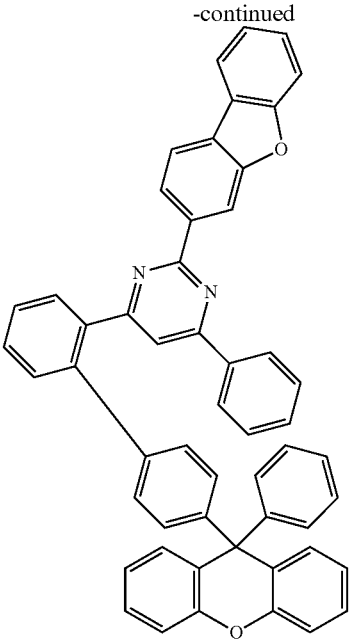
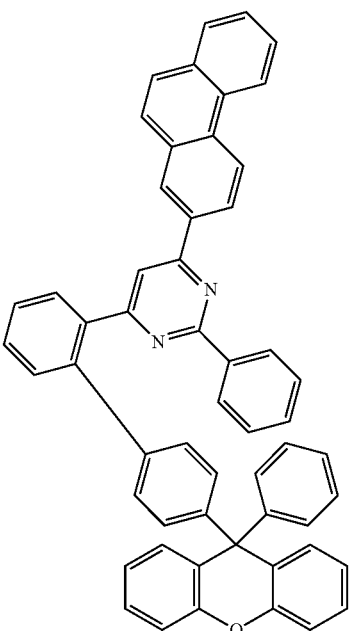
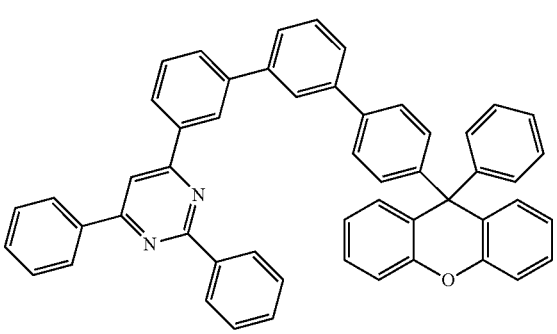

137
-continued
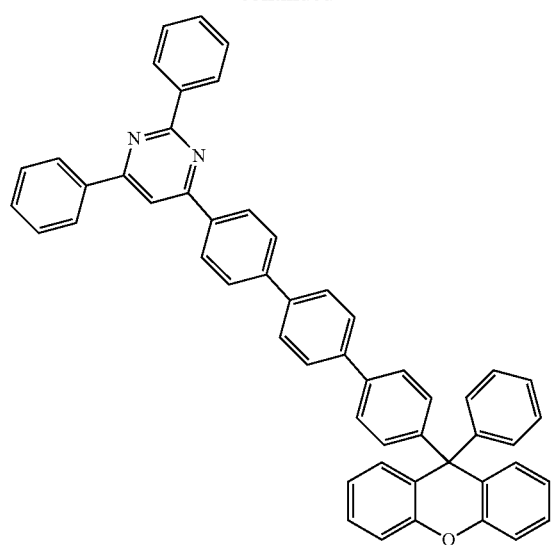 [SMILES: c1ccc(-c2cc(-c3ccc(-c4ccc(-c5ccc(C6(c7ccccc7)c7ccccc7Oc7ccccc76)cc5)cc4)cc3)nc(-c3ccccc3)n2)cc1]
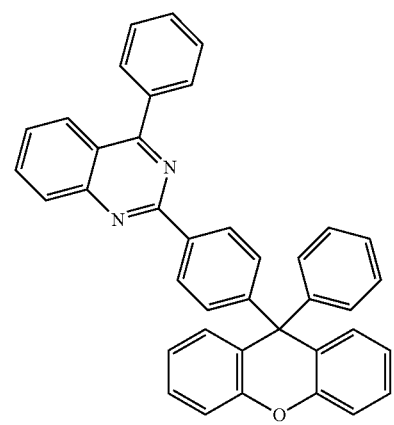
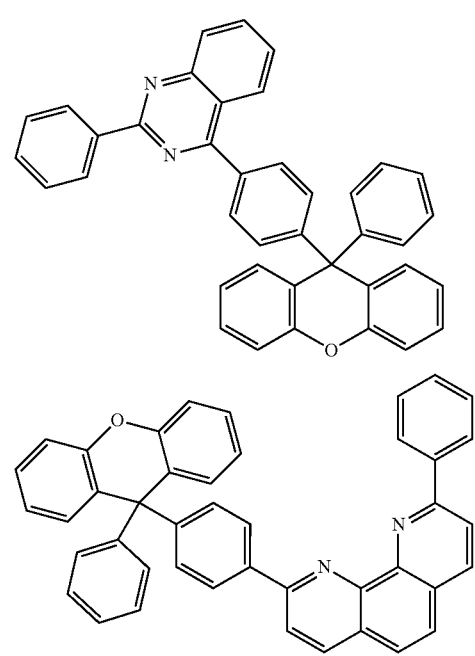
138
-continued
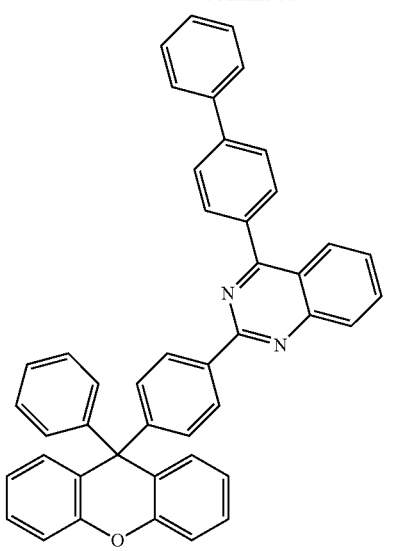
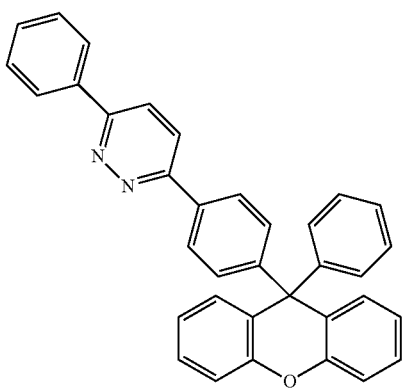
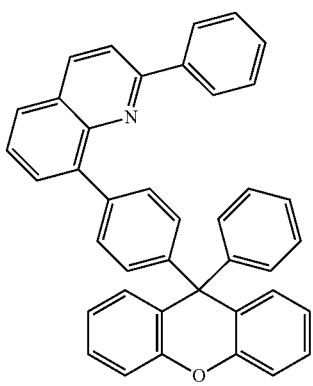

-continued
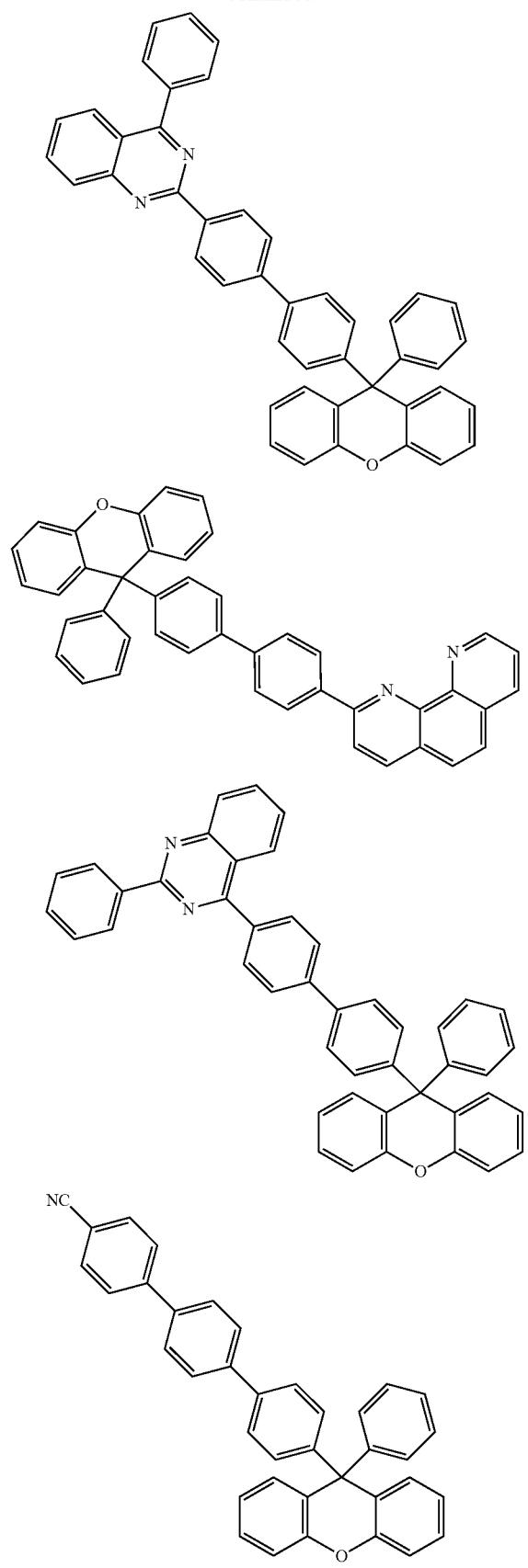
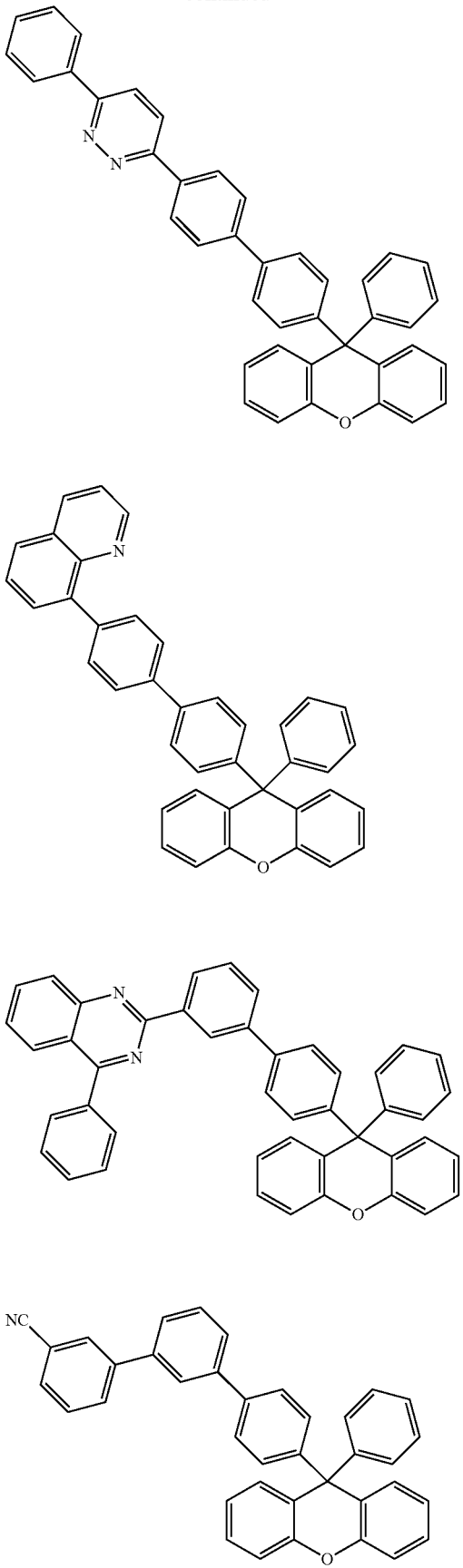

141
-continued
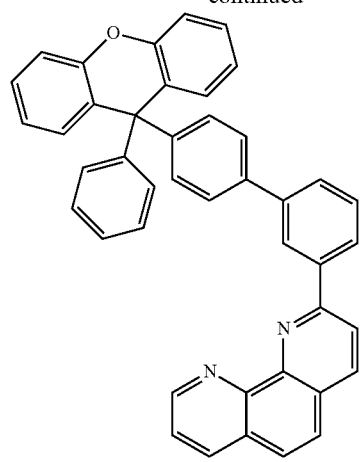
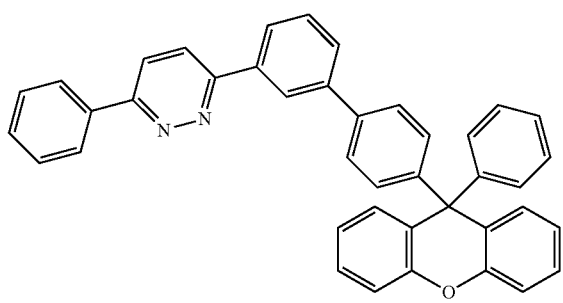
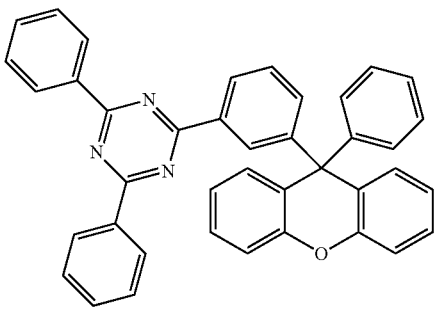
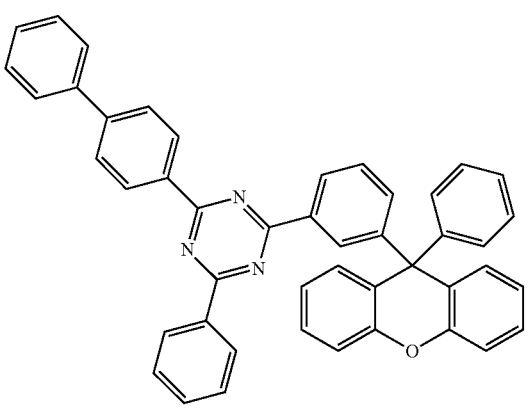
142
-continued
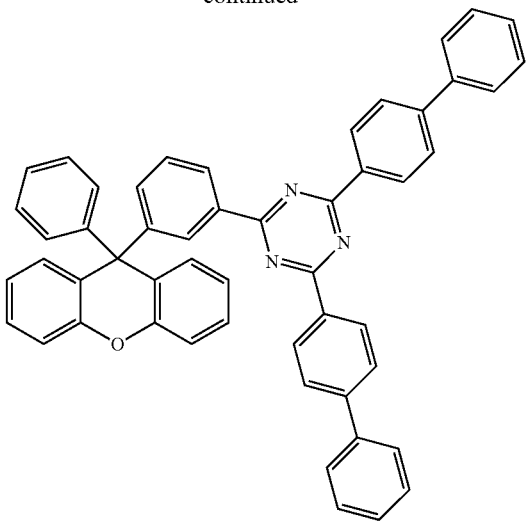
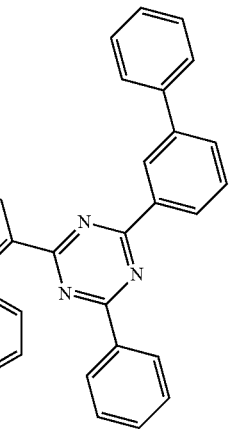
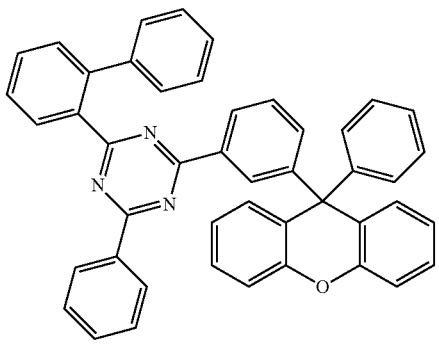
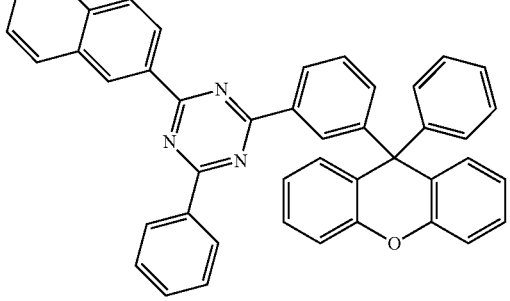

143
-continued
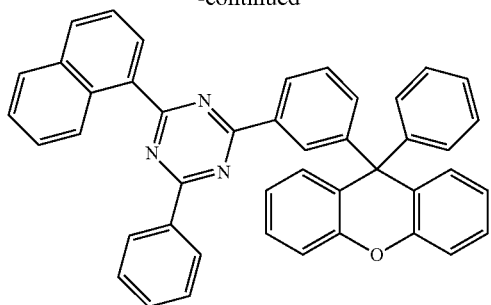
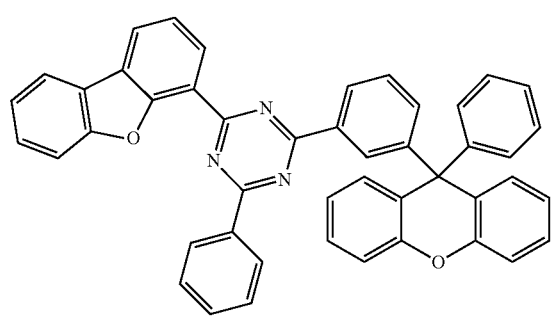
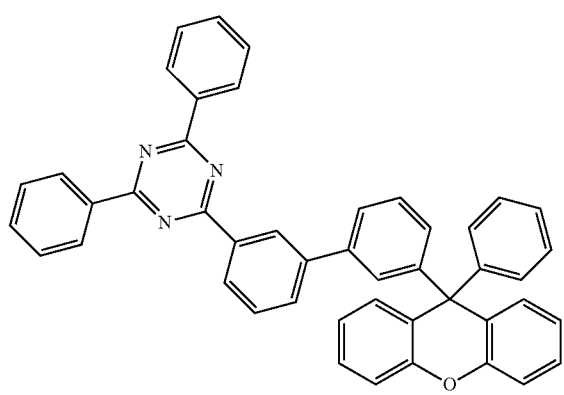
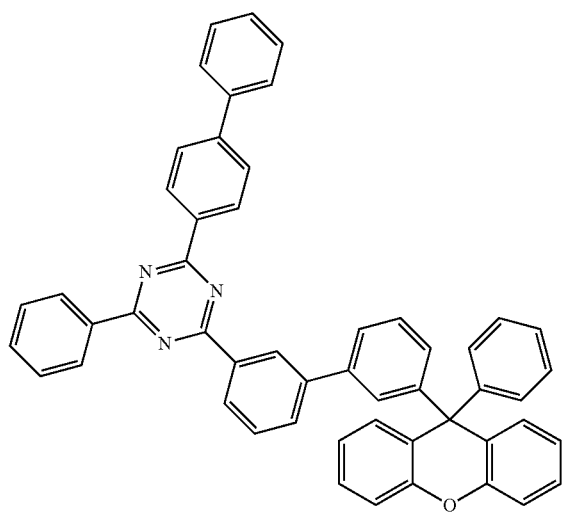
144
-continued
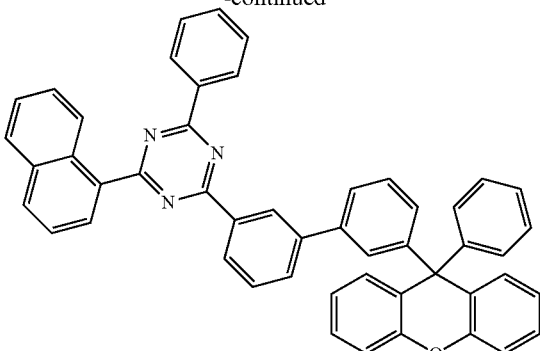
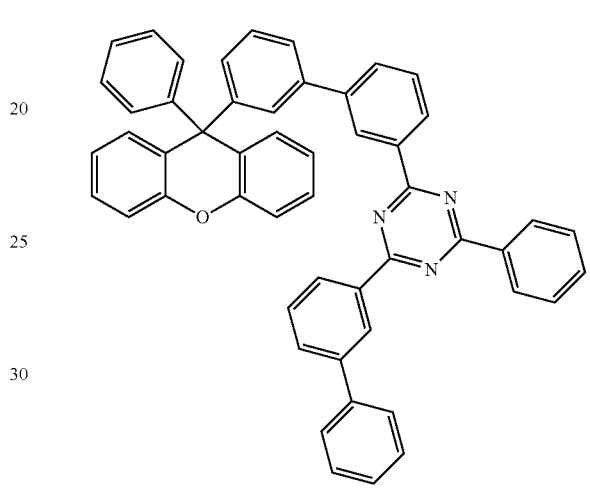
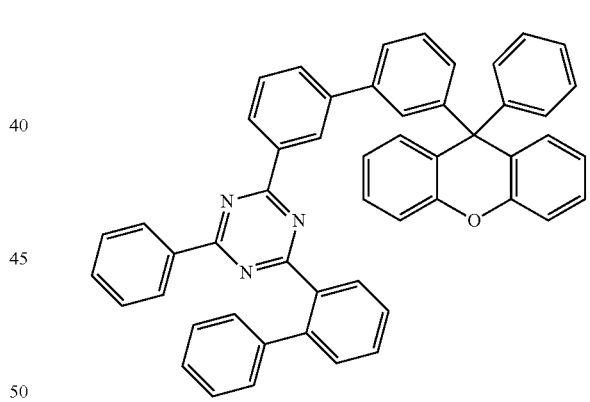
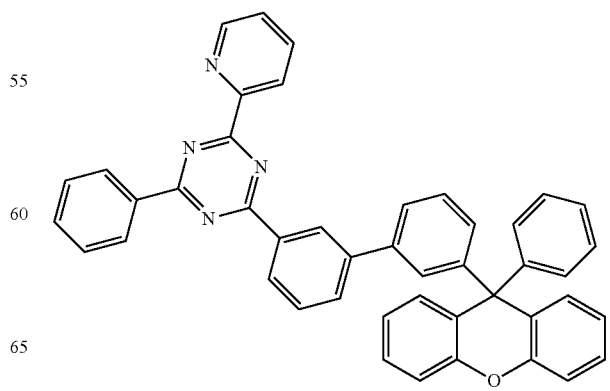

145
-continued
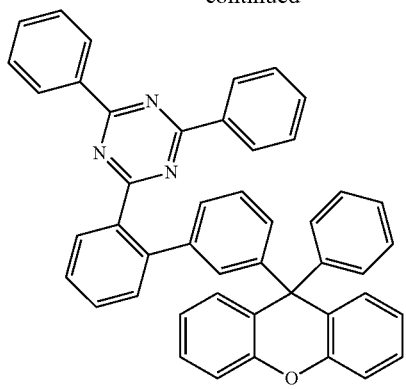
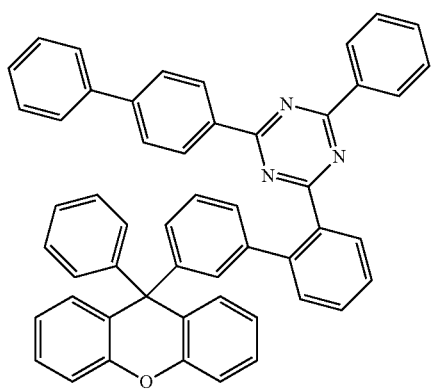
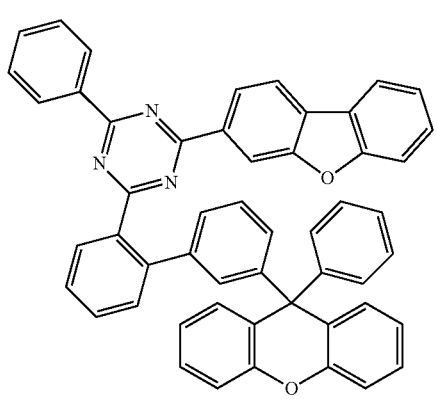
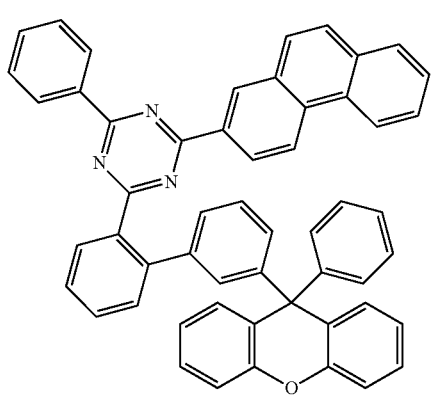
146
-continued
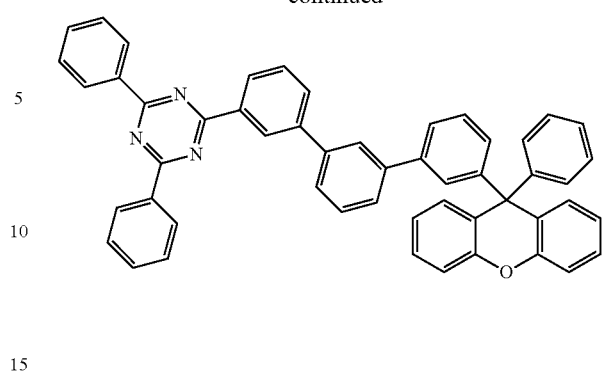
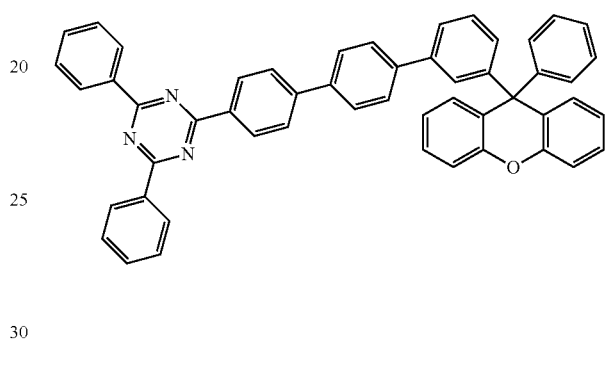
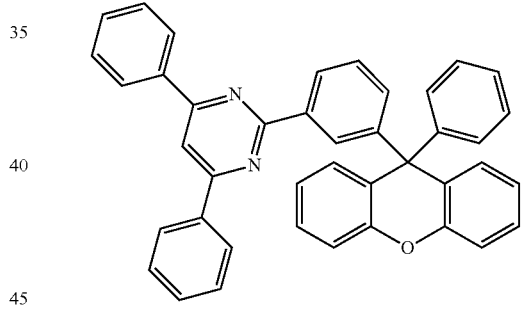
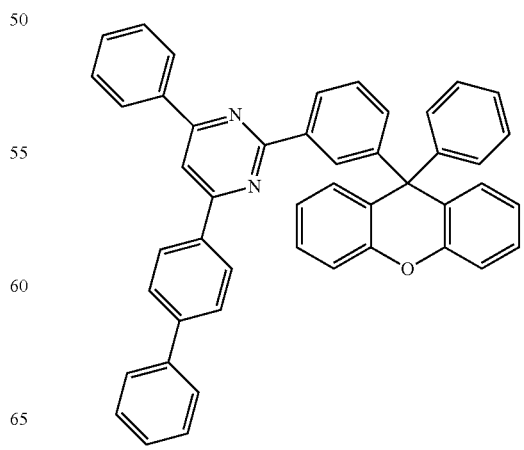

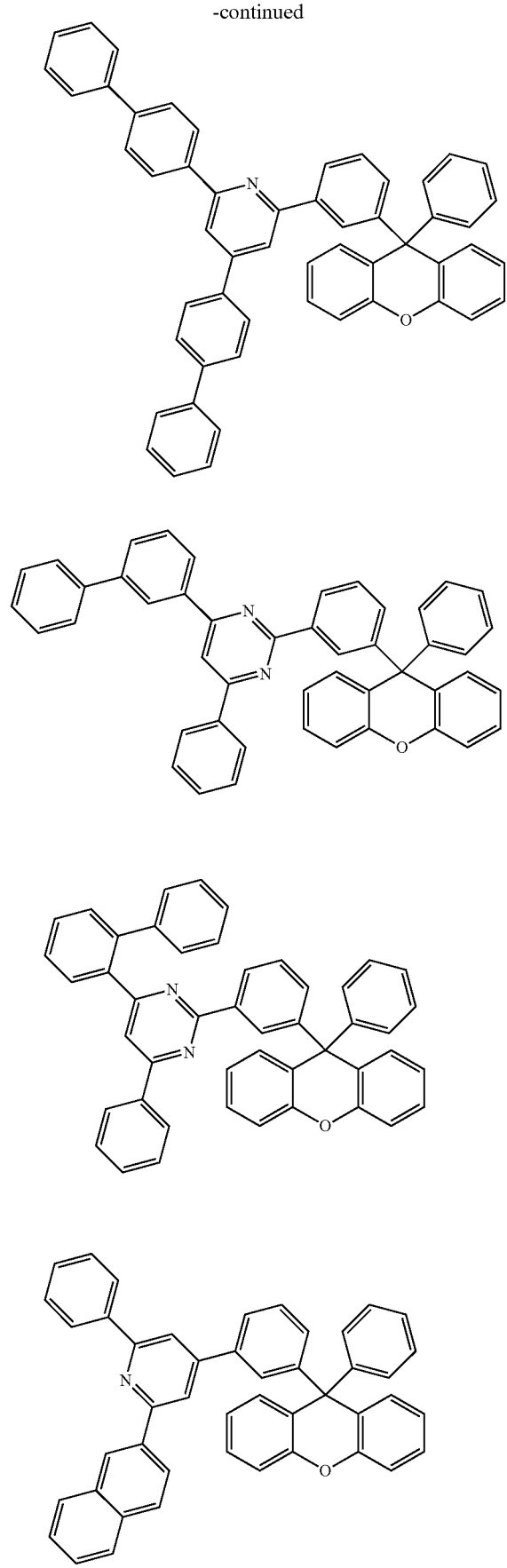
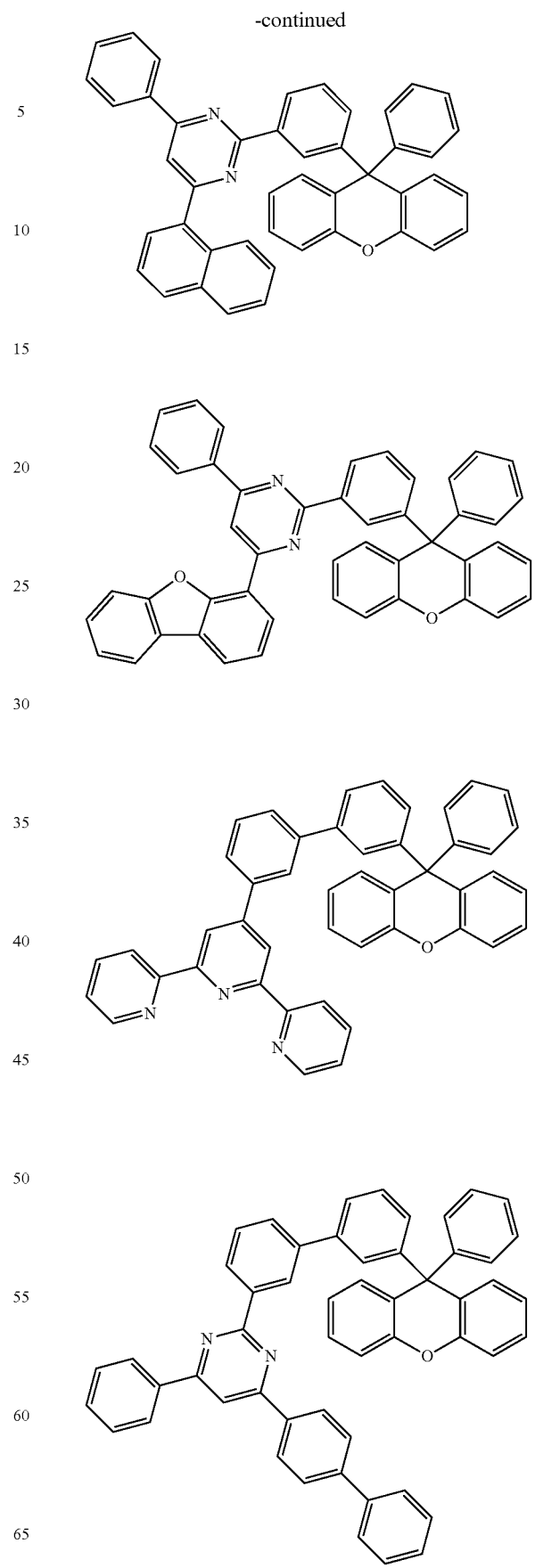

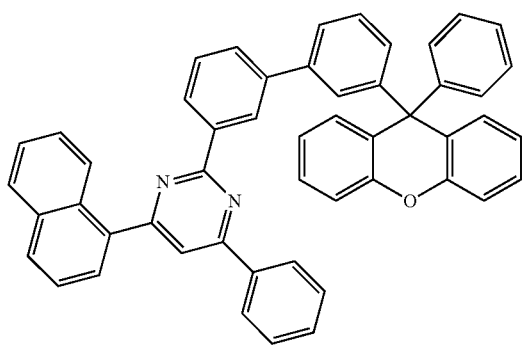
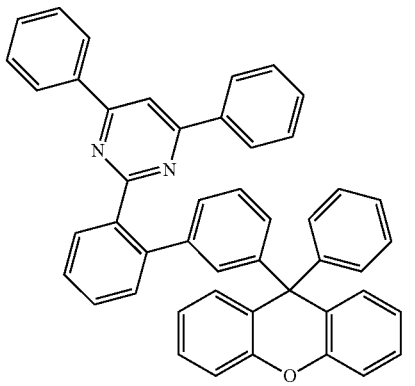
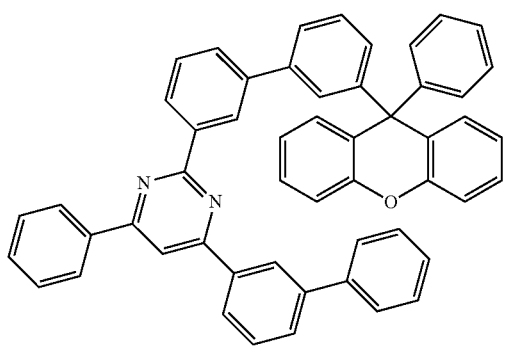
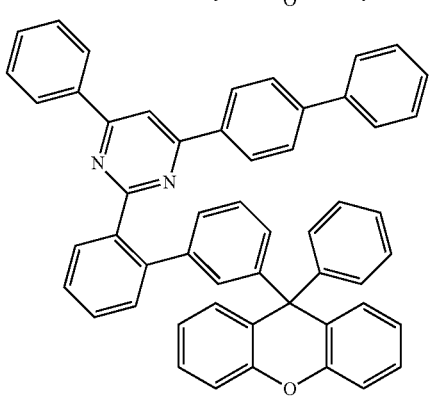
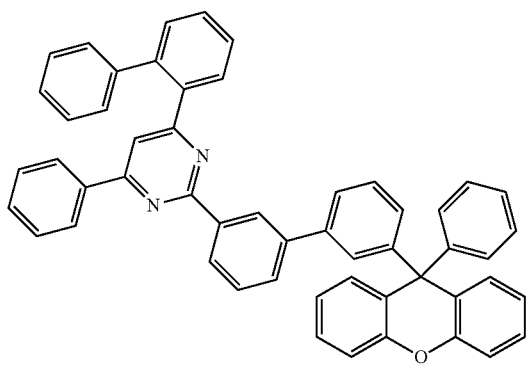
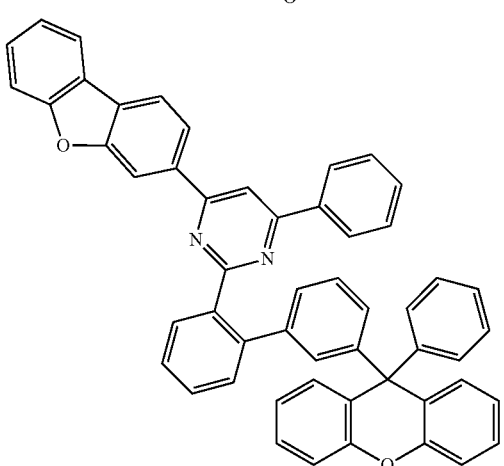
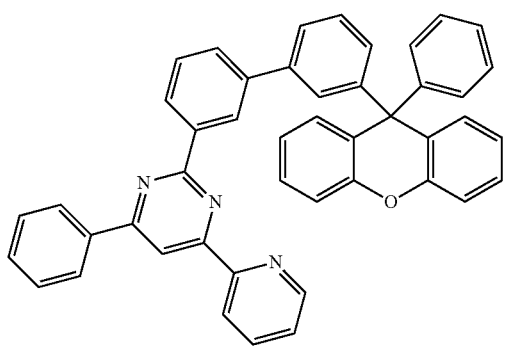
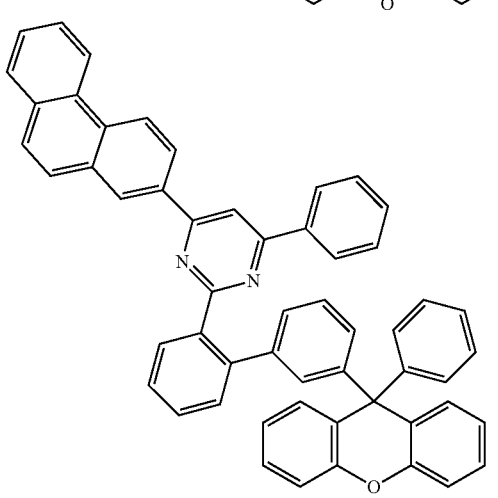
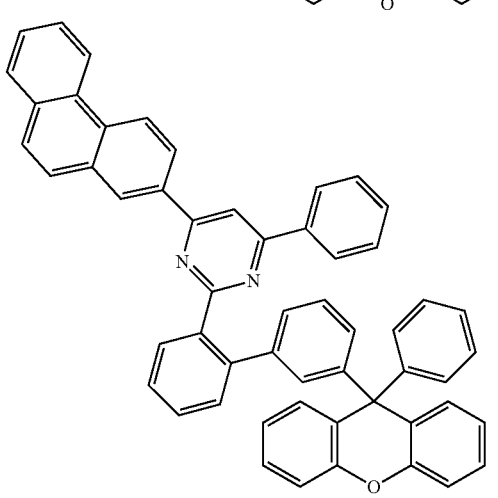

-continued
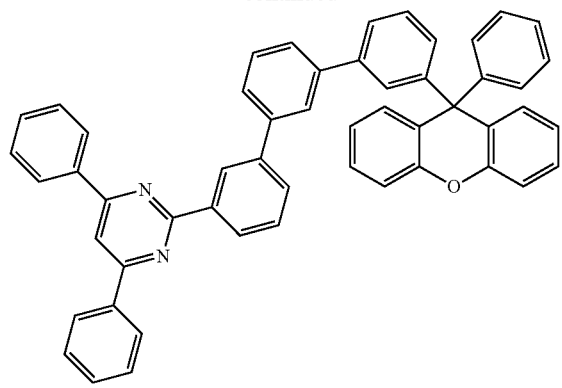
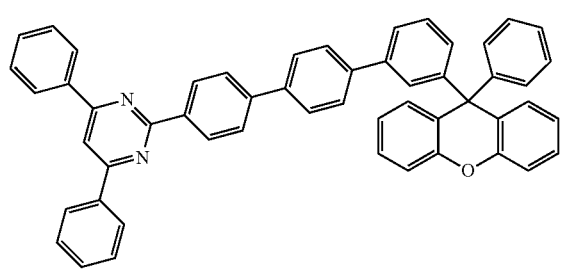
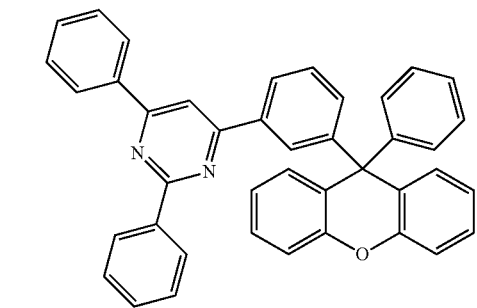
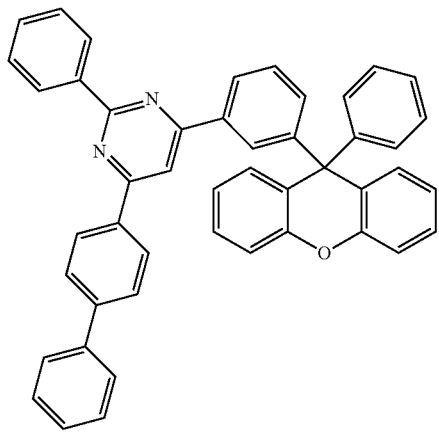
-continued
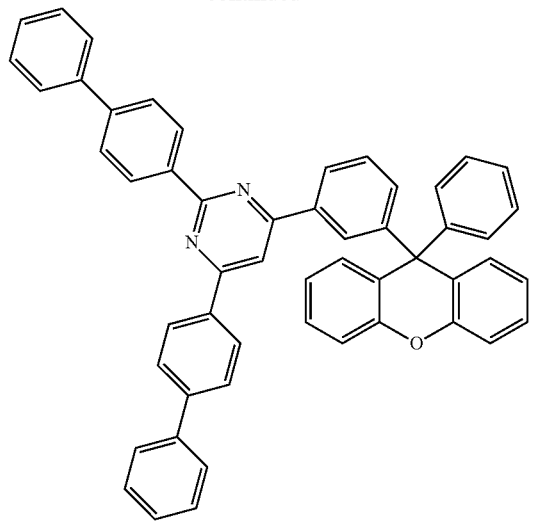
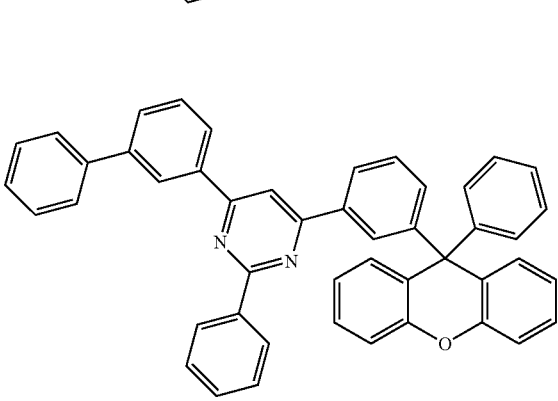
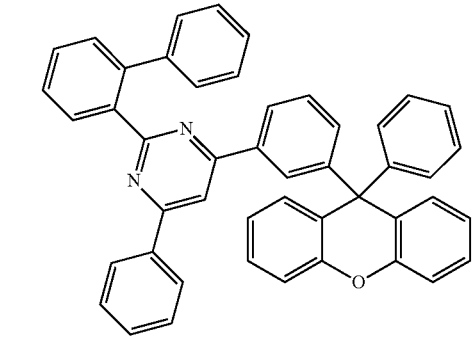
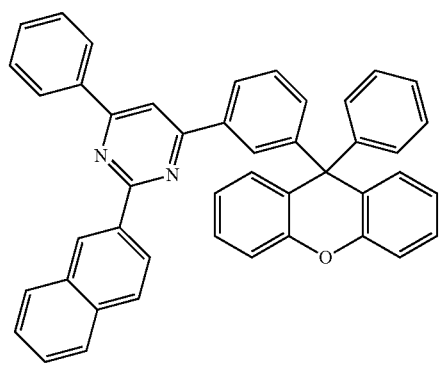

153
-continued
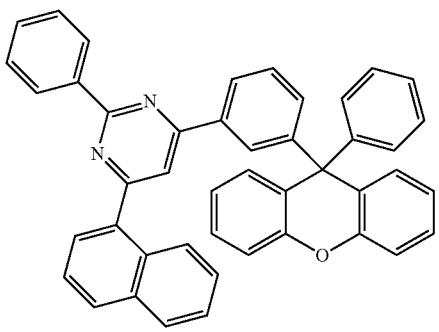
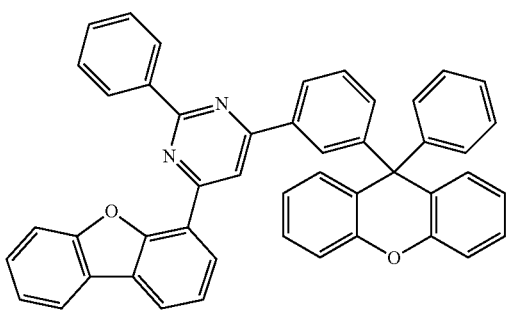
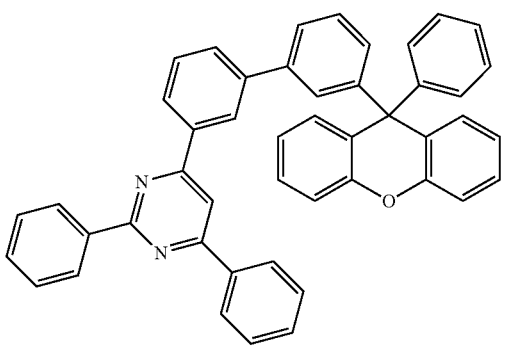
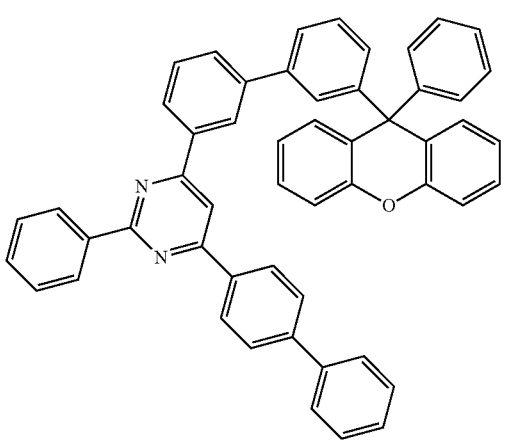
154
-continued
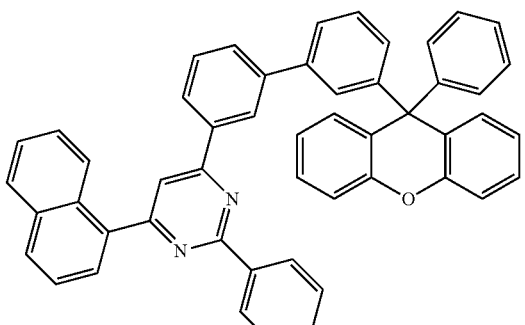
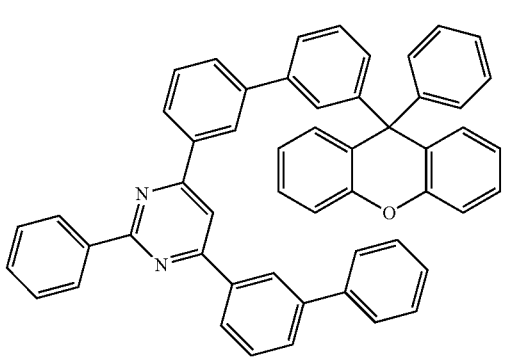
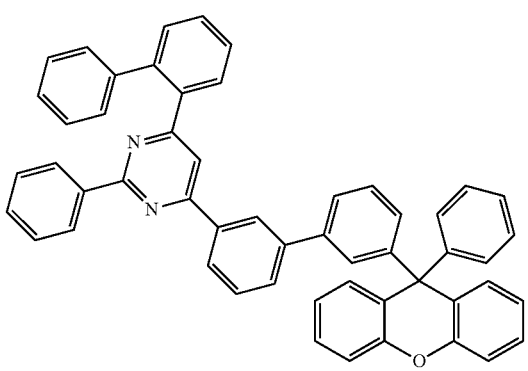
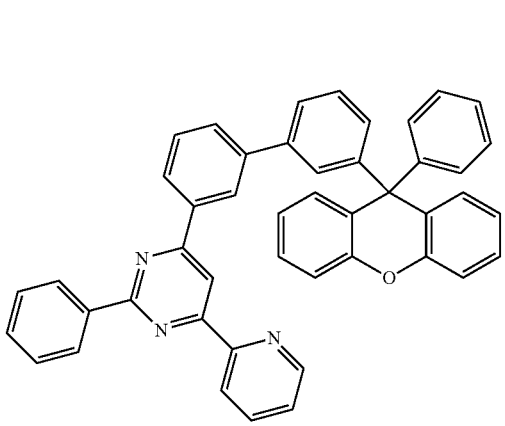

155
-continued
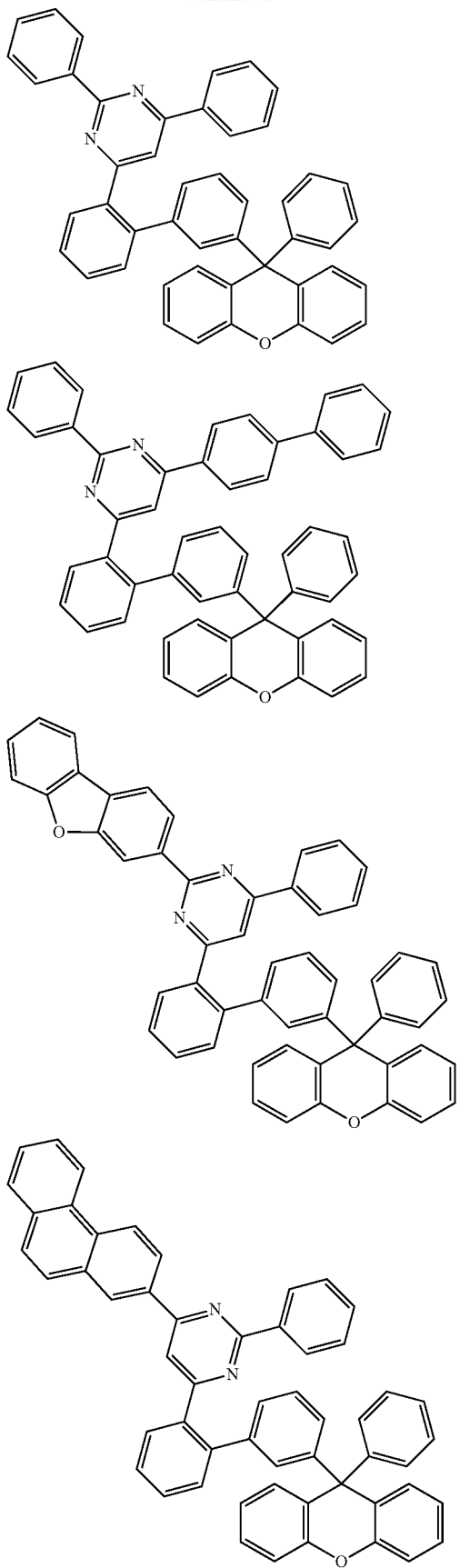
156
-continued
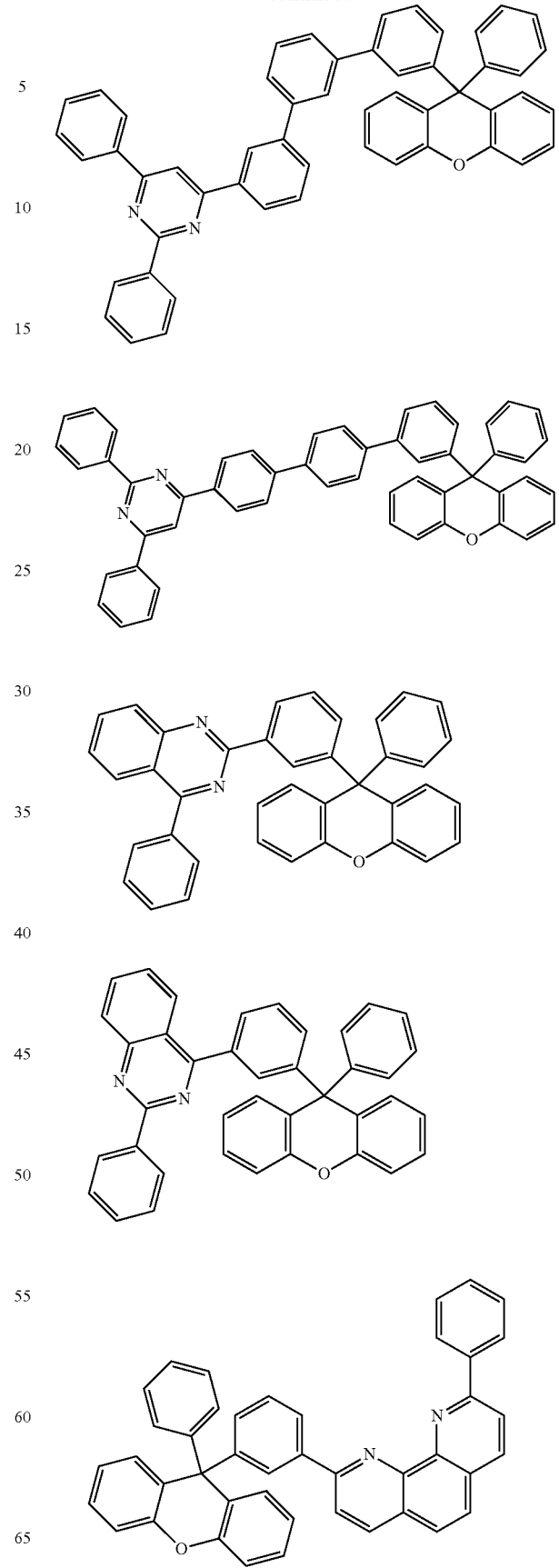

157
-continued
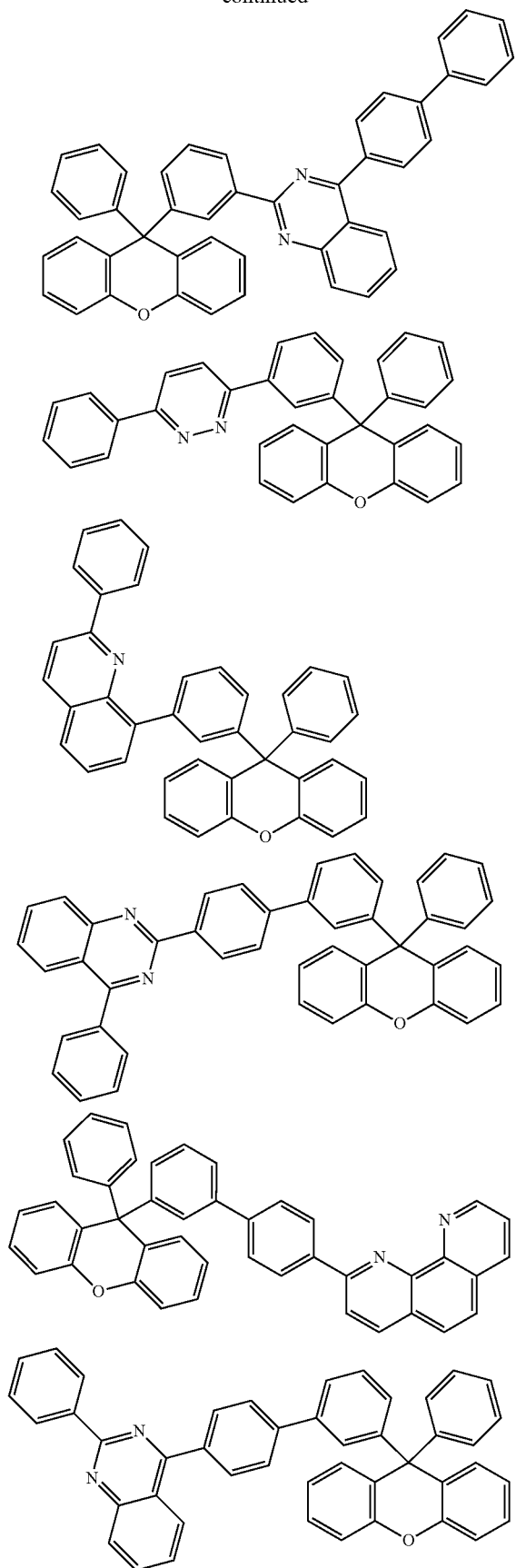
158
-continued
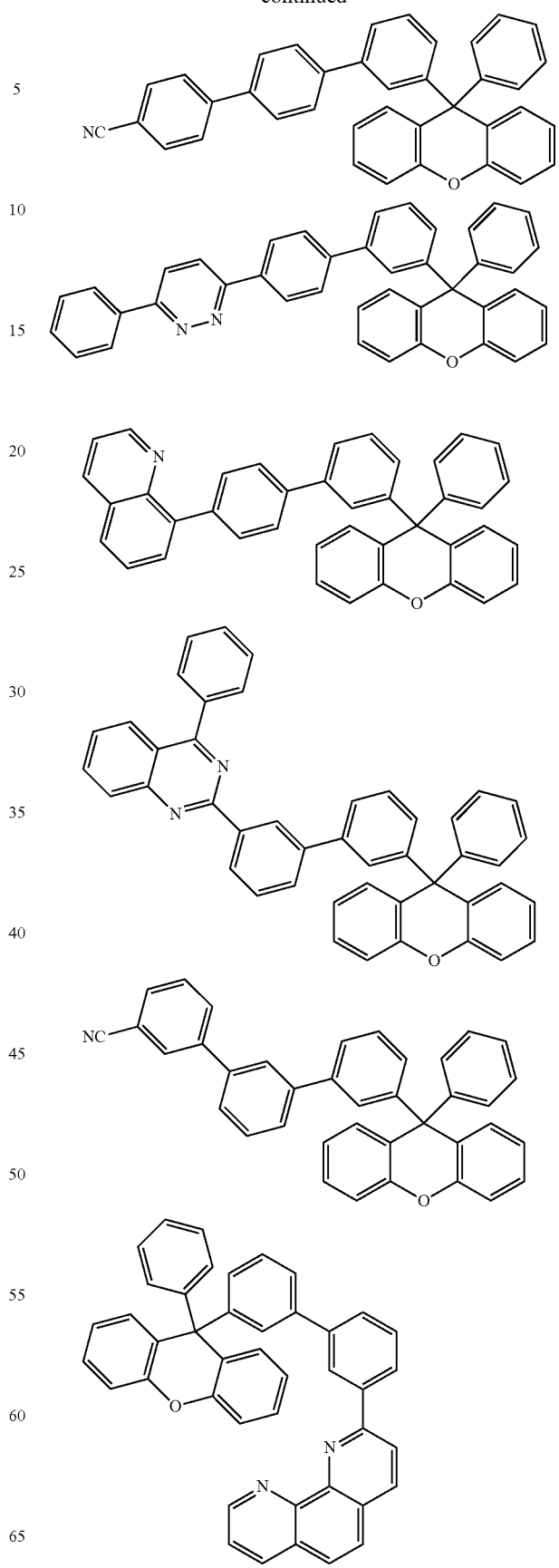

-continued
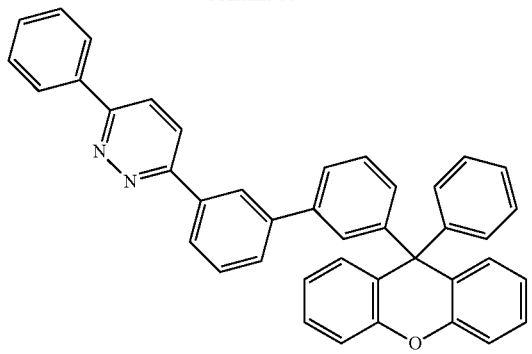
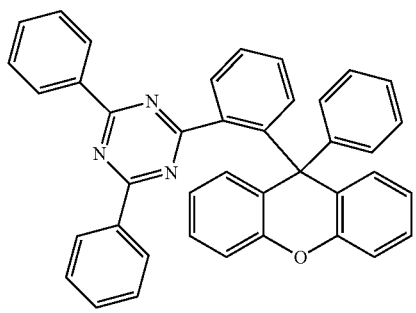
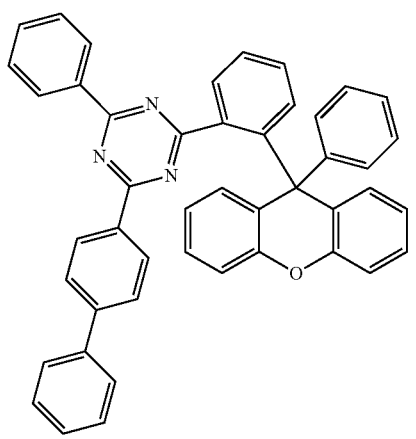
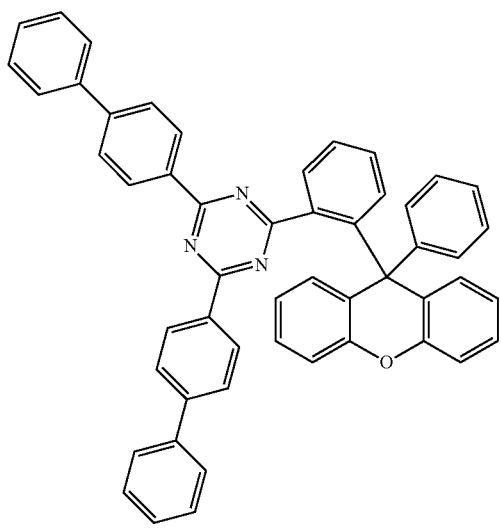
-continued
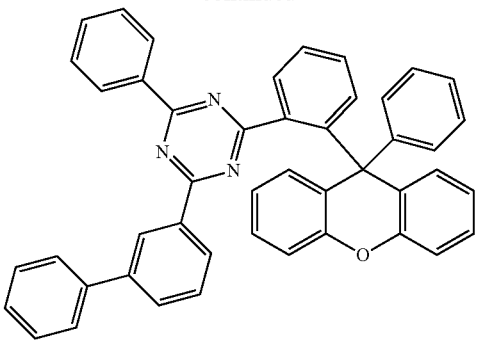
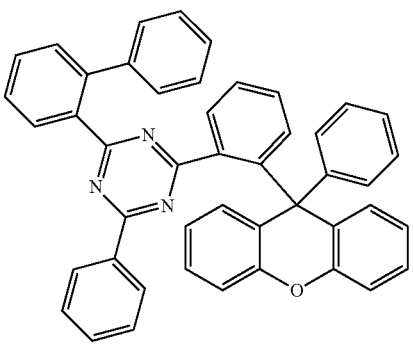
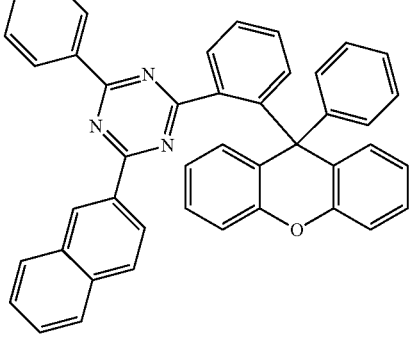
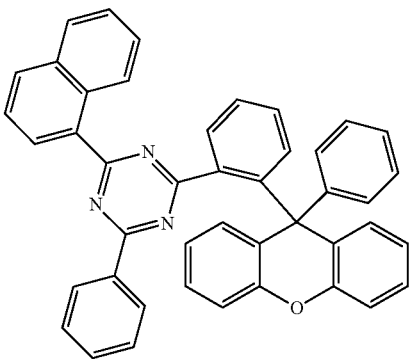
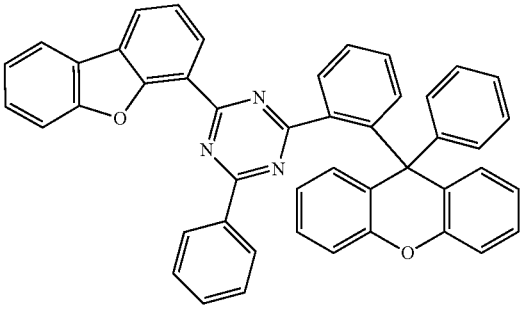

161
-continued
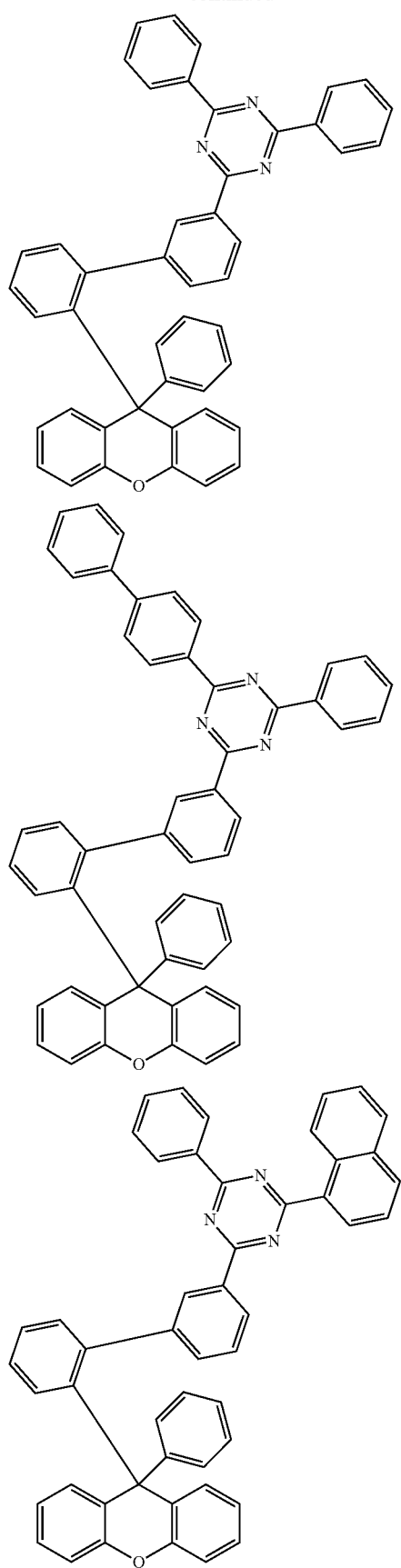
162
-continued
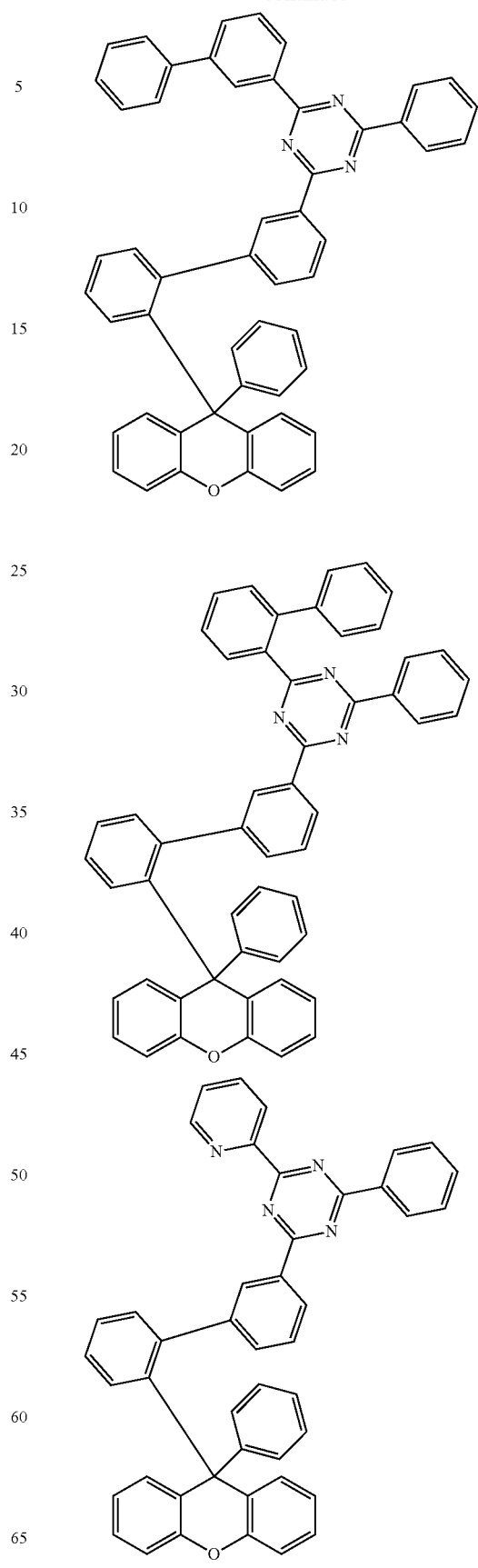

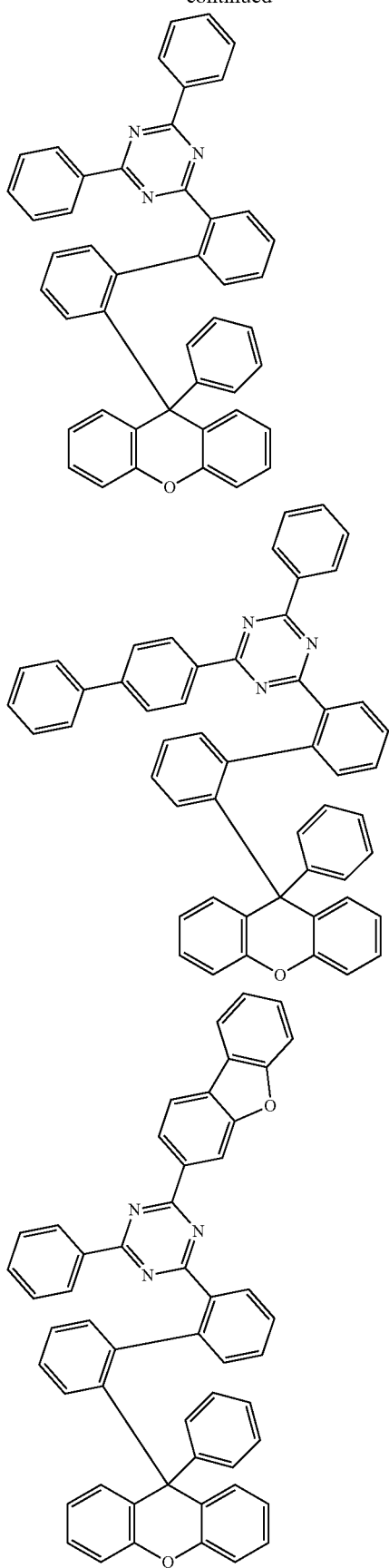
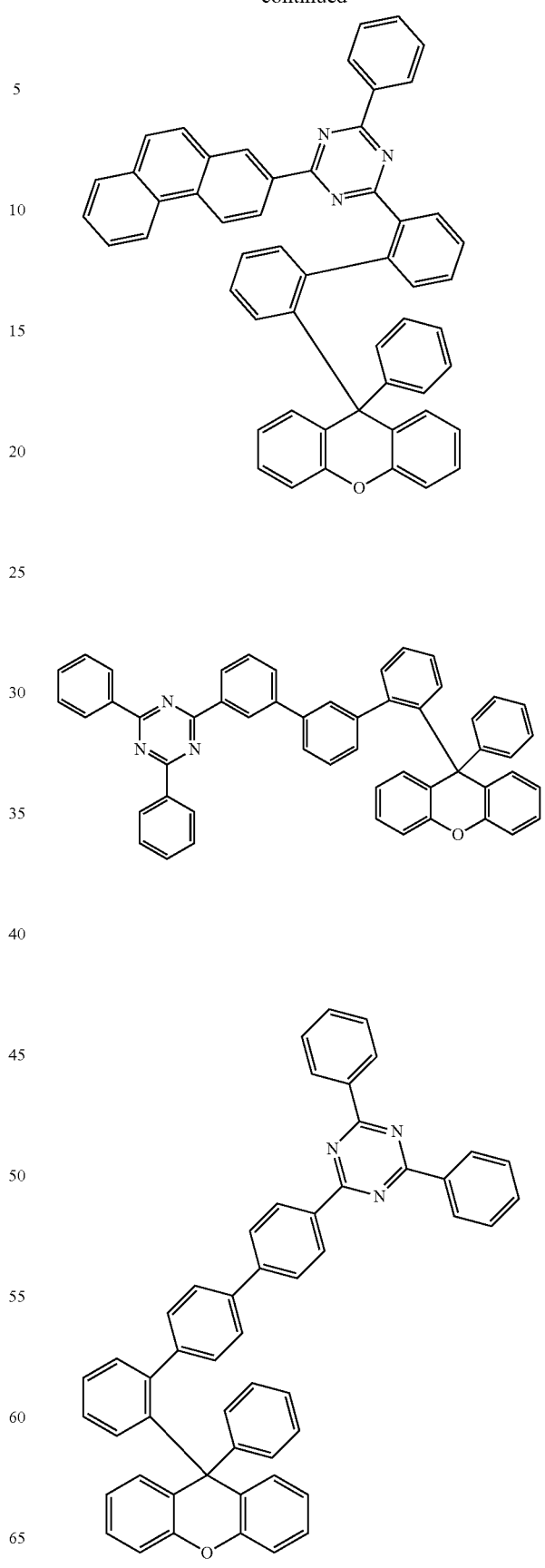

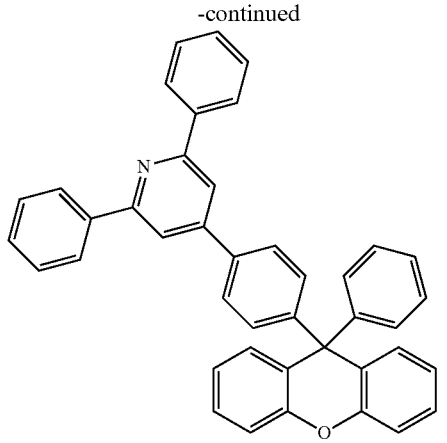
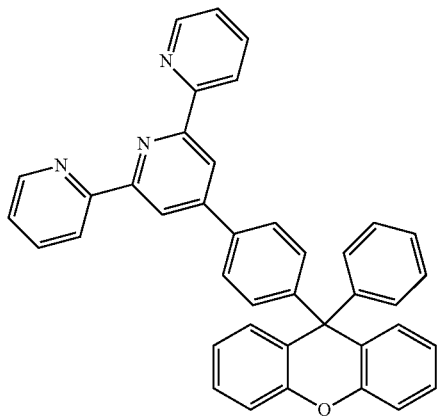
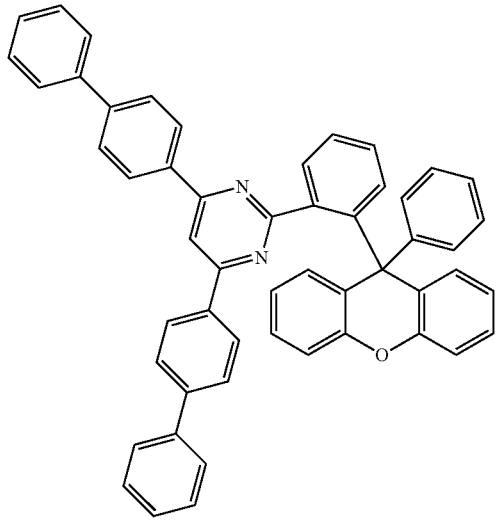
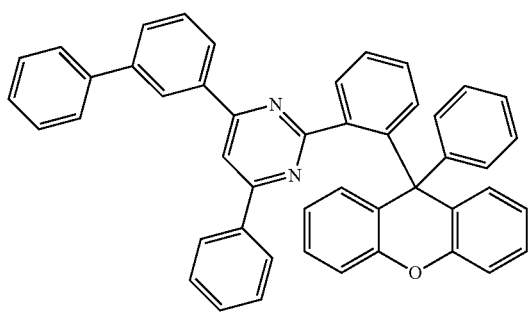
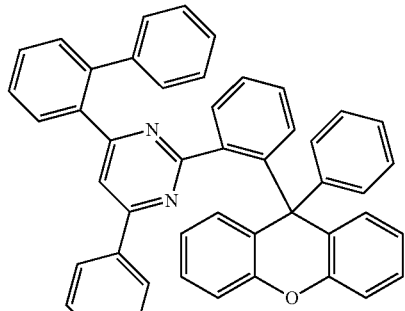
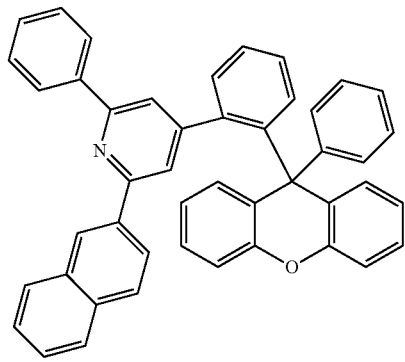
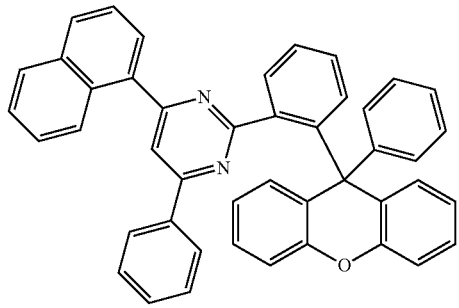
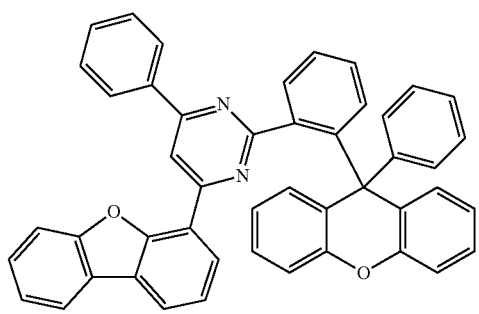

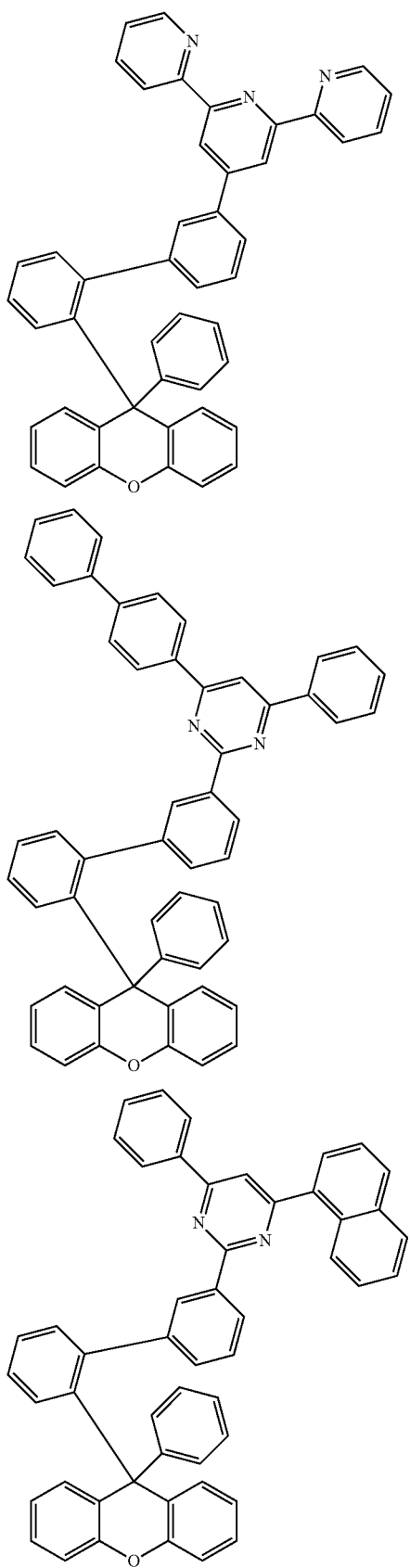
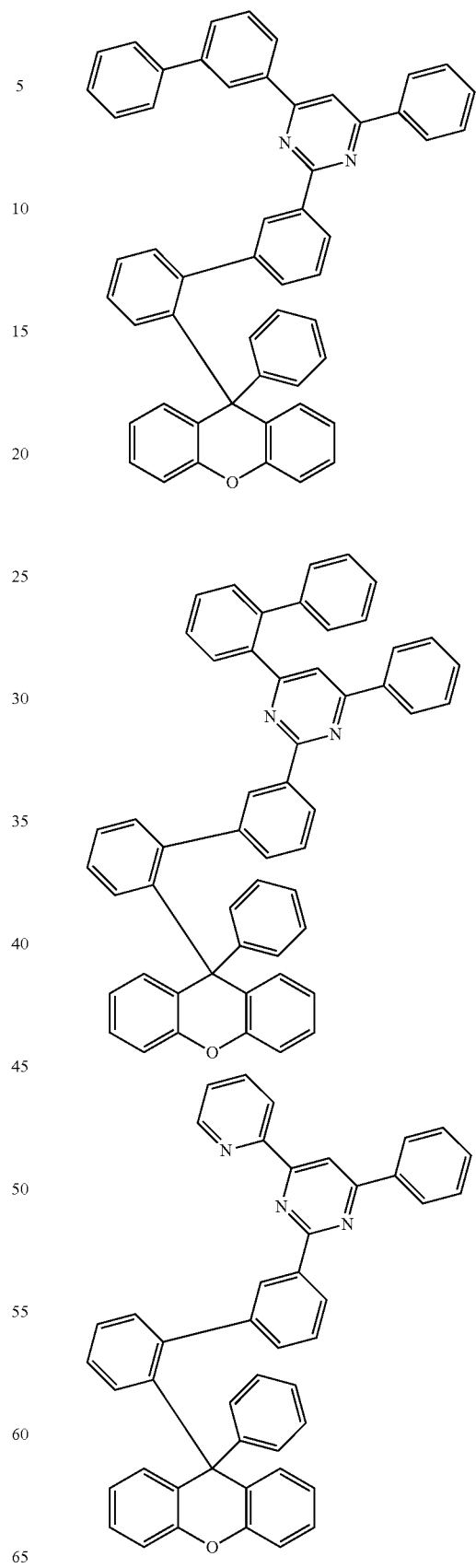

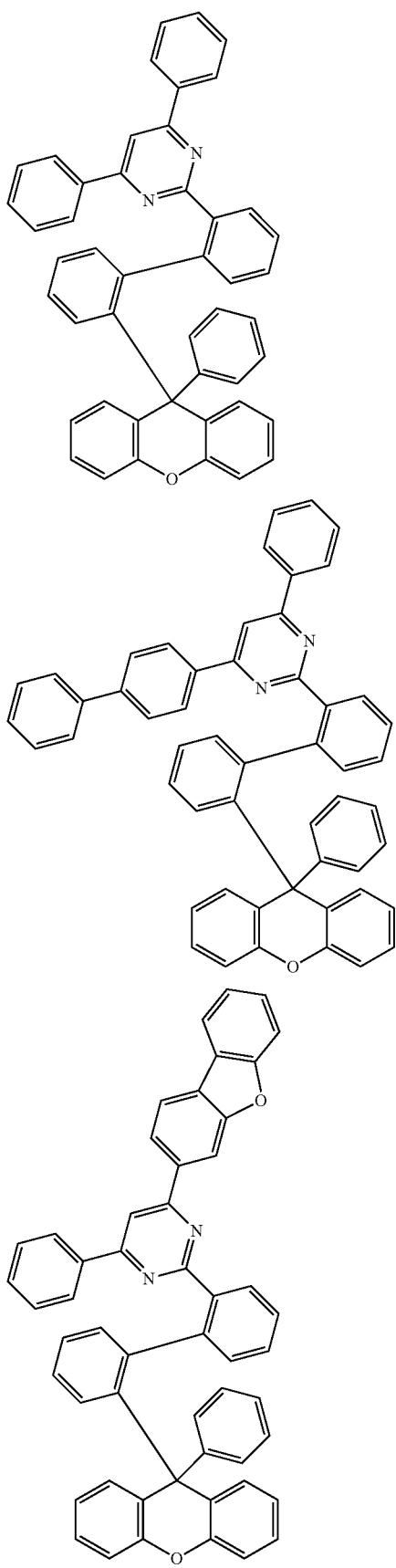
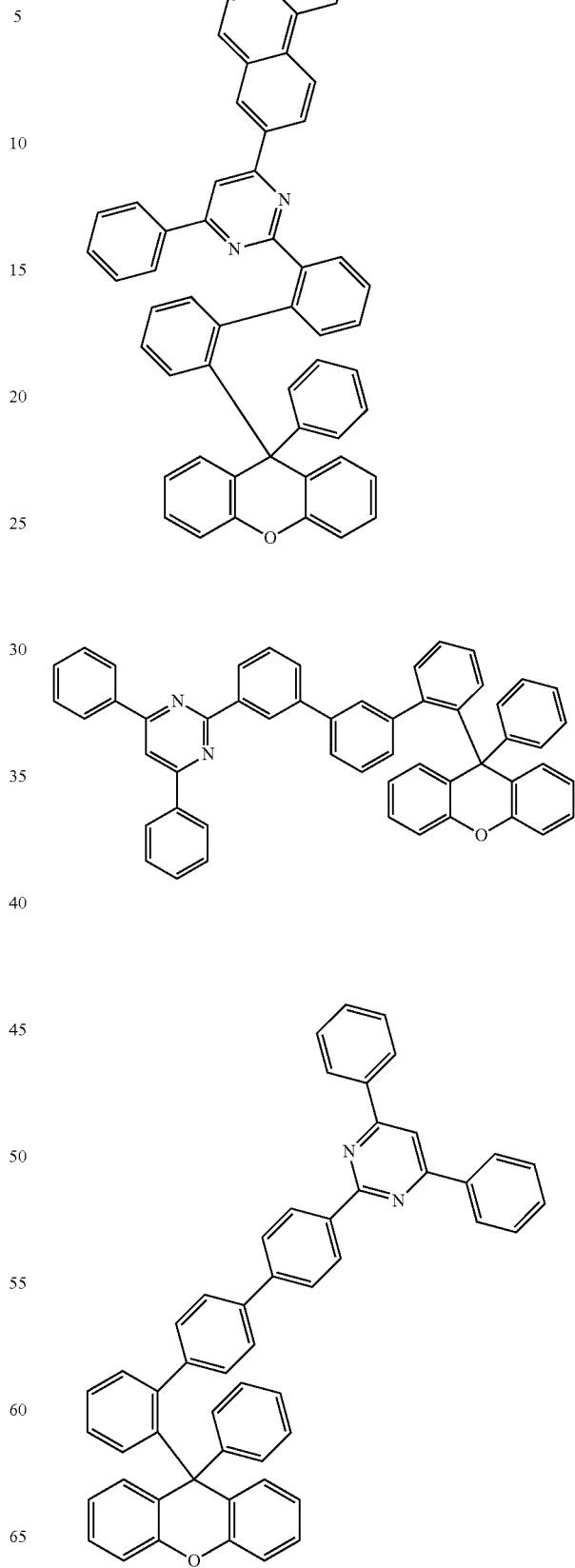

171
-continued
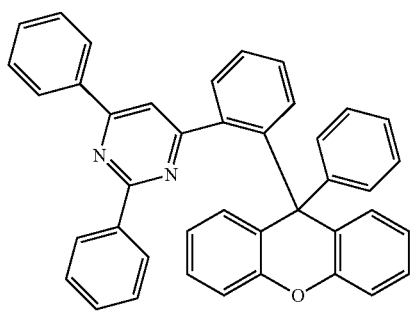
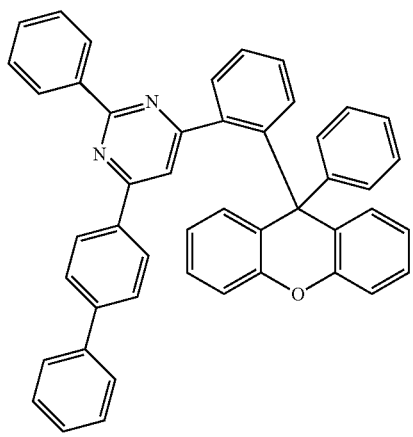
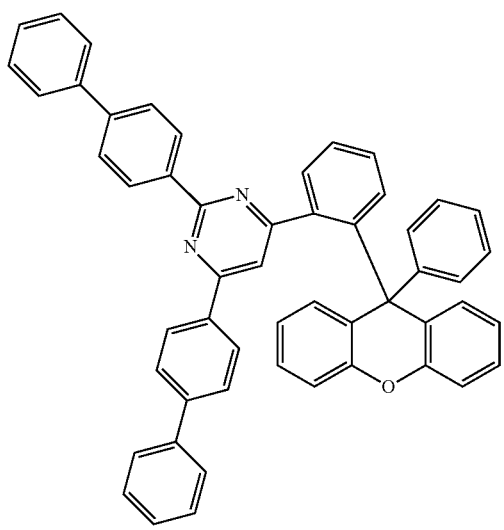
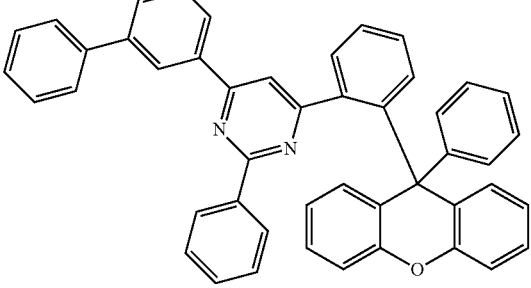
172
-continued
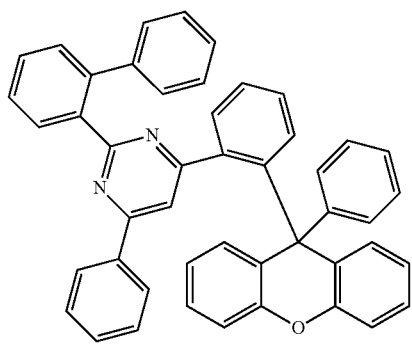
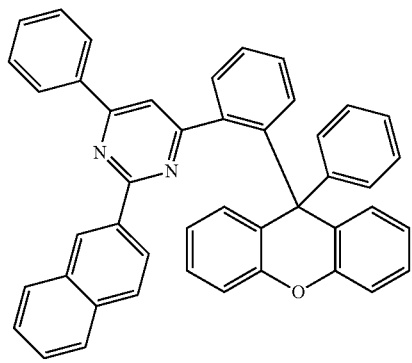
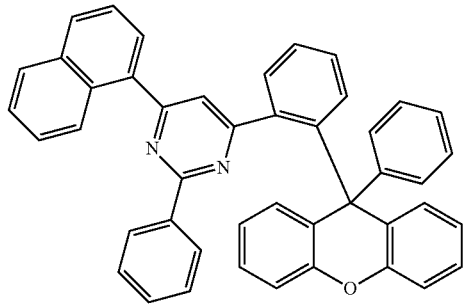
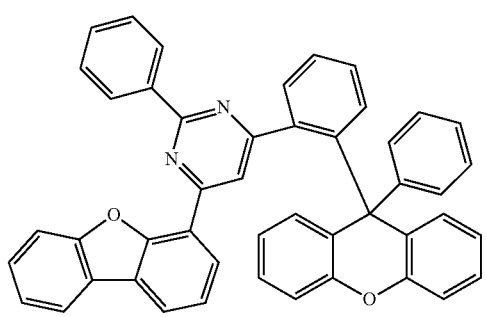

173
-continued
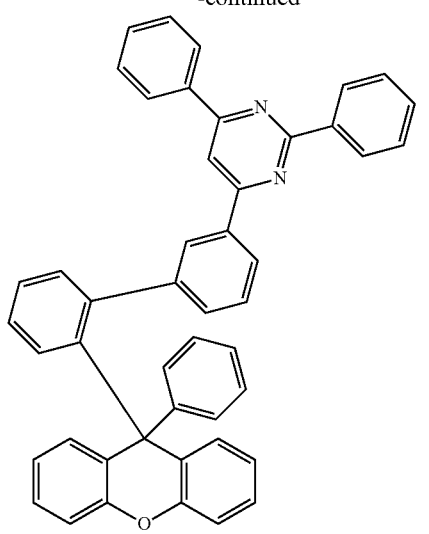
174
-continued
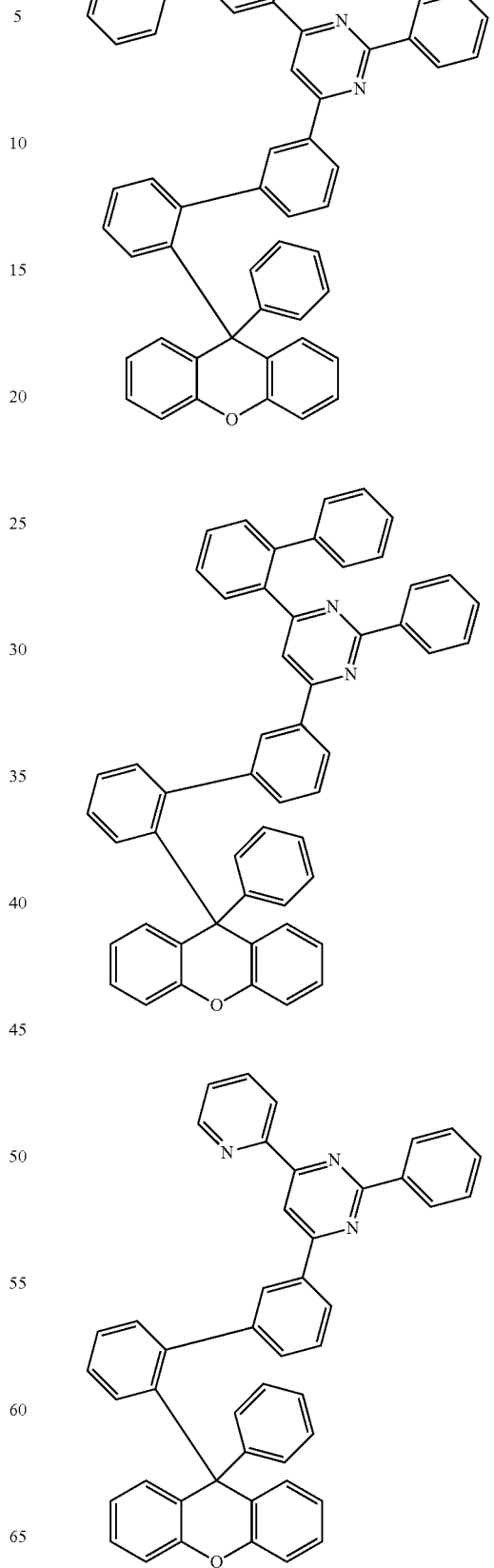

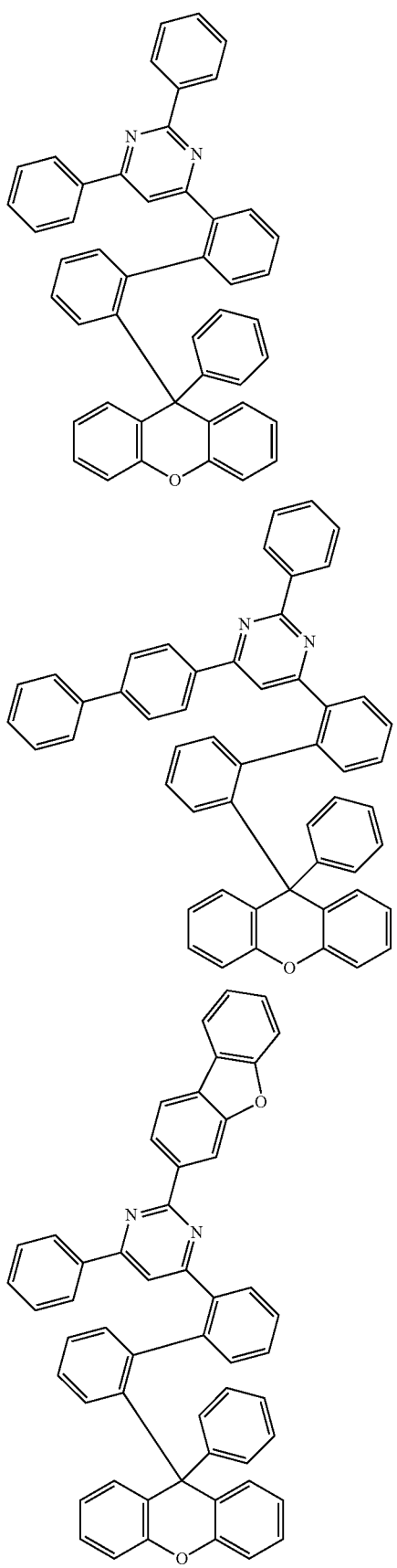
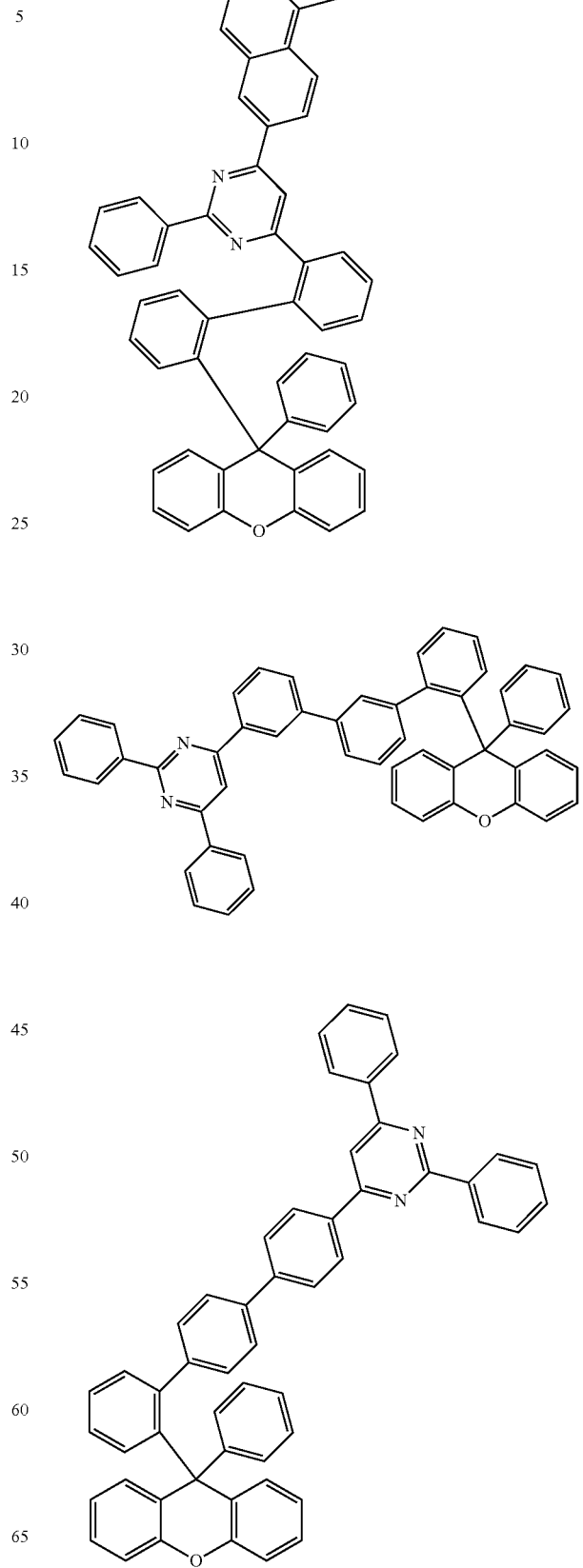

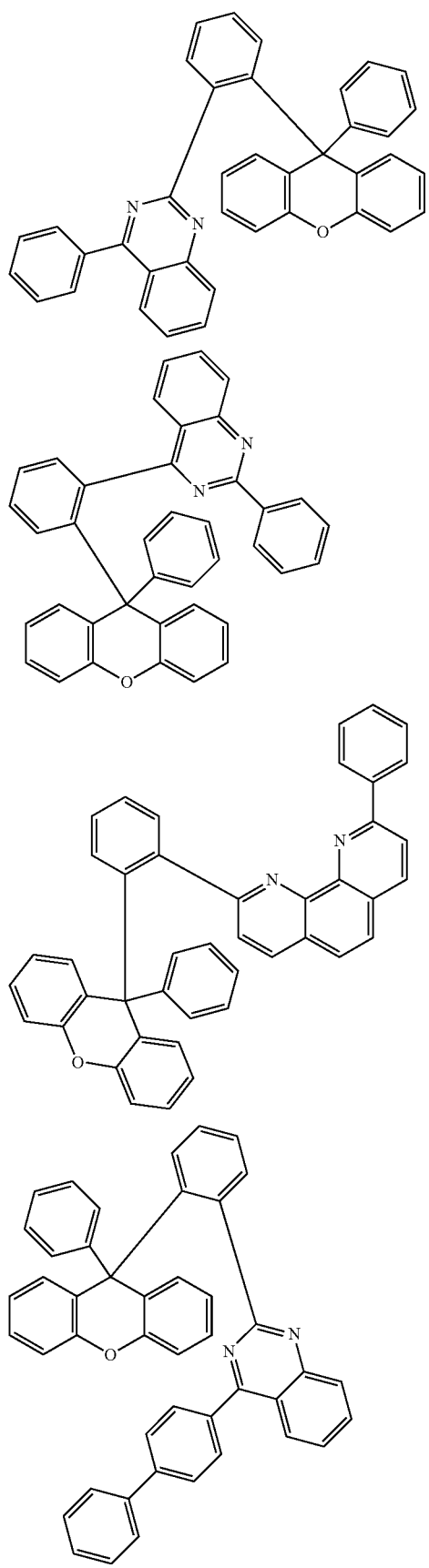
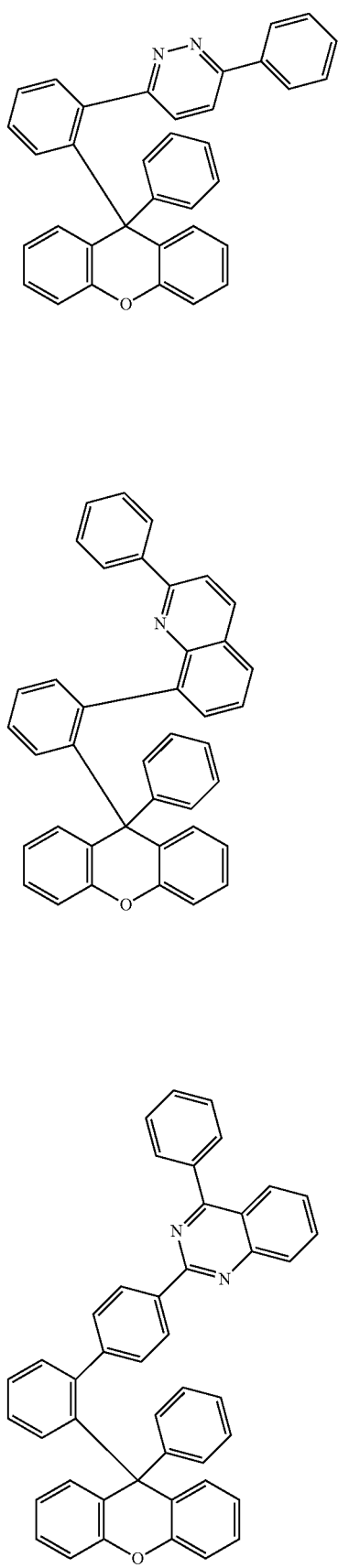

179
-continued
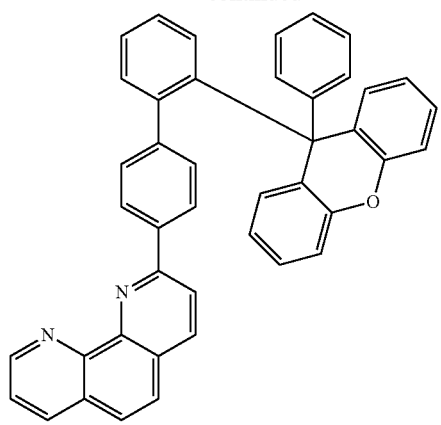
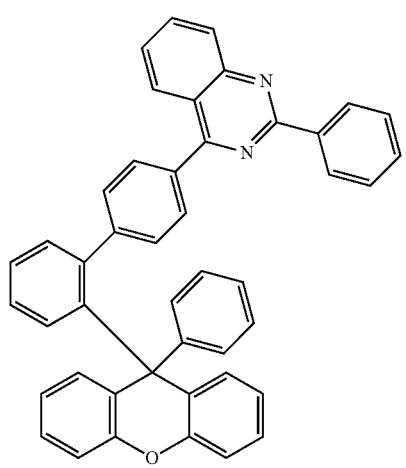
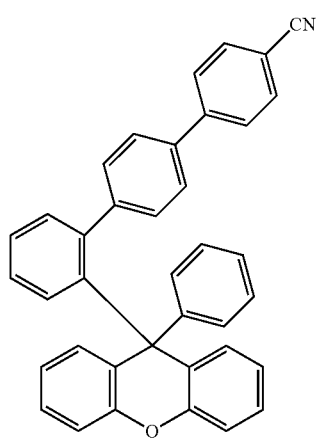
180
-continued
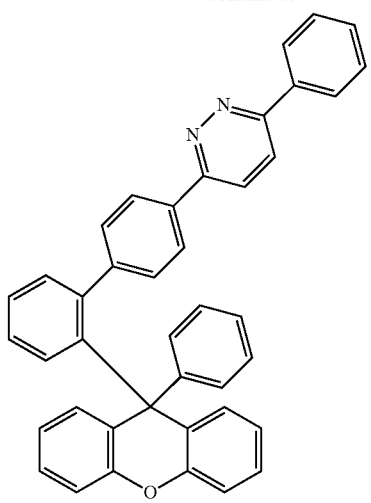
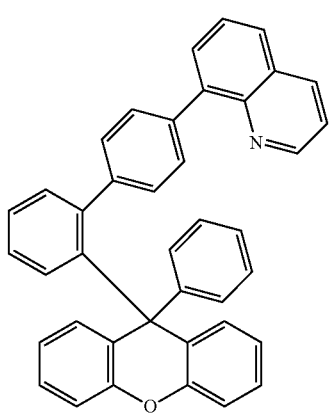
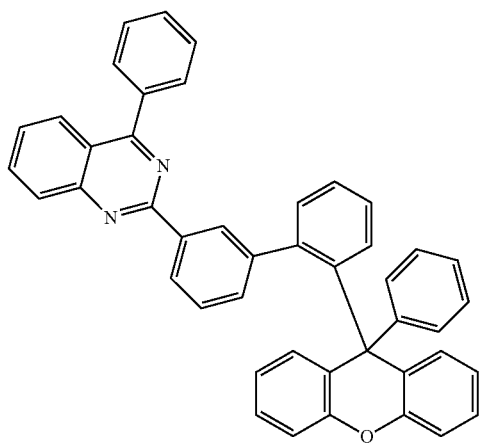

-continued

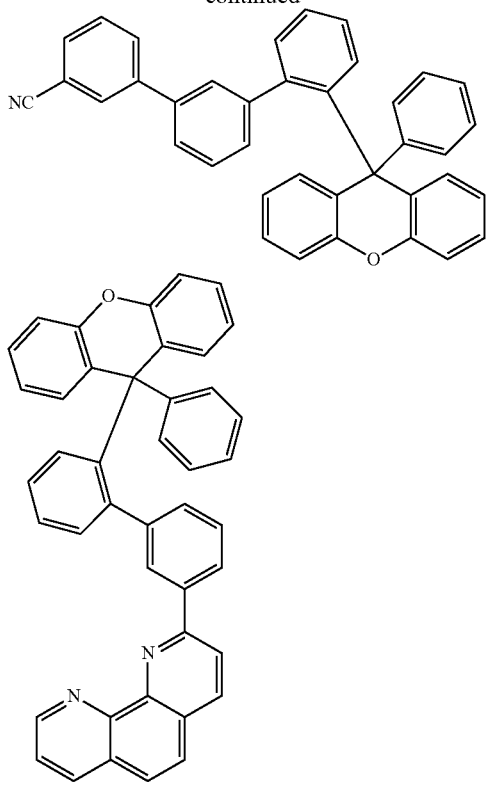

-continued

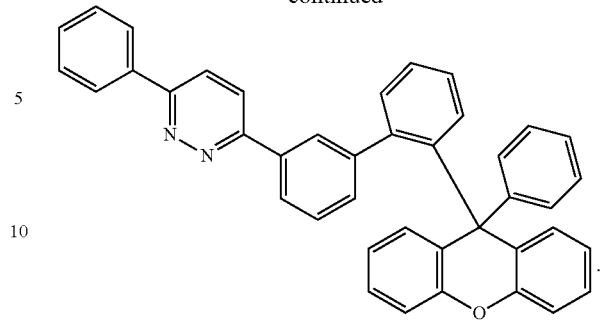

6. An organic light emitting device comprising:
a first electrode;
a second electrode disposed to face the first electrode; and
an organic material layer having one or more layers disposed between the first electrode and the second electrode,
wherein one or more layers of the organic material layer comprise the compound according to claim 1.

7. The organic light emitting device of claim 6, wherein the organic material layer comprises an electron transporting layer, an electron injection layer, or an electron injection and transporting layer, and the electron transporting layer, the electron injection layer, or the electron injection and transporting layer comprises the compound.

* * * * *